United States Patent [19]
Demarest et al.

[11] Patent Number: 5,473,810
[45] Date of Patent: Dec. 12, 1995

[54] NEEDLE-SUTURE ASSEMBLY AND PACKAGING SYSTEM

[75] Inventors: David Demarest, Parsippany; Robert B. Duncan, Bridgewater; Martin Sobel, Flemington, all of N.J.; Timothy P. Lenihan, Morrisville, Pa.; William Rattan, Cerritos, Calif.; John F. Blanch, Tinton Falls; Michael G. Hodulik, Dunellen, both of N.J.; Dennis P. Yost, Wayne, Pa.

[73] Assignee: Ethicon, Inc., Somerville, N.J.

[21] Appl. No.: 181,606

[22] Filed: Jan. 13, 1994

[51] Int. Cl.⁶ .................................................. B23Q 15/00
[52] U.S. Cl. ........................ 29/712; 29/715; 29/783; 29/785; 29/786; 29/788; 29/792; 29/793; 29/796; 29/243.517; 29/517; 53/118; 83/153; 83/950
[58] Field of Search ...................... 606/224, 225, 606/226; 163/1, 5; 53/118, 138.1, 244, 253, 329, 430; 83/151, 153, 950; 206/63.3, 227; 29/243.5, 243.517, 283.5, 515, 516, 517, 564.6, 705, 711, 715, 783, 785, 786, 788, 792, 793, 796, 818, 712

[56] References Cited

U.S. PATENT DOCUMENTS

| | | |
|---|---|---|
| 3,611,551 | 10/1971 | Shave et al. . |
| 3,980,177 | 9/1976 | McGregor . |
| 4,072,041 | 2/1978 | Hoffman et al. . |
| 4,424,898 | 1/1984 | Thyen et al. . |
| 4,672,871 | 6/1987 | Gudmestad ............................ 83/151 |
| 4,722,384 | 2/1988 | Matsutani . |
| 4,806,737 | 2/1989 | Coates . |
| 4,832,025 | 5/1989 | Coates . |
| 4,922,904 | 5/1990 | Uetake et al. . |
| 5,226,336 | 7/1993 | Coates . |
| 5,230,424 | 7/1993 | Alpern et al. ........................ 206/63.3 |

FOREIGN PATENT DOCUMENTS 212027  9/1988  Japan ........................................ 163/1

Primary Examiner—David P. Bryant
Attorney, Agent, or Firm—Scully, Scott, Murphy & Presser

[57] ABSTRACT

An automated machine for attaching a suture to a surgical needle having a suture receiving opening formed therein, and for packaging the same in a package tray comprises a first workstation including a device for sorting a plurality of needles and orienting each needle for automatic feeding to a second swaging workstation, a second workstation including a device for automatically cutting an indefinite length of suture material to a definite length and a device for automatically swaging the needle to close the suture receiving opening about a free end of the suture to secure the suture thereto and form a needle-suture assembly, a needle packaging station including a device for sequentially receiving at least one of the needle-suture assemblies in a package tray in synchronism with the second workstation, the needle packaging station having a device for automatically winding the depending suture portion of the needle-suture assembly into the package tray, a first indexing device for sequentially receiving individual oriented needles fed from the first workstation and transferring each of the needles from the first workstation to the second workstation to form the needle-suture assembly thereat, the first indexing device sequentially indexing the needle-suture assemblies from the second workstation to the needle packaging station.

31 Claims, 47 Drawing Sheets

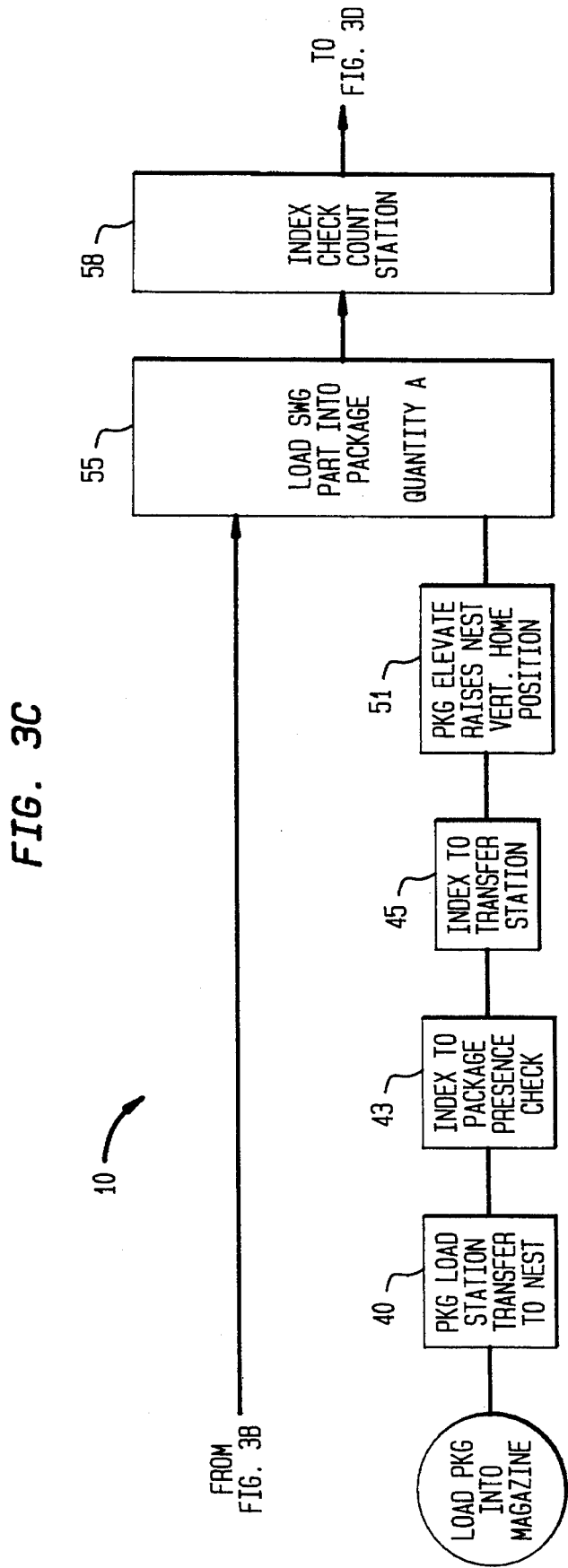

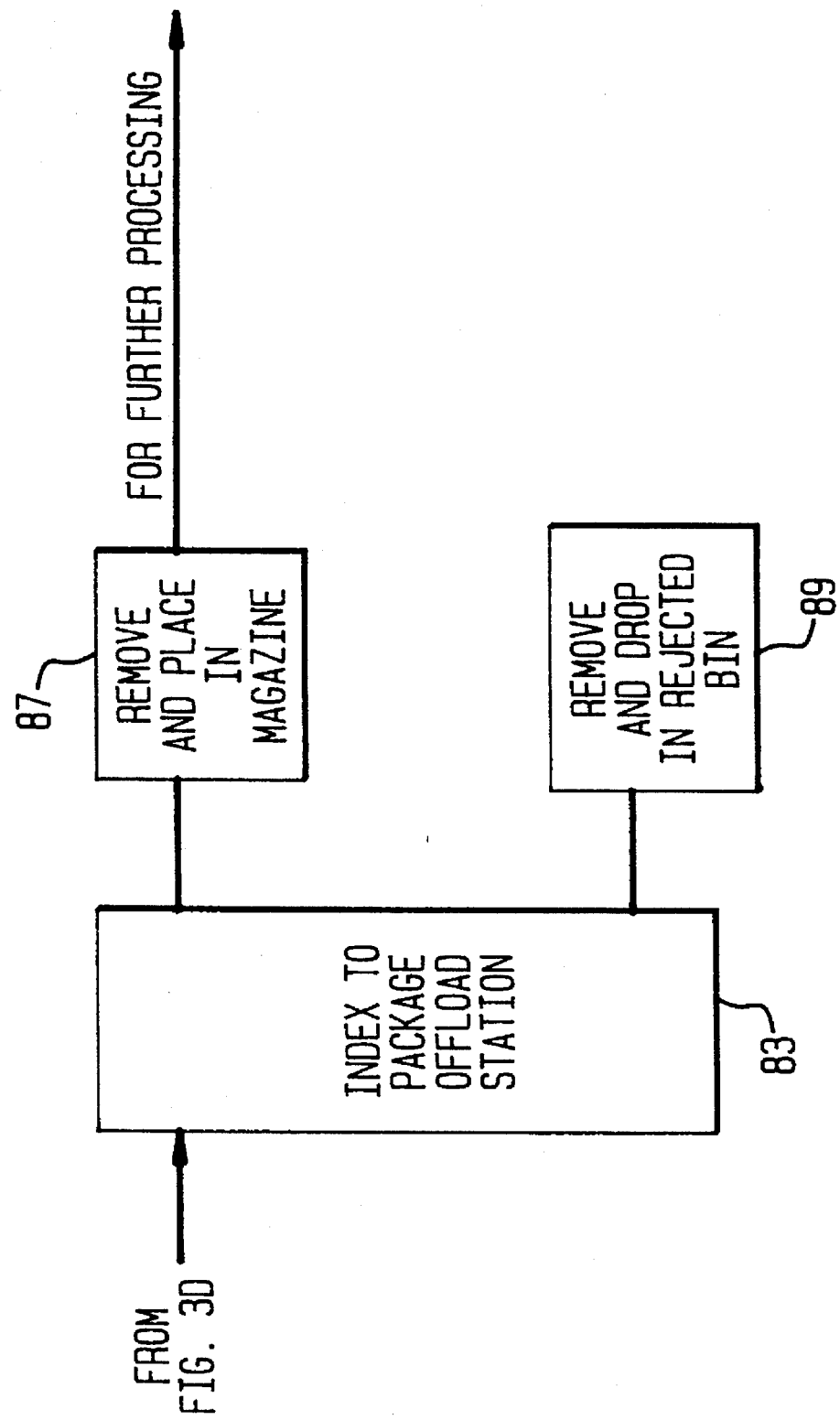

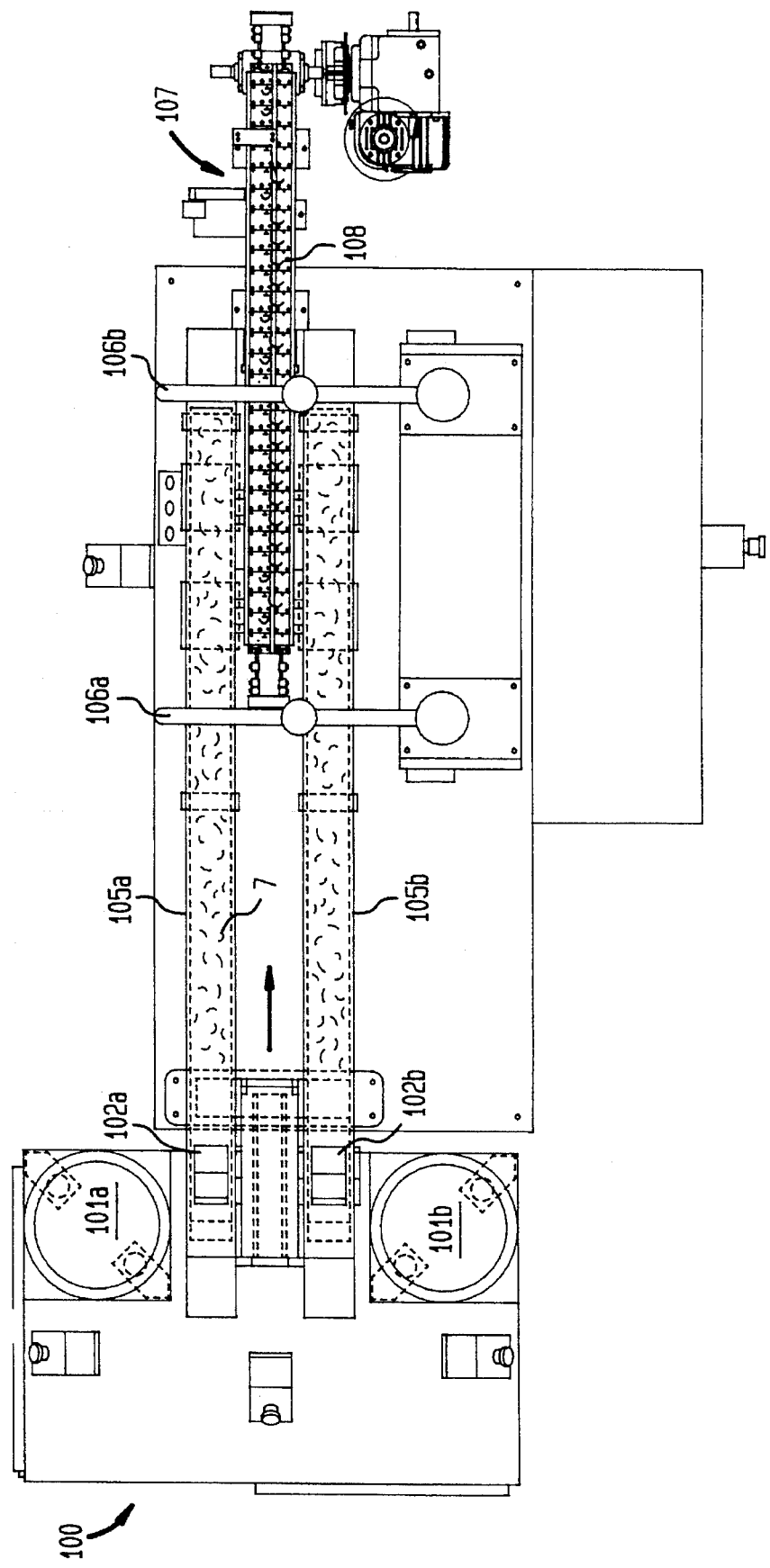

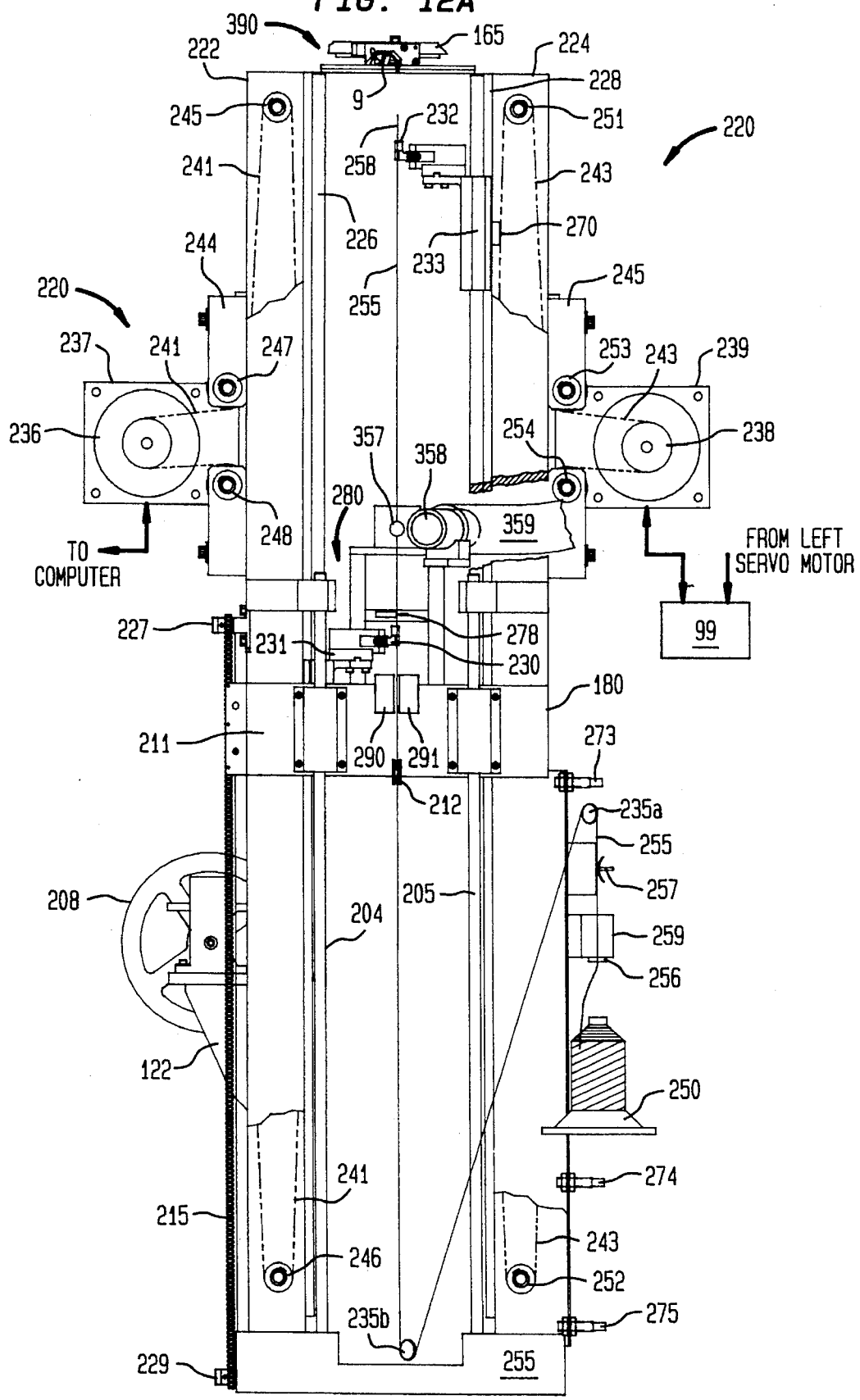

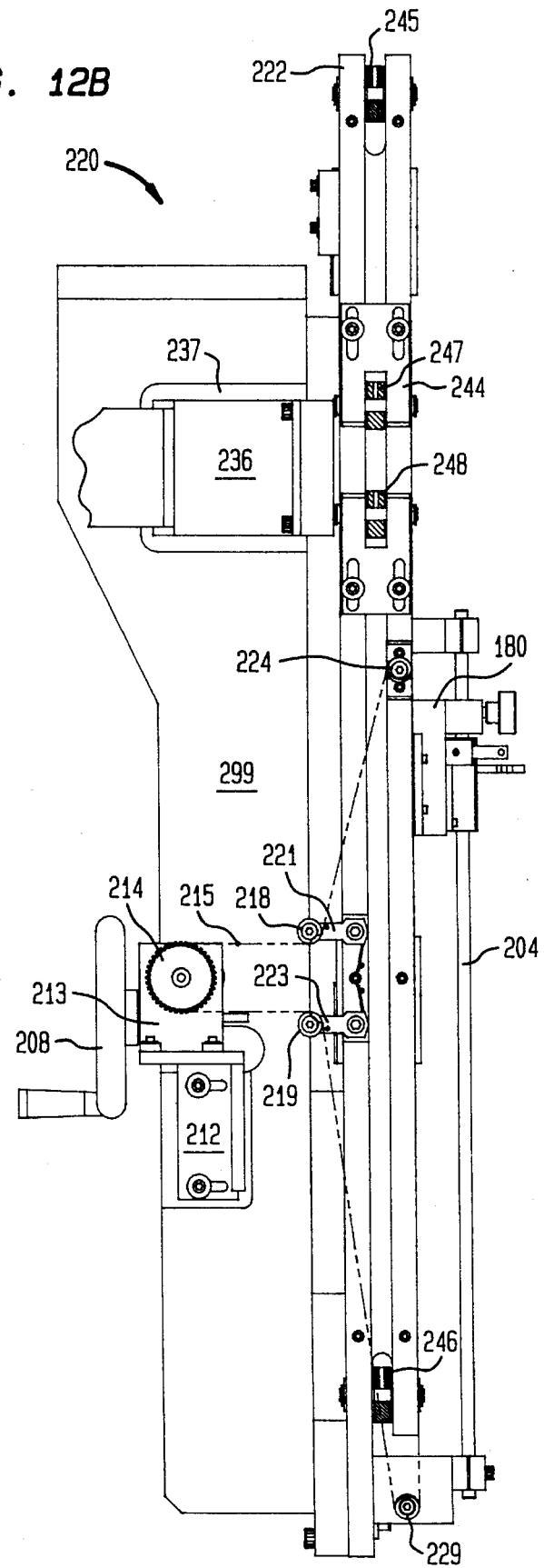

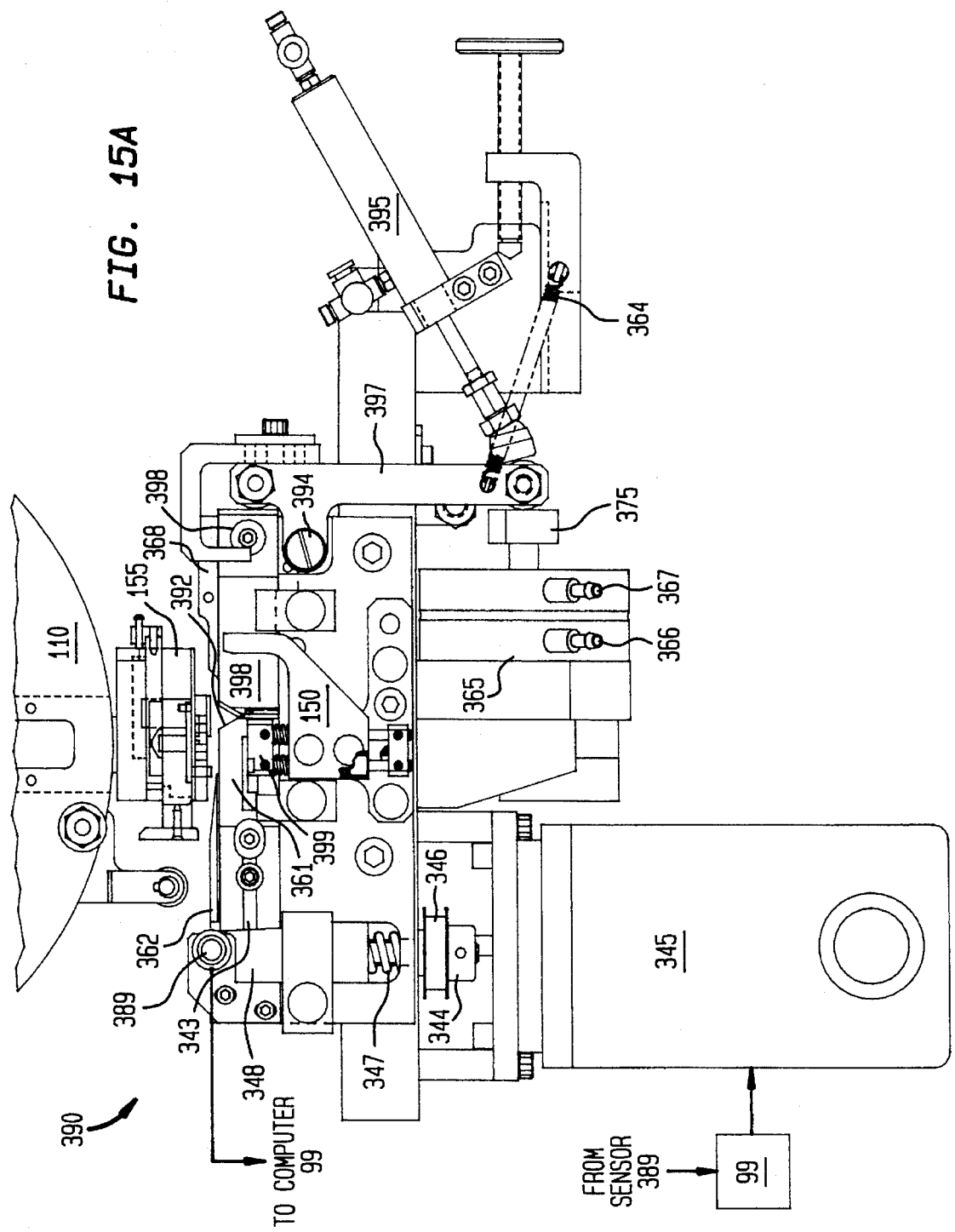

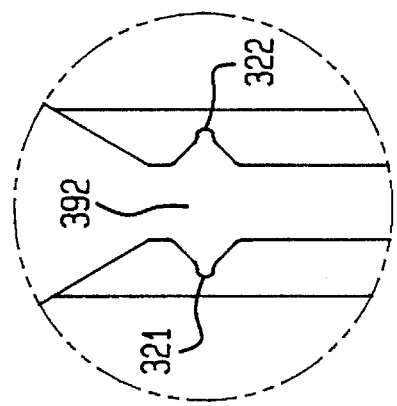
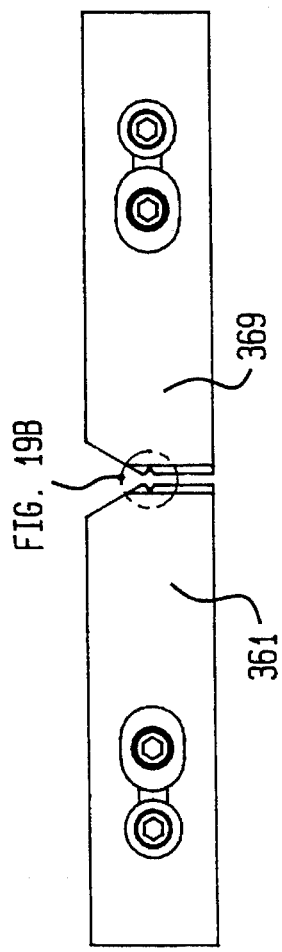

NEEDLE-SUTURE ASSEMBLY AND PACKAGING SYSTEM

FIELD OF THE INVENTION

The present invention relates generally to machines for producing armed surgical needles, i.e., surgical needles having a suture strand of predetermined length attached at one end thereof, and machines for packaging the same, and more specifically to a high-speed needle-suture assembly and packaging system that automatically assembles armed surgical needles and packages them in a organized package of unique construction.

DESCRIPTION OF THE PRIOR ART

Presently, armed surgical needles used by surgeons and medical personnel are manufactured utilizing manual and semi-automated procedures such as those described in U.S. Pat. Nos. 3,611,551, 3,980,177, and 4,922,904. For instance, as described in U.S. Pat. No. 3,611,551, manual intervention is required by an operator to accurately position a suture tip within a suture receiving opening of a surgical needle to accomplish swaging thereof. This process is costly in terms of man-hour labor and efficiency because of the manual manipulations involved.

Indefinite length of suture material may be supplied wound on a bobbin, or, a king or driven spool before being cut and positioned within the swaging end of a surgical needle. In U.S. Pat. No. 3,980,177 the suture material is fed from a spool and taken up on a rotating tension rack where uniform length strands are subsequently cut. Thus, the length of the suture is determined by the size of the rack and manual intervention is required to prepare the rack for the cutting of the suture material wound thereabout. Moreover, manual intervention is required to change the rack each time a suture strand of different length is desired.

In U.S. Pat. No. 4,922,904, the suture material is supplied wound on a bobbin and is fed through various guide means prior to insertion within the suture receiving end of the surgical needle. In one embodiment shown therein, an elaborate television monitoring means is required for aligning the drawn suture within the suture receiving opening of the surgical needle prior to swaging thereof. In the same embodiment, a rotary encoder device is used to determine the length of suture material unwound from the bobbin prior to cutting. In an alternative embodiment, after swaging of the indefinite length of suture material to the needle, the needle-suture assembly is additionally fed a predetermined distance prior to cutting to obtain a suture strand of predetermined length. Thus, to obtain uniform lengths of suture material every time requires careful manipulations and precise controls, and the processes used to accomplish these tasks are slow and inefficient.

Additionally, at the present time, the introduction of needles with attached sutures into suture packages or molded plastic trays is being implemented in a substantially manual manner. In that instance, the needles are manually placed into the tray so as to be clampingly engaged by means of suitable needle-gripping structure, and thereafter the attached sutures are wound or positioned within the confines of the tray. Subsequently, a suitable cover is superimposed upon and fastened to the filled tray, and the resultant suture package conveyed to a suitable arrangement for possible sterilizing or further overwrapping.

The foregoing essentially manual and relatively basic process for winding the sutures into the tray, and especially the locating thereof into a peripheral channel of the tray during manipulation of the tray, is quite time-consuming, and in conjunction with the manual application of the cover into the tray in a basically individual or piece-by-piece mode, represents a serious hindrance to a high volume mass produced manufacturing output, and adversely affects the economics in attempting to provide such large quantities of suture packages containing multiple surgical needles and attached sutures.

In view of the limitations of the devices described in the aforementioned patents, it would be desirable to provide a needle-suture assembly and packaging system that is fully automated and which can automatically prepare surgical needles having uniform lengths of suture material attached thereto.

Furthermore, it would be desirable to provide a needle-suture assembly and packaging system facilitating the automated high-speed packaging of surgical needles having sutures attached thereto.

Furthermore, it would be highly desirable to provide an automatic high-speed needle threading and swaging system and automatic high-speed packaging system that is computer controlled and that can provide automatic adjustments to the swage tooling dies when different size sutures are swaged to correspondingly sized surgical needles.

SUMMARY OF THE INVENTION

Accordingly, it is an object of the present invention to provide an automatic needle-suture assembly and packaging machine for producing and packaging armed surgical needles in a package of unique construction and, packaging the same that is operable under the control of a control system computer.

It is another object of the instant invention to provide a cost-effective automatic needle-suture assembly and packaging machine that virtually eliminates operator exposure to any repetitive manual operations.

It is still another object of the instant invention to provide an automatic needle-suture assembly and packaging machine that incorporates a rotatable swage dial having a plurality of multi-axis grippers that automatically grip surgical needles for indexing to a plurality of processing stations that include: a loading station for transferring individual precisely oriented surgical needles from a conveyor to the multi-axis grippers; a swaging station that automatically draws an indefinite length strand of suture material, cuts the strand, inserts the free end of the definite length strand within the suture receiving end of the needle, and swages the suture strand to the surgical needle; a pull-test station that automatically performs minimum and n-count destructive pull-testing of the needle-suture combination; and finally, a needle-suture load to package station where armed, pull-tested needles are transferred to the automatic packaging station for packaging thereof.

Yet another object of the present invention is to provide an automatic needle-suture assembly and packaging machine that incorporates a rotatable suture winding and packaging dial having a plurality tool nests, each for supporting a package tray for indexing to a plurality of workstations that include: a package load station for loading an empty package tray onto a supporting structure of the tool nest; a package detect station for detecting the presence of an empty package tray; a needle-suture load to package station where armed needles are transferred to the package from the rotary swage dial; a needle check station where the presence or absence of the armed needles is checked; a winding station where the sutures that depend from each surgical needle are gathered to a bundle and wound around a peripheral channel located about the periphery of the package tray; a cover loading station where a cover is applied to the package; and finally, a package removal station where the completed package is removed from the machine, or rejected if the package is flawed.

Yet still another object of the present invention to provide a high-speed automatic needle-suture assembly and packaging machine that is operable under the control of a control system computer and can provide continuous on-line tool adjustments without unnecessary interruptions and without manual intervention.

These and other objects of the present invention are attained with an automated machine for attaching a suture to a surgical needle having a suture receiving opening formed therein, and for packaging the same in a package tray, the automated machine comprising: a first workstation including means for sorting a plurality of needles and orienting each needle for automatic feeding to a subsequent workstation; a second workstation including means for automatically cutting an indefinite length of suture material to a definite length suture strand and means for automatically swaging the needle to close the suture receiving opening about a free end of the suture to secure the suture thereto and form a needle and suture assembly; a needle packaging station including means for sequentially receiving at least one of the needle-suture assemblies in a package tray in synchronism with the second workstation, the needle packaging station having a means for automatically winding the suture into the package tray; a first indexing means for sequentially receiving individual oriented needles fed from the first workstation and transferring each of said needles from the first workstation to the second workstation to form the needle-suture assembly thereat, the first indexing means sequentially indexing the needle-suture assemblies from the second workstation to the needle packaging station, whereby unsorted needles and an indefinite length of suture material are automatically formed into a plurality of oriented needle and suture assemblies and positioned within the package to facilitate their orderly removal therefrom.

Further benefits and advantages of the invention will become apparent from a consideration of the following detailed description given with reference to the accompanying drawings, which specify and show preferred embodiments of the invention.

BRIEF DESCRIPTION OF THE DRAWINGS

FIGS. 3(a)–3(e) are the general flow diagrams illustrating the process for needle-suture assembly and packaging of the present invention;

FIG. 4 is a top plan view of the needle sorting station 100 of the automated needle threading and swaging system;

FIG. 8(a) is detailed top view of the cam dial assembly 120 having cam dial plate 125 with cam follower 165a in a retracted position within cam track 160a;

FIG. 8(b) is cut away top view of the cam dial plate 125 showing cam follower 165a in an extended position within cam track 160a;

FIG. 12(a) is a detailed view of the servo assembly (suture drawing) tower 220 of the instant invention, and additionally showing a multi-axis gripper 155 indexed thereat;

FIG. 12(b) is a detailed side view of the cutting assembly of FIG. 12 showing the pulley assembly for moving tip and cut carrier assembly 180 of the instant invention;

FIG. 15(a) is a top view of the swage assembly 390 of the instant invention with the multi-axis gripper 155 indexed thereat;

FIG. 19(a) is a detailed top view of the swage dies 361,369 of the swaging assembly showing the recesses 321,322 formed in the swage die opening 392 located therebetween;

FIG. 19(b) is an enlarged view of the swage die opening shown encircled in FIG. 19(a);

DETAILED DESCRIPTION OF THE PREFERRED EMBODIMENT

Figure 1:
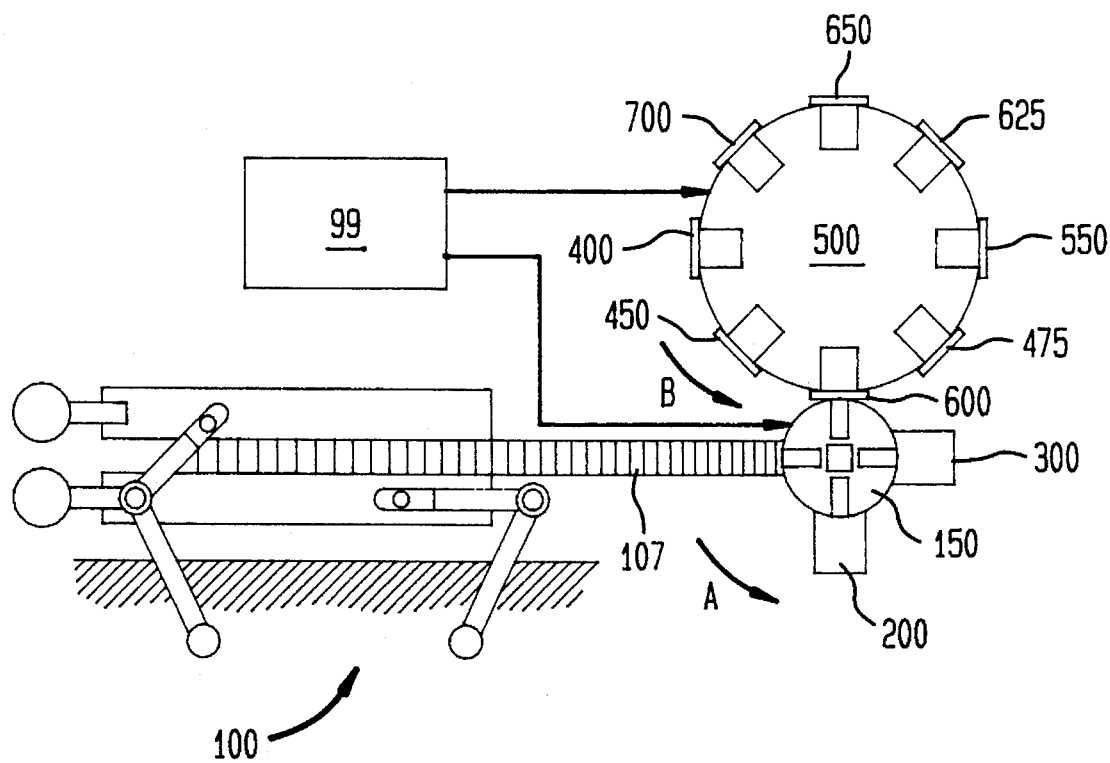
FIG. 1 is a conceptual top view of the needle threading and swaging machine and automatic packaging machine that are operable under the control system of the instant invention.
Figure 2:
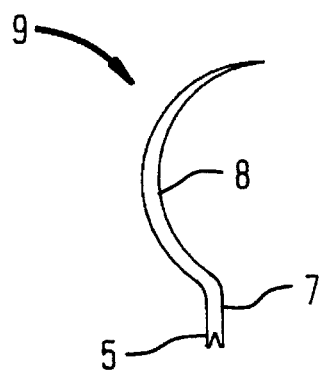
FIG. 2 is a detailed illustration of a typical surgical needle 9 having an arcuate portion 8 and suture receiving end 7.

Generally, as shown in the conceptual plan view of the needle threading and swaging system and needle-suture packaging system of FIG. 1, parallel operations take place simultaneously at four (4) different workstations positioned about a rotary swage dial 150 to ensure a high rate of production of surgical needles having sutures attached thereto. Additionally, parallel operations take place simultaneously at eight (8) different workstations positioned about the larger suture winding and packaging turret 500 where the armed surgical needles are automatically parked into a reduced size organizer package of unique construction. FIG. 2 illustrates a typical surgical needle 9 having a suture receiving opening or end 7 for swaging a suture strand thereto, and an arcuate blade portion 8.

The automatic needle threading and swaging portion of the invention shown in FIG. 1 includes four workstations located about the periphery of the rotary swage dial 150 that are successively utilized to form needle-suture assemblies. These workstations include: a needle sorting station 100 that sorts, singulates, and conveys precisely oriented surgical needles to a plurality of retractable (multi-axis) grippers mounted on the rotary swage dial 150. The rotary swage dial 150 successively rotates counter-clockwise as shown by arrow "A" in FIG. 1, to index each needle to the automatic swaging station 200 where the suture material inserted into the needle, cut, and automatically swaged thereto. Next, the rotary swage dial 150 rotates further to index the armed needle to the automatic pull-test station 300 where each armed needle is pull-tested to ensure that minimum and/or destructive pull-test requirements are met. Then, the rotary swage dial 150 indexes the pull-tested armed needle to a discharge station 600 where the armed surgical needles are handed off to a package tray of unique construction at the rotary suture winding and packaging turret 500 for automatic packaging thereof. Hereinafter, the discharge station 600 will be referred to as the needle-suture load to package station.

Generally, the automatic packaging portion of the invention shown in FIG. 1, includes eight (8) workstations located about the periphery of the rotary suture wind and packaging dial 510 that are successively utilized to form the completed package of surgical needles. These stations include: a package load station 400 for successively feeding an empty package onto a support plate of a tool nest mounted on the packaging dial; an optional package detect station 450 for checking the presence of the loaded empty package; the needle-suture load to package station 600; an optional needle check station 475 for detecting missing needles; a suture winding station 550 where the trailing sutures of the armed needles are gathered and wound into the package; an optional manual inspection station 625; a paper insert station 650 where a paper cover is applied to the package; and, a package removal station 700 where the completed package is removed from the machine for further processing, or, if the package has been found defective during inspection, is scrapped.

All of the processes performed by the needle-suture assembly and packaging system of the instant invention are under control of a control system computer 99 as shown in FIG. 1. Alternatively, the control system may be implemented in a plurality of programmable logic controllers or other such suitable control devices (not shown).

To begin, the control system 99 initiates power up of the various devices utilized in the automatic needle-suture assembly and packaging system. At this point, an operator may be prompted to set up the dies for the swaging assembly that correspond to the size of the batch of needles to be processed. Additionally, any other necessary adjustments and setups may be performed for each assembly, for e.g., to initialize the Adept® robot assembly at the needle sorting station 100, or, the needle supporting blade of the load cell in the automatic pull-test station 300. Also as part of the power up display, an operator may be prompted to choose between operating the system in the normal, fully automatic mode, or, in a single step mode for diagnostic and troubleshooting purposes.

FIGS. 3(*a*)–3(*d*) are block diagrams generally illustrating the automatic needle-suture assembly and packaging system 10 of the instant invention. For instance, at the needle sorting apparatus 100, needles are first loaded into a vibratory bowl at step 11, automatically sorted and linearly fed at step 12 to a translucent indexing conveyor at step 13, evaluated with respect to orientation and position by a vision tracking system at step 14, picked up by a robot apparatus at step 15, transferred to a precision conveyor by the robot apparatus at step 16, and finally conveyed to a load station where the needles are transferred to a multi-axis gripper located on a rotary swage dial 150 for subsequent transfer to the swaging station 200 indicated at step 17. A detailed explanation of the apparatus used to carry out each step will be explained in further detail hereinbelow.

Simultaneous with the needle sorting process described above with respect to steps 11 through 17, an automatic suture cutting and swaging process is taking place at the swaging station 200 shown in FIGS. 3(*a*) and 3(*b*) with respect to steps 19 through 30. Indefinite length suture material is supplied in various spools and configurations that may carry up to 5000 yards of material. This is indicated at step 19 in FIG. 3(*a*). Next, at step 20, the suture material is loaded into a payoff assembly which is part of a drawing tower apparatus to be described in detail below. This payoff assembly includes grippers that alternately draw the suture material from the spool to enable cutting thereof. When larger spools of material are used, the material may be optionally loaded in a driven spool feed assembly with a dancer as indicated at optional step 21 to ensure that the material does not break or snap when in tension.

While the material is being drawn, it may require extra treatment or processing. For instance, as described in detail below, it may be desirable to heat the suture material under tension at the suture tip in order to stiffen the material to facilitate the positioning thereof within the suture receiving opening of a surgical needle. Thus, at optional step 22, heat may be applied to a portion of suture material. At step 23 of the block diagram of FIG. 3(*a*), the suture material is gripped by the servo grippers. At step 24, the suture strand is drawn up the tower and positioned for insertion within the suture receiving opening of the needle for swaging.

After a surgical needle is indexed to the swaging station 200 as described above, the multi-axis gripper positions the needle in a precisely oriented position at the swage die opening formed at the ends of two swaging dies of a swage assembly as indicated as step 26 in FIG. 3(*b*). Simultaneously, the suture strand is drawn from a king spool along a single axis of a drawing tower to register a tip thereof for insertion within the suture receiving end of the needle. Next, at step 27, the gripper assembly at the drawing tower inserts the tip of the suture strand within a lower funnel guide for accurate positioning within the suture receiving opening of the needle that is aligned with the suture drawing axis. Then, at step 28, the multi-axis gripper releases its grip on the needle placed within the swage die opening. At step 29, the swage cylinder is activated to automatically swage the suture to the needle and to cut the indefinite length of suture strand at a predetermined length. While retaining the armed needle, the multi-axis gripper is then retracted at its station on the rotary swage dial as shown as step 30 and indexed to a pull-test station 300 at step 31 so that minimum pull-testing at step 32 or destructive pull-testing at step 33 may be performed.

Depending upon the results of the minimum pull-test, the armed needle will either be indexed by the rotary swage dial to the discharge station 400 where the armed needle will be discharged to the suture winding and packaging turret 500 if the pull-test requirements are met (as shown as step 34*a* in FIG. 3(*b*)), or, will be discharged at the pull-test station if the needle fails the minimum pull-test (as shown as step 34*b* in FIG. 3(*b*)). The destructive pull-test always renders the armed needle incapable of further processing so the needle is automatically discharged at the pull-test station 400 as indicated at step 35 in FIG. 3(*b*).

As indicated in FIG. 3(*c*), while the needle-suture assembly processes are being performed at the rotary swage dial, the automatic packaging processes are taking place about the suture wind and packaging turret 500. As indicated as step 40 in FIG. 3(*c*), at the package load station 400, an empty package tray is positioned on a tool nest located on the rotary suture winding turret 500. At step 43, the empty package tray is indexed to an optional package detect station 450 for checking the presence of the loaded empty package. Next, at step 45, the empty package tray is indexed to the needle-suture load to package station 600. As will be explained in detail below, the empty package tray support is engageable with an elevator assembly that successively registers the package tray for sequential receipt of needles from the rotary swage dial, as indicated at step 51. Then, as shown as step 55 in FIG. 3(*c*), armed needles that have passed the minimum pull-test are conveyed to a needle-suture load to package station 600 where up to eight individual armed needles are loaded into the package. As shown as step 58 in FIG. 3(*c*), the package tray containing the armed needles are indexed to the optional needle check station 75 for detecting missing needles. The next few steps take place at the suture winding station 550 where the suture strands depending from the needles are first gathered into a bundle by a vacuum assembly as shown as step 61 in FIG. 3(*d*). Then, the package tray containing the armed needles is oriented at step 64 to facilitate cooperative engagement with the winding stylus at step 67 that is extended to position the gathered suture bundle within the peripheral channel of the package tray. Next, at step 70, the package tray is rotated so the gathered suture bundle is wound around the peripheral channel. Finally, at step 73, the package tray containing armed needles is indexed to an open station 625 which may be an optional manual inspection station. At the same time the package is indexed to the open station, a package cover (lid) is loaded onto a gripping device, as shown at step 77, for attachment to the package tray at the paper insert station 650. At step 80, the package tray is indexed to the paper insert station 650 where the gripping device places the package cover onto the package tray to form a completed package. Finally, as indicated at step 83 in FIG. 3(e), the completed package is indexed to the package removal station 700 where the package is either discharged for further processing, as shown in step 87, or, if the package is determined to be flawed, is discharged to a reject bin as shown at step 89.

Needle Sorting Station

The needle sorting station 100 sorts, singulates, and successively conveys individual and precisely oriented surgical needles to each of four multi-axis grippers indexed thereat by the rotary swage dial assembly 150, in the following manner:

At the needle sorting station 100 illustrated in FIG. 4, a batch of unoriented needles of uniform size are first loaded into vibratory bowls 101a,b, automatically sorted and linearly fed by singulating devices 102a,b to each of two translucent indexing conveyors 105a,b, evaluated with respect to orientation and position by a vision tracking system (not shown), picked up by either of two robotic apparatuses 106a,b, transferred to individual engagement devices (boats) 108 located on a precision conveyor 107 by each robot apparatus, and finally conveyed to the rotary swage dial assembly where the needles are transferred to a multi-axis gripper for subsequent transfer to the swaging station 200 as will be described in further detail below. A detailed explanation of the needle sorting apparatus 100 is explained in further detail in copending U.S. patent application Ser. No. 08/181,600, and a detailed explanation of the robotic control system utilized therein is described in copending U.S. patent application Ser. No. 08/181,624 both of which are assigned to the same assignee as the present invention, and incorporated by reference herein.

Rotary Swage Dial/Multi-axis Gripper

Figure 3A:
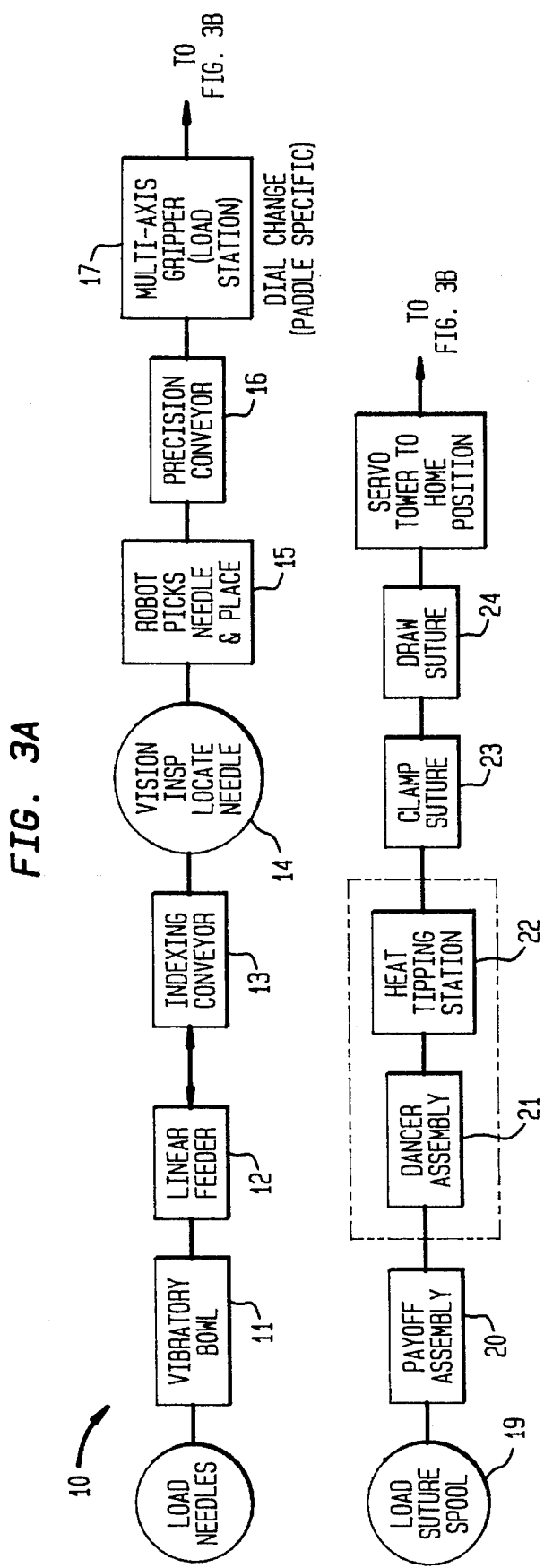
Figure 5:
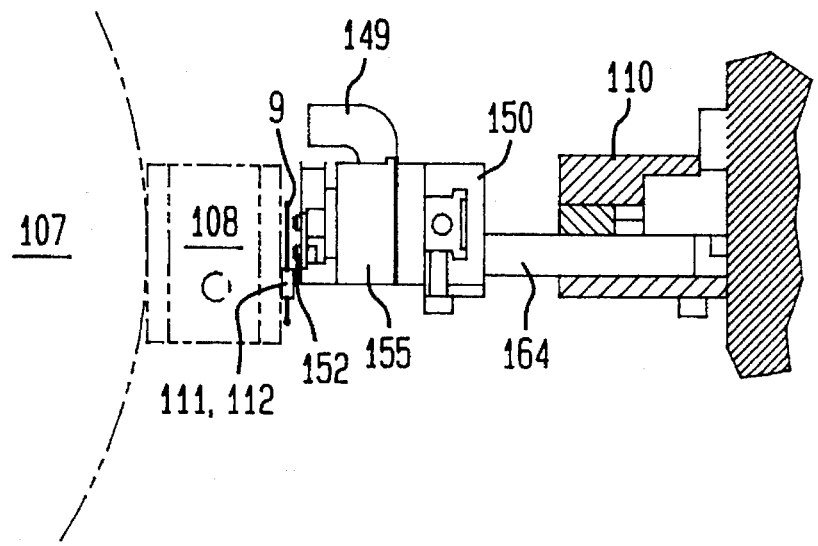
FIG. 5 illustrates the precision conveyor handing off surgical needle 9 to the retaining pin assembly of a multi-axis gripper 155.

As indicated at step 17 in FIG. 3(a), the next step of the needle threading and swaging process 10 involves the loading of the individual precisely oriented surgical needle 9 from the precision conveyor boat 108 onto the multi-axis gripper 155. At this point, the precision conveyor boat 108 is in a vertical position on conveyor 107 and carrying needle 9 in a precise orientation as shown in FIG. 5. As shown in FIG. 5, the needle 9 is delivered from the engagement jaws 111,112 of the conveyor boat 108 to the multi-axis gripper 155 that has been indexed to the needle sorting station 100 in opposed relation with the precision conveyor boat 108.

Figure 10A:
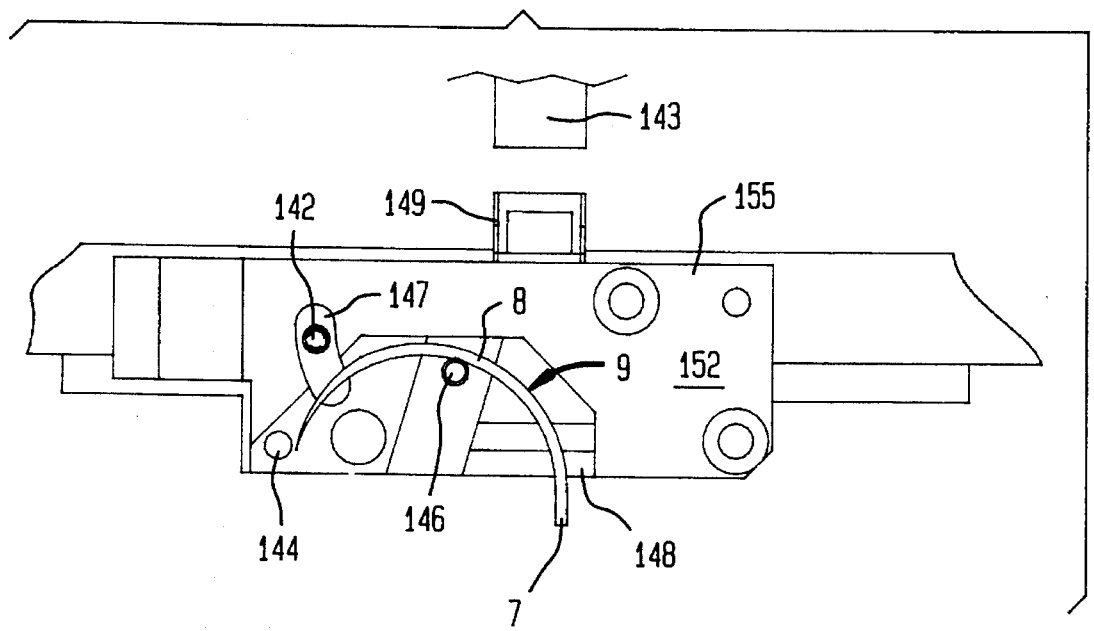
FIG. 10(a) is front view of the multi-axis gripper 155 showing pin 142 in a retracted position and a surgical needle 9 in a relaxed state.
Figure 10B:
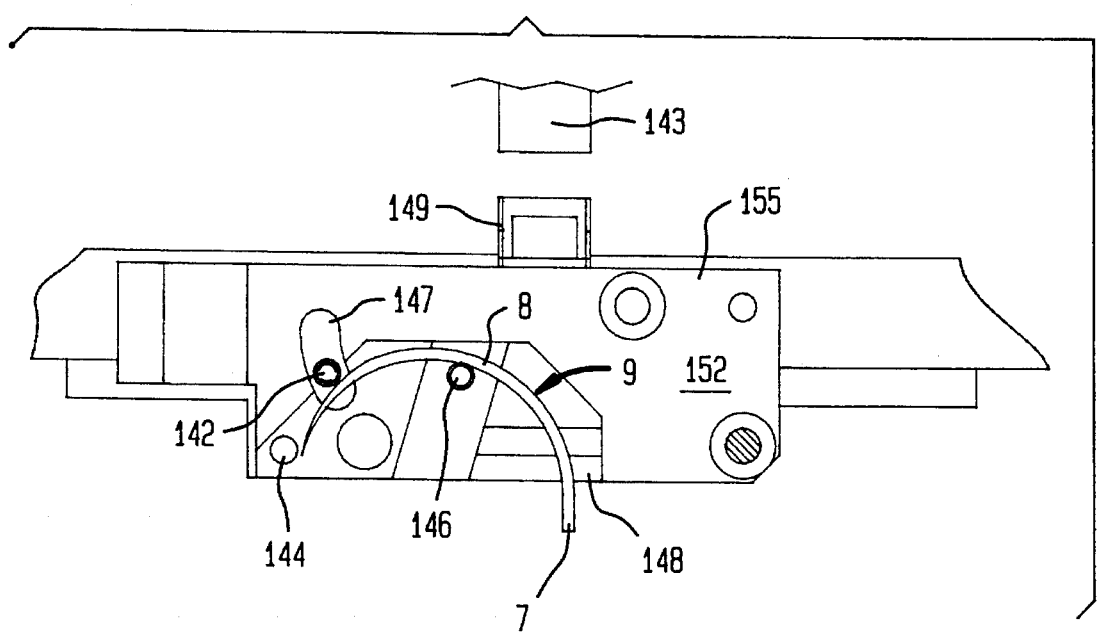
FIG. 10(b) is front view of the multi-axis gripper 155 showing a surgical needle 9 in an engaged position therein.

In the frontal view of the multi-axis gripper 155 as shown in FIG. 10(a), there is shown gripper pin assembly 152 comprising pins 142, 146, and 148 that extend perpendicularly therefrom to engage needle 9. Generally, to accomplish the transfer of the needle to a multi-axis gripper, the multi-axis gripper is extended from its retracted position upon the swage dial assembly 150 in the manner described below, so that pins 146 and 148 of the gripper pin assembly penetrate a plane formed by the curvature of needle 9 positioned upon the precision conveyor boat 108 as shown in FIG. 5. Then, the control system 99 initiates the command for a load solenoid or similar device to open engagement jaws 111,112 of the precision conveyor boat 108 to release the needle 9 so that it is deposited between the pins 146 and 148 of the multi-axis gripper 155. A front view of the multi-axis gripper 155 with needle 9 positioned thereon after transfer from the precision conveyor boat 108 is illustrated in FIG. 10(a). After the transfer, as controlled by the control system computer, pin 142 is actuated from a non-engaging position to an engaging position to thereby engage the needle 9 in an oriented position as shown in FIG. 10(b). The multi-axis gripper 155 is then retracted from its extended position and the swage dial assembly 150 is rotated to the swaging station 200 for automatic swaging of the suture to the needle 9.

FIG. 10(b) illustrates pins 142 and 144 located along the outer arcuate portion of the needle, while pin 146 supports the pin at the inner arcuate portion 8 of the needle 9. The barrel portion 7 of the needle 9 fits against a protruding stop 148 located on the gripper pin assembly 152 of the gripper 155 as shown in FIG. 10(b). The location of the stop 148 may be adjusted to accommodate the engagement of different size surgical needles. In the preferred embodiment, the gripper pin assembly 152 is replaceable with other gripper pin assemblies having the stop 148 positioned to accommodate different sized surgical needles. Note that in FIGS. 10(a) and 10(b), the suture receiving end portion 7 of needle 9 extends below the gripper pin assembly 152 of the multi-axis gripper 155. This enables placement of the suture receiving end 7 of the needle within the swage dies of the swaging assembly as will be explained below.

The three pin needle engagement configuration shown in FIGS. 10(a) and 10(b) ensures that needle 9 will not be displaced when the swage dial 150 is rotating, or, when the multi-axis gripper 155 is being retracted or extended. In the preferred embodiment, pin 142 is spring loaded and is retractable within guide 147 to release its grip of needle 9 when a needle is being transferred thereto or, when automatic swaging and pull-testing occurs. Retraction of pin 142 is activated by depressing plunger 149 by a suitable push rod or cam 143 as shown in the Figures. Pin 142 is biased back into the needle engaging position as shown in FIG. 10(b) by retracting the push rod or cam 143.

Figure 6:
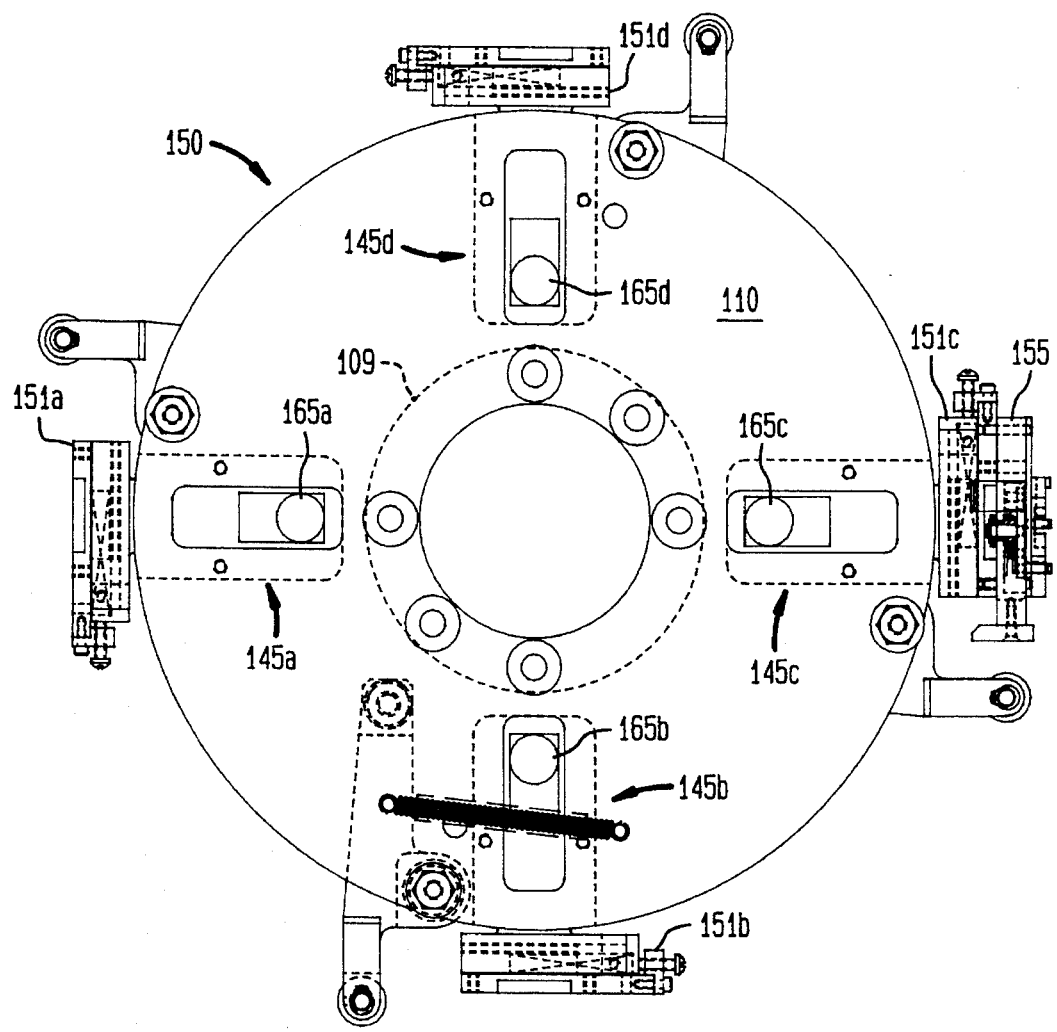
FIG. 6 is a top view of the rotary swage dial assembly 150 comprising a swage dial plate 110 having four multi-axis gripper stations 145a,b,c,d mounted thereon.

As illustrated in FIG. 1, the rotatable swage dial assembly 150 includes four multi-axis gripper stations where simultaneous needle operations are performed. In the detailed illustration of FIG. 6, the swage dial assembly 150 includes a swage plate 110 having four multi-axis gripper stations 145a, 145b, 145c, 145d spaced equally thereon. The swage plate 110 is rotatably mounted at a central hub 109 and operable to rotate under the control of a control system computer 99. In the preferred embodiment, a reciprocating carriage is provided at each multi-axis gripper station of the swage dial assembly 150. For instance, as shown in FIG. 6, multi-axis gripper station 145a includes reciprocating carriage 151a, while station 145b includes reciprocating carriage 151b, station 145c includes reciprocating carriage 151c, and station 145d includes reciprocating carriage 151d. Mounted to each reciprocating carriage 151a,b,c,d for retractable movement therewith, are multi-axis grippers, one of which 155 is shown connected to gripper mount 150c in FIG. 6.

Figure 7A:
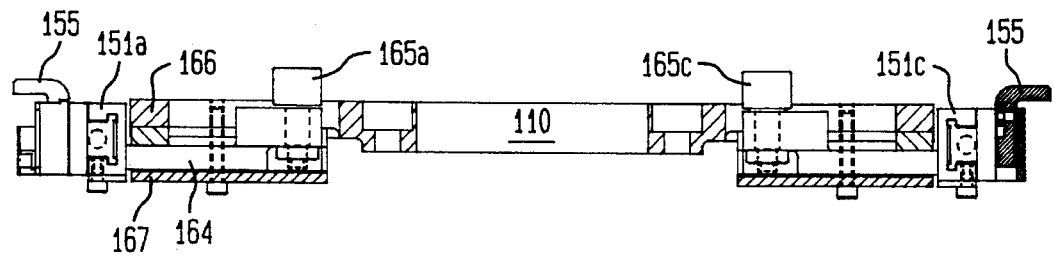
FIG. 7(a) is cross-sectional view of the four station swage dial assembly 150 showing multi-axis gripper 155 in a retracted position.
Figure 7B:
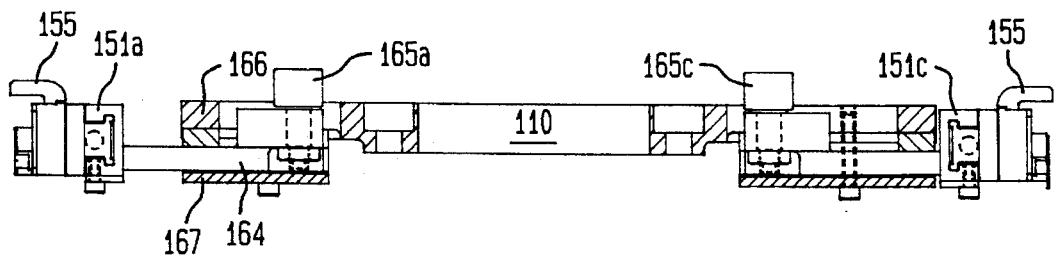
FIG. 7(b) is cross-sectional view of the four station swage dial assembly 150 showing multi-axis gripper 155 in an extended position.

As previously mentioned, each reciprocating carriage 151a,b,c,d and the multi-axis gripper 155 connected thereto is movable from a retracted position to an extended position. When the gripper 155 is in the retracted position shown in FIG. 7(a), the needle 9 may be conveyed to a different station as the swage dial rotates; when the gripper 155 is in the extended position as shown in FIG. 7(b), the needle is in one of the active stations, such as the automatic swaging station. The swaging station and the automatic pull-test station are both described in further detail in respective copending patent application Ser. No. 08/181,599 and Ser. No. 08/181,601 assigned to the same assignee of the present invention.

Figure 9:
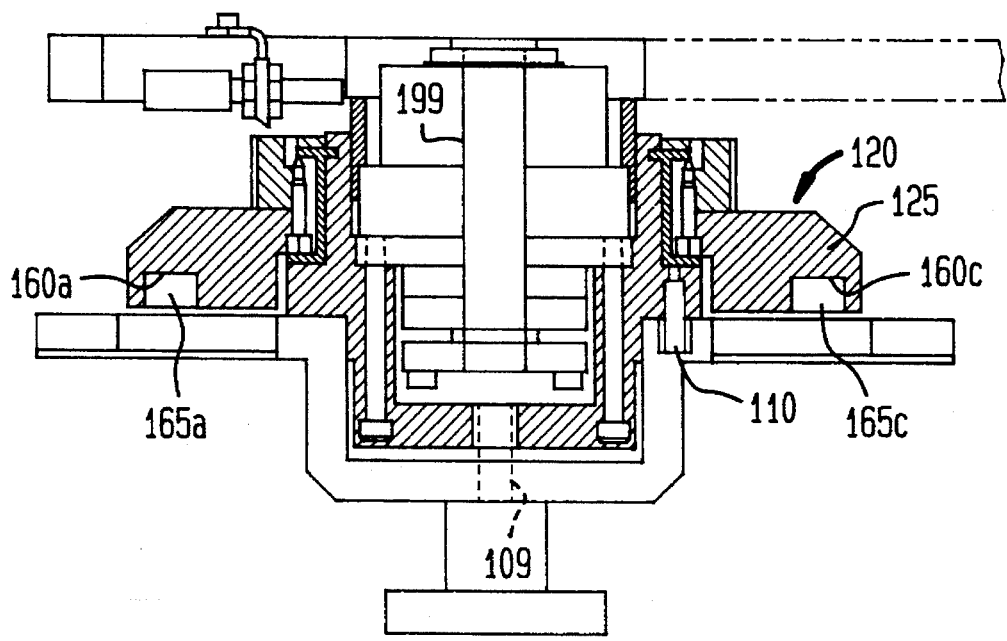
FIG. 9 is a cross-sectional view of the cam dial plate 125 mounted coaxial with the swage dial plate 110 for cooperative rotational movement thereof, and showing cam followers 165a and 165c positioned within their respective cam tracks 160a and 160c.
Figure 8A:
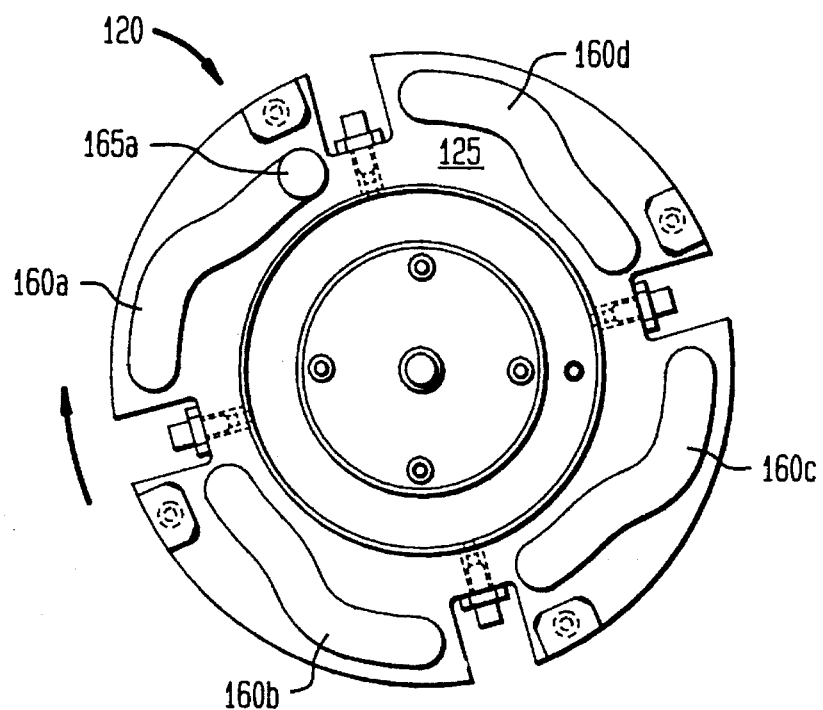

The process for extending the multi-axis grippers 155 for suture insertion will now be explained. As shown in FIGS. 7(a) and 7(b), each cam follower 165a(b,c,d) is mounted to a cam slide 164 at one end of the reciprocating carriage 151, and the multi-axis gripper 155 is connected to the cam slide 164 at the other end. Cam slide 164 is slidable within stationary guides 166,167 and is adapted for reciprocal movement when the cam follower 165 is actuated. In the preferred embodiment shown in FIG. 8(a), cam follower 165 is a roller that fits within cam tracks of a rotatable cam dial assembly 120. Cam dial assembly 120 is shown in FIG. 8(a) as comprising a cam dial plate 125 having four cam tracks 160a,b,c, and 160d which correspond to a multi-axis gripper stations 145a,b,c, and 145d, respectively. Each cam follower 165 is positioned within each respective cam track at each station for movement therein. For instance, as shown in FIG. 9, cam follower 165a is positioned within cam track 160a and cam follower 165c is positioned within cam track 160c. Also in FIG. 9, cam dial 125 is positioned above swage dial 110 and mounted coaxial therewith. The cam dial 125 is rotatable about a central shaft 199 and controlled by a separate rotary indexing transmission (not shown) so that it may rotate separately from the swage dial plate 110.

Figure 8B:
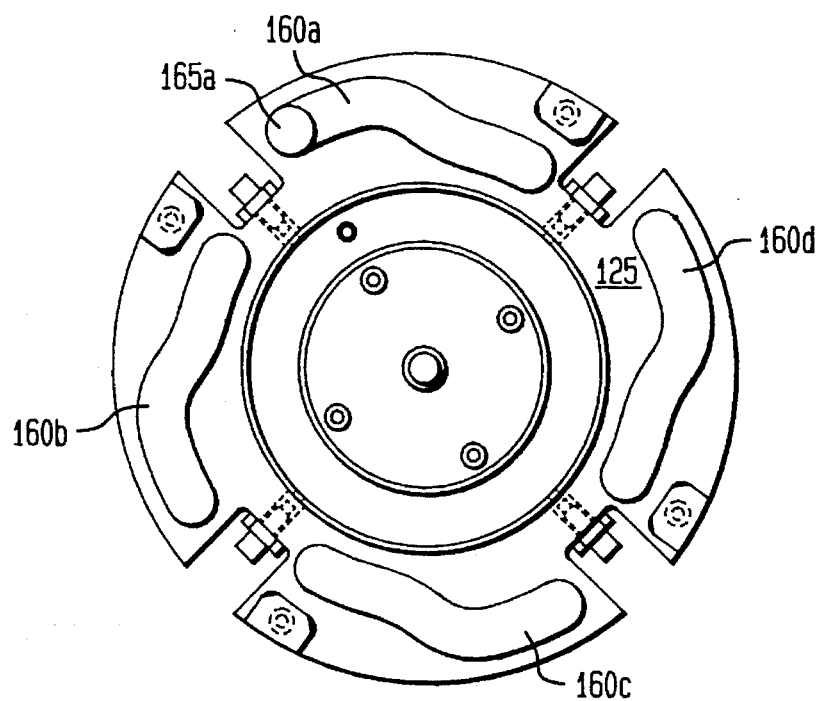

FIG. 8(a) shows cam follower 165a in a first retracted position within the cam track 160a. When in this position, reciprocating carriage and consequently multi-axis gripper 155 are in their retracted position as shown in FIG. 7(a) discussed above. To extend the multi-axis gripper 155 in place at its respective station, the cam dial plate 125 is rotated in the clockwise direction with respect to the swage dial plate 110, as indicated by the arrow in FIG. 8(a), for approximately 45–55 degrees, forcing cam follower 165a in its cam track 160a to move toward the periphery of the dial as shown in FIG. 8(b). Consequently, the cam slide 164, reciprocating carriage 151a, and the multi-axis gripper 155 move to the extended position as shown in FIG. 7(b) and discussed above. To move back to its retracted position, the cam dial plate 125 is rotated in the counter clockwise direction with respect to the swage dial plate 110 for approximately 45–55 degrees, forcing cam follower 165a in its respective cam track 160a to move back to its retracted position (FIG. 8(a)). Consequently, the cam slide 164, reciprocating carriage 151a, and the multi-axis gripper 155 move to the retracted position as shown in FIG. 7(a) and discussed above.

It should be understood that when cam dial plate 125 rotates with respect to swage dial 110, each multi-axis gripper 155 is either extended or retracted in its respective cam track. Thus, the system is designed so that all processes performed at each station occur simultaneously and for approximately the same duration of time when the multi-axis grippers are in their extended position, for e.g., for needle pick-up, for needle swaging, or, for needle pull-testing. The timing of the system is operated under the control system, a detailed description of which can be found in copending patent application Ser. No. 08/181,607, assigned to the same assignee of the present invention.

When the multi-axis gripper 155 is retracted, the needle engaged thereby may then be indexed to a different station for further processing. To index the needle to another station, both swage dial plate 110 and cam dial plate 125 are rotated together for approximately 90 degrees to position each multi-axis gripper at the next station. For example, when the cam dial plate 125 and the swage dial plate 110 are simultaneously rotated 90 degrees counterclockwise in FIG. 1, the gripper 155 that had received the needle at station 100 is now indexed to the position corresponding to station 200 for swaging a suture thereto. Similarly, after swaging, the cam dial plate 125 and the swage dial plate 110 are simultaneously rotated counterclockwise so that the armed needle at station 200 is indexed to the pull testing station 300 for pull-testing thereof. The operations performed concurrently at each station about the swage dial increases throughput to provide an output of pull-tested armed surgical needles at a rate of approximately 60 per minute in the preferred embodiment.

Automatic Swaging Station

As previously mentioned, the automatic swaging station 200 of the needle threading and swaging system 10 is where the suture of indefinite length is drawn, cut, and inserted within the suture receiving end of a surgical needle for swaging thereof.

Figure 11:
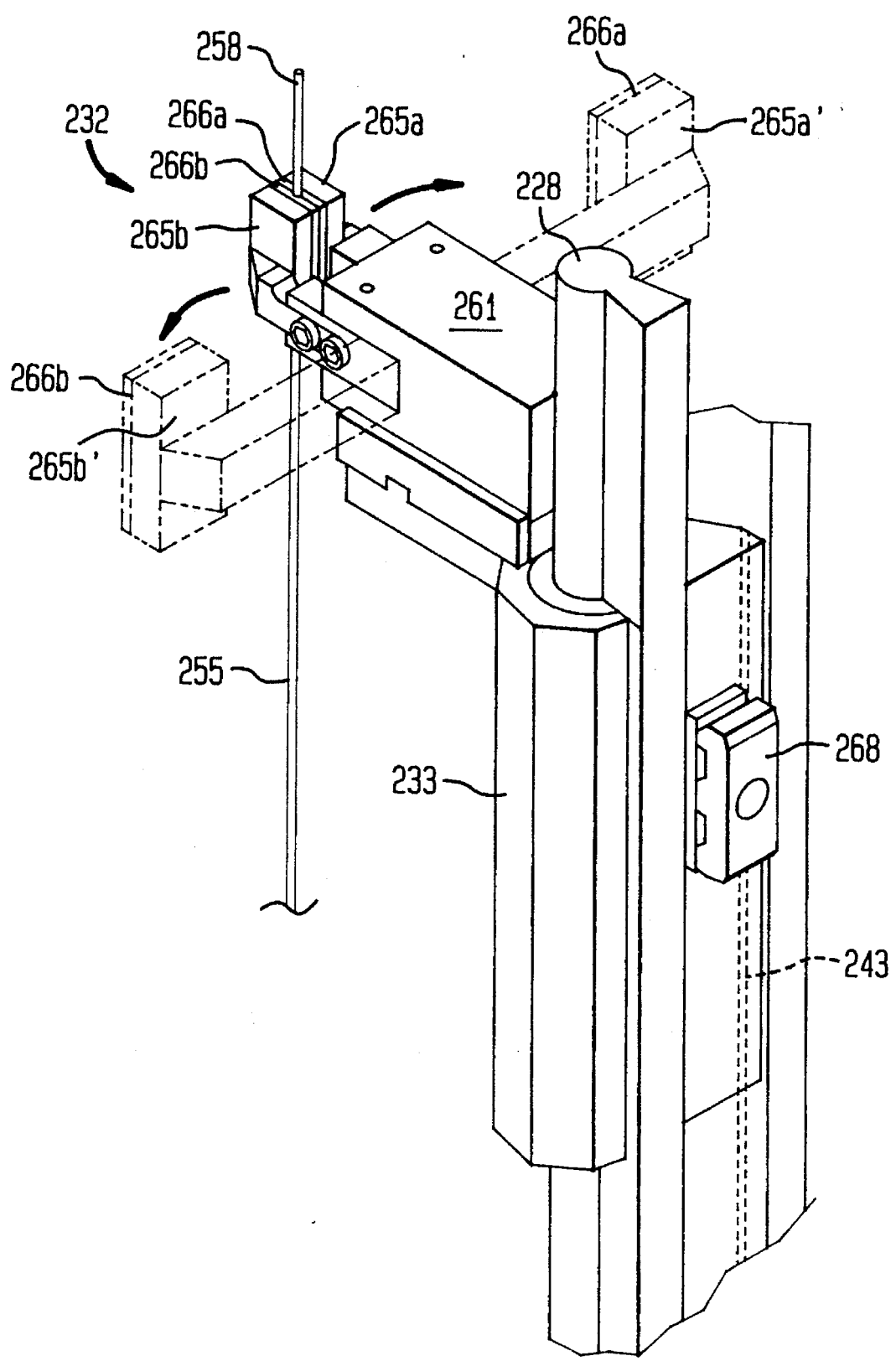
FIG. 11 is an enlarged view of a gripper assembly having gripper arms 265a,265b shown in their closed (suture gripping) and open positions.

At step 19 of FIG. 3(a) the indefinite length of suture material is loaded at one end of the payoff assembly. In the preferred embodiment, the payoff assembly is embodied as a drawing tower 220 shown in FIG. 12(a). The drawing tower 220 comprises left side rail 222 and right side rail 224 both mounted on suitable mounting block 225 and defining a drawing bed for drawing an indefinite length of suture material along a drawing axis therebetween. Located parallel to the left and right side rails 222,224 and suitably connected thereto are respective left guide rod 226 and right guide rod 228. The first gripper means or right gripper 232 reciprocates up and down along right guide rod 228 while the second gripper means or left gripper 230 reciprocates up and down the left guide rod 226. Each of the grippers 230,232 grip the suture material that is fed from a spool through pulley 235 located at the bottom of the drawing tower 220, and carries the material to the upper end of the tower. The right gripper 232 is mounted on right gripper carrier 233 for vertical movement along right guide rod 228, and the left gripper 230 is mounted on left gripper carrier 231 for vertical movement along left guide rod 226 as shown in FIG. 12(a). FIG. 11 illustrates a gripper 232 (and 230) having a gripper arm drive 261 that is pneumatically operated to drive pair of retractable gripper arms 265a, 265b toward each other to a suture gripping position, or, away from each other to an open position. Each retractable gripper arm is provided with a non-metallic pad 266a, 266b for gripping the suture material 255 at a free end thereof when actuated to the gripping position. To release the grip of the suture, gripper arms 265a,265b are retracted approximately 180 degrees apart in the direction indicated by the arrows of FIG. 11 to the open position. When in the open position the gripper arms 265a', 265b' do not interfere with the motion of the other vertically moving gripper as it reciprocates along the respective left or right rod, nor will it interfere with the cutter assembly 280 that cuts the strand to a predetermined length as will be explained below in view of FIG. 14. The retractable nature of the grippers and of the cutting assembly enables single drawing axis operation.

As mentioned above, each gripper carrier and gripper thereof is designed to advance vertically along the respective left and right rods. As shown in FIG. 12(a), the right gripper 232 and gripper carrier 233 is driven by right servo motor 238 which is mounted to the right side rail 224 by right motor mounting bracket 239. Similarly, the left gripper 230 and gripper carrier 231 0 is driven by left servo motor 236 which is mounted to the left side rail 222 by left motor mounting bracket 237. In the preferred embodiment, both left and right servo motors are interfaced with and controlled by the control system computer 99. As shown in FIG. 12(a), right servo motor 238 drives timing belt 243 which consequently enables vertical positioning of right gripper carrier 233 along right rod 228, while the left servo motor 236 drives timing belt 241 which consequently enables vertical positioning of left gripper carrier 231 along left rod 226. As FIG. 11 illustrates, timing belt 243 is clamped to its respective gripper carrier 233 by a timing belt clamp 268 located on the back of the gripper carrier. A similar timing belt clamp (not shown) is provided on gripper carrier 231 for clamping timing belt 241 to enable vertical movement of gripper 230. FIG. 12(a) shows timing belt 241 engaging upper left pulley 245 and lower left pulley 246 as well as idler pulleys 247,248 which are part of tensioner block 244 that adjusts the tension of the timing belt 241 and consequently of left gripper carrier 231. Likewise, FIG. 12(a) shows timing belt 243 engaging upper right pulley 251 and lower left pulley 252 as well as idler pulleys 253,254 which are part of tensioner block 245 that adjusts the tension of the timing belt 243 and consequently of right gripper carrier 233.

FIG. 12(a) shows the tip and cut carrier 180 positioned along shafts 204 and 205 which are located parallel to respective left and right rods 226,228. Tip and cut carrier 180 provides the support for tipping assembly 290 that applies heat to a specific location of the suture material, and also provides support for the cutter assembly 280 that cuts the suture material. In the preferred embodiment, vertical movement of the tip and cut carrier 180 is accomplished by cranking handwheel 208 shown in FIG. 12(b). Other embodiments may implement a computer controlled servo motor to vertically register the tip and cut carrier 180 prior to cutting the material.

As illustrated in FIG. 12(b), cranking handwheel 208 actuates a gearbox 213 that rotates chain drive sprocket 214. The gearbox 213 is mounted on a gearbox mounting bracket 122 which, in turn, is mounted to frame member 299. A cable chain 215 is engaged with chain drive sprocket 214 to actuate movement of the tip and cut carrier 180 as shown in FIG. 12(b). The cable chain 215 also engages chain idler sprockets 218 and 219 which are rotatably mounted to upper tensioner pulley bracket 221 and lower tensioner pulley bracket 223, respectively. The vertical positioning of tensioner pulley brackets 221,223 may be adjusted to vary the slack in cable chain 215. Cable chain 215 also engages chain idler sprockets 227 and 229 which are suitably mounted on left side rail 222. As shown in FIG. 12(a), the back 211 of tip and cut carrier 180 is clamped to cable chain 215.

Both the stroke of the grippers 230,232 and the positioning of the tip and cut carrier 180 along drawing tower 220 dictates the length of the material that will be cut. For instance, as shown in FIG. 12(a), proximity sensors 273, 274, and 275 are positioned vertically at different heights along the drawing tower 220 to enable predetermination of the length of suture material to be cut. Specifically, the locations of the proximity sensors 273,274, and 275 sense the positioning of the tip and cut assembly 180 as controlled by handcrank 208 in order to notify the control system 99 to change the reciprocating travel of grippers 230,232. Also as shown in FIG. 12(a), proximity sensor 270 is mounted at a position along the right side rail 224 to verify that right gripper 232 has reached a desired position at the upper end of the tower 220 and notify the control system 99 accordingly. Likewise, a proximity sensor (not shown) is mounted at the desired height along the left side rail 222 to verify that left gripper 230 has reached its desired position at the upper end of the drawing tower 220.

Figure 13:
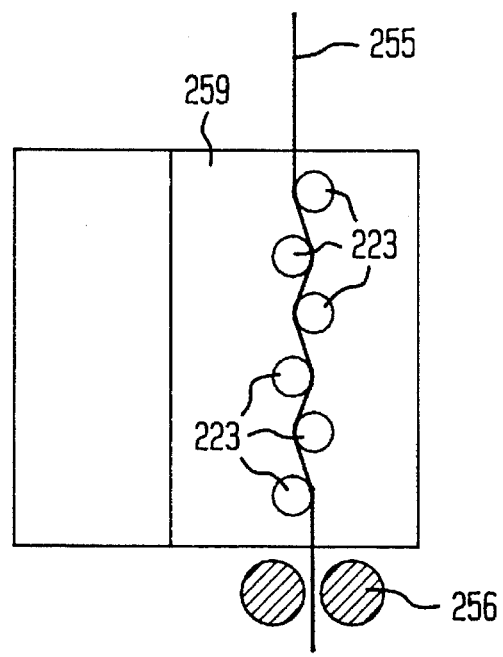
FIG. 13 is a detailed view of the tensioner assembly 59 for increasing or decreasing suture strand tension as desired.

To feed the indefinite length suture material up the length of the drawing tower, the suture material 255 is first manually threaded through eyelet 256 and through optional knot detector 257 which senses any sudden change in the thickness of the suture material as shown in FIG. 13. Detection of a knot in suture material 255 will trigger the control system 99 to discard the cut strand of material at a subsequent operation. Additionally, the suture material may be threaded within a tensioning (or dancer) assembly 259 which comprises a plurality of vertically spaced apart cones 223 each of which may be positioned laterally to increase or decrease the tension of the suture strand 255 as shown generally in FIG. 13.

The suture material 255 is then advanced over pulleys 235a and 235b located at the bottom of the drawing tower 220, and around pulley 212 which is mounted on the lower portion of tip and cut carrier 180 that is illustrated near the center of the tower as shown in FIG. 12(a). Note that the lower threading pulley 235b, guide pulley 212, left gripper 230 and right gripper 232 are vertically aligned so that the cutter assembly 280 will always cut horizontally across the strand of material as will be discussed in detail below.

Under the control of the control system computer 99, the right servo motor 238 is enabled to drive the lead (right) gripper vertically along right rod 228 to register the tip of the indefinite length suture strand 255 for positioning within the suture receiving opening 7 of a precisely oriented surgical needle shown engaged by the multi-axis gripper 155 at the swaging assembly 390 located at the top of the drawing tower 220 as shown in FIG. 12(a). To accomplish this, the lead gripper servomotor advances the lead gripper for a long stroke distance, which may range from 12 inches to 36 inches depending upon the length of said suture strand desired, but is 16.1 inches in the preferred embodiment. The long stroke moves gripper 232 from a home position just above the tip and cut carrier 180 and below the cutter assembly 280, to the position slightly below swaging assembly 390 as shown in FIG. 12(a).

Simultaneous with the positioning of the lead gripper 232 during the long stroke, the other servomotor, for e.g., servomotor 236, positions the bottom gripper, for e.g., left gripper 230, along left rod 226 at the home position preferably above the tip and cut carrier 180 and below the position of the cutter assembly 280 as shown in FIG. 12(a). It is understood that the lead gripper is gripping the material 255 at all times during the long stroke, while the bottom gripper is in its open position and not gripping. The process of advancing suture material 255 by alternating grippers at each cycle eliminates the recycle or return time for retaining the gripper to the original position. This makes faster machine speeds and hence, higher production rates possible.

To insert the tipped end 258 of the suture material within the suture receiving end 7 of surgical needle 9, the lead gripper 232 again advances the suture material 255 for a short stroke distance of about 1.9 inches, so that the tipped end 258 will advance precisely within the suture receiving opening 7 of needle 9 for a swaging operation to take place at the swaging assembly 390.

As the tipped end 258 of the suture material is advanced during the short stroke distance, a portion of the material 255 that has been heated by tipping assembly 290, (explained hereinbelow), advances vertically to a position just above the home position of the left gripper 230 and adjacent the cutter assembly 280. Then, as automatic swaging of the tipped end 258 to the surgical needle occurs, the left gripper 230 (lower gripper) is actuated to grip the material 255 at or below the tipped portion 278 i.e., the portion of the suture material heated by tipping assembly 290 as shown in FIG. 12(a), and the cutter assembly 280 is actuated to cut the tipped portion 278 of the suture material 255 so that the left gripper 230 is now gripping an indefinite length suture strand 255 having a tipped end 258. Simultaneous with the engagement of left or bottom gripper 230, the top or right gripper 232 is actuated to release its grip on the definite length suture material.

Heater Assembly

Figure 18:
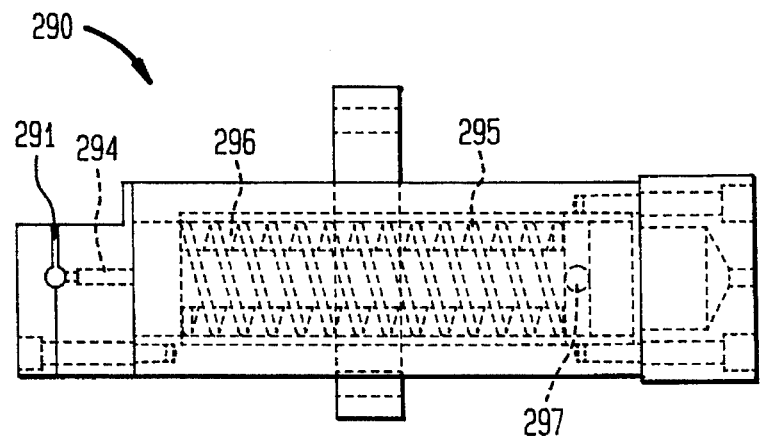
FIG. 18 is a detailed top view of the tipping assembly 290 for heating a portion of the suture material.

Immediately after advancing the long stroke distance and prior to advancing the short-stroke distance, the top gripper is temporarily halted so that a portion of the suture material 255 may be heated (tipped). Heating of the suture under tension and the subsequent cooling thereof will stiffen the material and aid in the positioning and subsequent swaging of the tip of the material within the confines of the surgical needle. The operation of the tipping assembly 290 mounted on tip and cut carrier 180 will now be explained as follows:

As shown in FIG. 18, the tipping assembly 290 is essentially an oven comprising a heat exchanger unit 295 that heats the air in the heater cavity 296. When a pulse of incoming air is provided to the heat exchanger input 297, the heated air is displaced and it provides a pulse of heated air to a vertical cylindrical cavity 291 as shown in FIG. 12(a). As shown in FIG. 18 the heated air is forced through horizontal orifice 294 for a predetermined duration so that the length of suture material 255 suspended in tension through vertical cavity 291 will be heated. The control system computer 99 controls the duration of the heat pulse so that the material is adequately heated and will have sufficient time to cool before the cutting operation. Preferably, the temperature of the heated pulse may vary depending upon the surface area of the strand suspended through the vertical cavity 291. Preferably, the tipping assembly 290 is positioned slightly below the bottom or left gripper 230. As mentioned above, this is required so that when the suture material 255 is advanced the short stroke distance, the tipped portion 278 of material 255 will advance a corresponding distance so that it may be cut by cutter assembly 280. This ensures that the bottom gripper, e.g., left gripper 230, will grip the material having a new tipped end 258 for the next suture draw/insert cycle.

It should be understood that various other "tipping" technologies will work depending upon the type of suture material that is being processed. For instance, when VIC- RYL® and VICRYL®-like suture materials are used, tensioning of the strand, in addition to hot air application to a strand will enable the surface thereof to be melt and recast to form a stiffened tip. The application of tension in addition to a heated, grooved, die for forming the tip diameter of VICRYL® suture materials may also be used; however, the use of a die to form the tip diameter, requires closer control of the strand location to ensure that a tip gets into the die groove for every cycle. For wax-impregnated suture materials like silk, the application of tension only at predetermined locations, will form a stiffened portion of the suture strand at those locations. Another tipping method for use with braided suture materials, involves applying and penetrating the braid with a dilute resin material such as General Electric's VITEL® having a high solvent content, and quick drying the applied portions with hot air while maintaining tension of the suture strand materials to form a stiffened tip thereof.

Cutter Assembly

Figure 16:
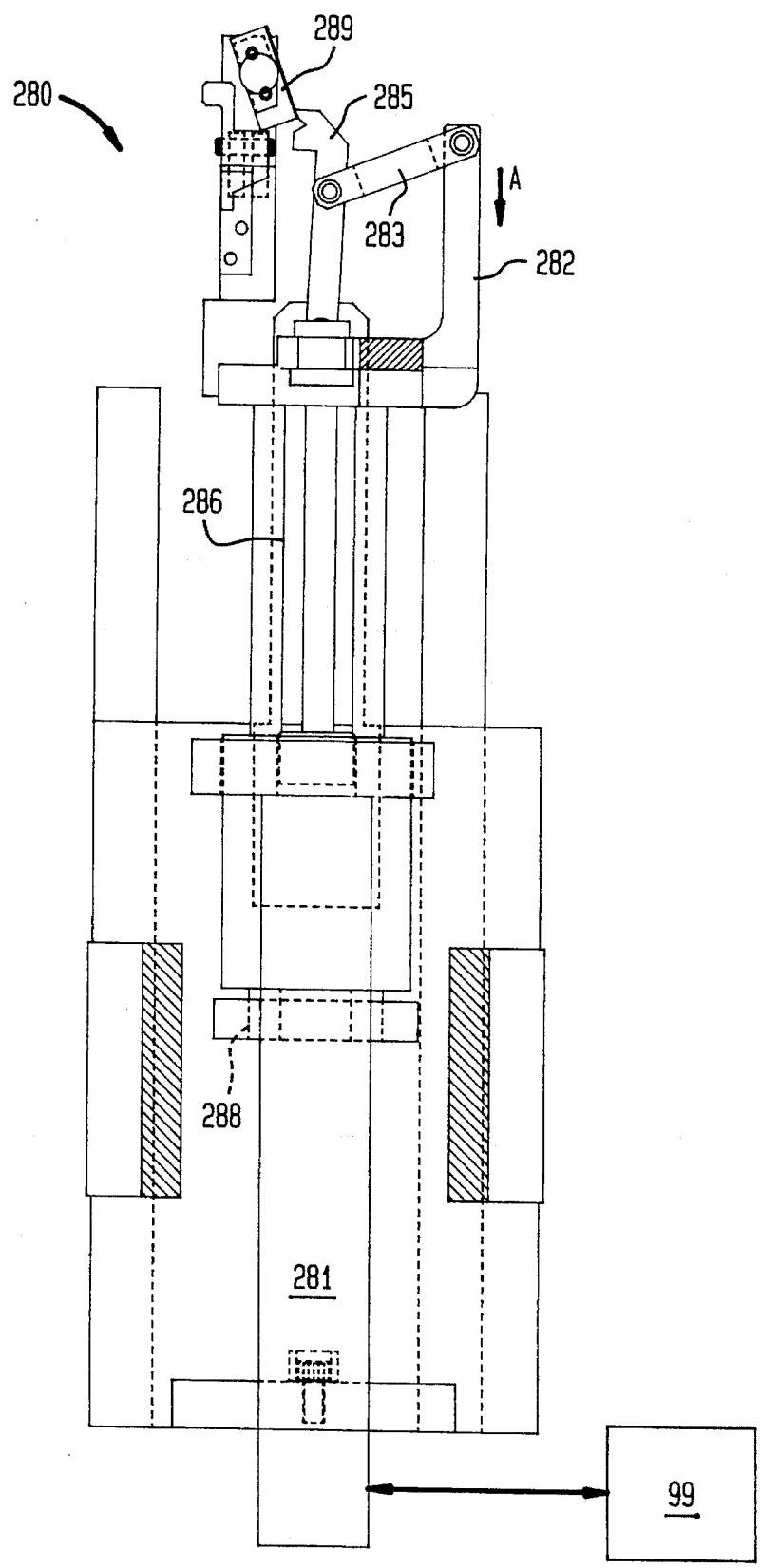
FIG. 16 is a detailed top view of the cutter assembly 280 in the instant invention.
Figure 17A:
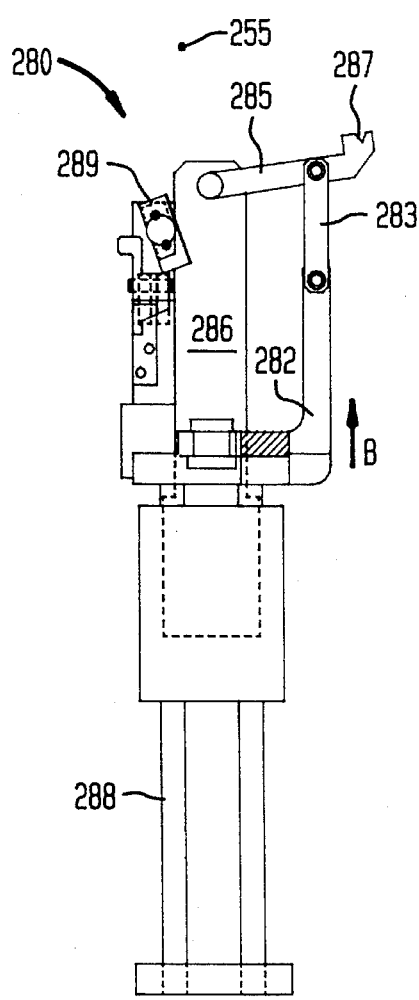
FIG. 17(a) is a detailed top view of the cutter assembly 280 shown in a fully retracted position.
Figure 17B:
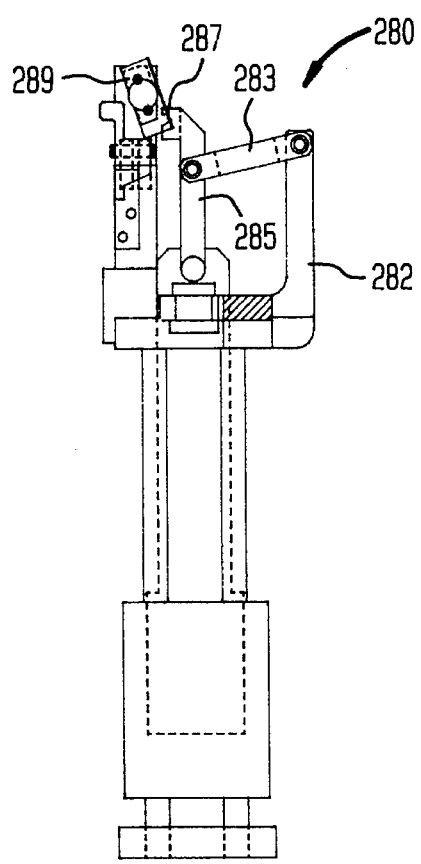
FIG. 17(b) is a detailed top view of the cutter assembly 280 shown in a fully extended (cutting) position.
Figure 24:
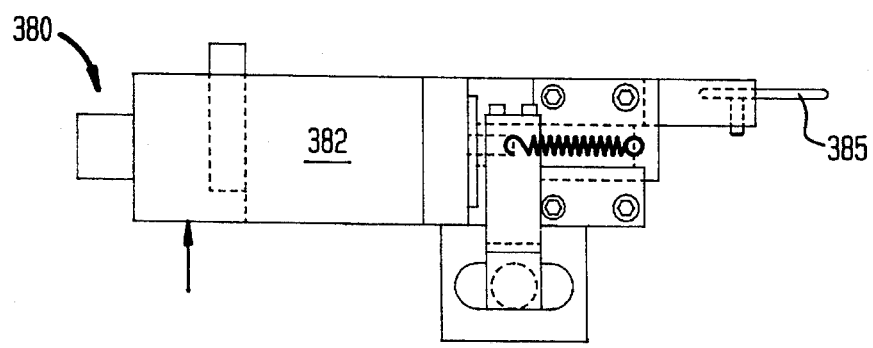
FIG. 24 is a detailed view of the needle stripper assembly 380 for removing the needle 9 after a destructive pull-test or after minimum pull-test failure.

FIGS. 16–17(b) illustrate in detail the cutter assembly 280 which is suitably mounted to the tip and cut assembly 180 as shown in FIG. 12(a). As shown in FIG. 16, the cutter assembly comprises overcenter linkage 282 having a link arm 283 pivotally connected at one end thereof. A pivotal locator arm 285 is fixedly connected to link arm 283 at a second end thereof and is illustrated in FIG. 24 as substantially transverse thereto. The other end of locator arm 285 is pivotally connected to a stationary guide mechanism 286. Note, that all pivotal linkages described herein are simple pin linkages, the actuation of which creates the dwell moment for cutting the suture strand and obviates the need for complicated cam, slots, and sliding mechanisms.

As shown in FIG. 17(a), the stationary guide 286 is located in a plane perpendicular to the drawing axis of the suspended strand of material 255, and is located a distance from the strand approximately equivalent to the length of locator arm 285. In addition, overcenter linkage 282, locator arm 285, and cutting blade 289 all lie in planes perpendicular to the drawing axis of the strand of material 255.

A retractable ball slide 288 is mounted on the stationary guide 286 and coupled to overcenter linkage 282 for moving the overcenter linkage and blade 289 along the stationary guide 286 in the direction indicated by arrow "A" in FIG. 16 from a cutting position to a retracted position shown in FIG. 17(a). As the ball slide 288 moves overcenter linkage 282 to a retracted position, the locator arm 285 is pivoted away from the strand 255 and the blade 289 is retracted. Thus, when the cutter assembly 280 is in the retracted position prior to cutting of the strand and immediately thereafter, the blade 289 and locator arm 285 do not interfere with the reciprocating motion of the grippers 232,230 along the drawing tower 220, nor do they come in contact with the suspended strand 255. In the preferred embodiment, pneumatic air cylinder 281 enables reciprocating movement of the ball slide 288 along stationary guide 286 as shown in FIG. 16.

When cutting the strand of material 255, the retractable ball slide 288 reciprocates in the direction toward the strand 255 indicated by arrow "B" in FIG. 17(a) to bring the overcenter linkage 282, cutting blade 289 and locator arm 285 to the cutting position shown in FIG. 17(b). As the overcenter linkage 282 moves to the cutting position, the link arm 283 translates the movement of the ball slide 288 into pivotal movement of the locator arm 285. Locator arm 285 is provided with a V-shaped support notch 287 which functions to engage and position the strand of material 255 to be cut as the arm is pivoted into the cutting position. The V-shaped notch also functions to support the strand on two sides of the strand 55 while it is being horizontally cut on a third side. This enables clean, broom-free cuts especially of multi-filament suture material, which has a tendency to form a broom end when the strand is under tension and is cut by scissors, or, when the multi-filament strand is sliced and otherwise, not properly supported.

The cutting blade 289 of cutter assembly 280 is fixedly mounted to reciprocating ball slide 288 at a slight angle relative thereto and in a plane parallel with that of the locator arm 285. In the preferred embodiment, a single action by the pneumatic air cylinder 281 will enable movement of the reciprocating ball slide 288 along stationary guide 286. This consequently enables pivoting of locator arm 285 from its retracted position (FIG. 17(*a*)), so that V-shaped notch 287 supports the strand 255 at two sides thereof while a third side of the strand bears upon the cutting edge of blade 289 as the blade moves towards the supported strand 255 traversing the drawing axis thereof. Thus, the strand 255 is cut in a dwell moment of the locator arm after the locator arm 285 has pivoted in the direction toward the blade 289 to the cutting position shown in FIG. 17(*b*). The blade 289 slices the strand of material while it is held stationary by locator arm 285 by virtue of the angled orientation of the blade with respect to the axis of reciprocation illustrated in FIGS. 17(*a*) and 17(*b*). In the preferred embodiment, the slice ratio is 1:1, with the blade 289 angled at approximately 45 degrees relative to the axis of reciprocation, so that the strand 255 is cut an amount equivalent to the distance the blade 289 traverses the drawing axis.

Swaging Assembly

The swaging operation taking place at the swaging station will now be described. FIGS. 14(*a*)–14(*g*) illustrate the multi-axis needle gripper 155 and swaging and suture alignment dies shown in various stages of the suture insertion and needle swaging sequence. This sequence, and the interaction of the dies in relation to each other, the needle, and the insertion of the suture, accomplish the insert and swage function with minimal parts and simple motions.

After conveying the needle to swaging assembly 390 shown in FIGS. 12 and 13(*a*), the multi-axis gripper 155 is radially extended from the swage dial in the manner described above to position the suture receiving end 7 of needle 9 between the funnel shaped die opening formed at the ends of two swage dies 361,369 as shown in FIG. 14(*a*) and the partial perspective view of FIG. 14(*b*). As will be explained, swage die 361 is fixed in position and swage die 369 is movable laterally toward the fixed swage die 361, as indicated by the arrow, to accomplish swaging of the suture receiving end of a needle placed therebetween. A funnel shaped die opening 392 having an exit diameter slightly larger than the diameter of the suture receiving end 7 of the needle is formed when the two swage dies 361,363 are positioned adjacent each other as shown in FIGS. 14(*e*) through 14(*f*). In the preferred embodiment shown in FIGS. 19(*a*) and 19(*b*), the ends of each of the swage dies 361,369 are provided with recesses 321,322 respectively, so that the metal deformation that occurs as a result of the swaging of the needle 9, does not result in metal flash or spurs at the suture receiving end 7 of the needle. Note that different sets of swage dies may be provided, depending upon the size (diameters) of the needles and sutures to be swaged.

To precisely position the suture receiving end 7 of needle 9 between the swage die opening 392 formed at the ends of two swaging dies 361,369, the movable swage die 369 is temporarily moved apart. In the illustration of the swaging assembly 390 shown in FIG. 15(*a*), swage die 369 is moved apart from the fixed swage die 361 by actuating air cylinder 395 to provide a force upon cylinder rod 393 to enable swage die operating lever 397 to pivot about screw 394 and pull movable swage die 368 a predetermined distance away from the fixed swage die 361. In the preferred embodiment, lever 397 is biased by spring 364 so that the movable swage die 369 will return toward the fixed swage die by the spring restoring force when the pressure provided by the air cylinder 395 is terminated.

FIG. 14(*c*) shows die 361 in its fixed position, and movable die 369 in its spaced apart position prior to receiving the surgical needle 9 presented by multi-axis gripper 155. Suture alignment die 362, containing suture guide funnel half 362*b*, is positioned under swage die 361, and free to slide laterally within limits. Alignment die 362 has a tang 362*a* that protrudes into cavity 361*a* formed within swage die 420. Compression spring 361*c* bears against the back wall of cavity 361*a* and tang 362*a* such that funnel die 362 slides forward until it is constrained by cavity wall 361*b*. In this position, it is forward of the center axis defined by the suture receiving end of the needle, and serves as a shelf 362*c* that helps assure suture receiving end 7 of needle 9 is in position for swaging. In this stage of the cycle, the parts are not positioned for suture insertion, and suture clamp 265*a* gripping suture 255 and stiffened end 258, are in dwell. Suture alignment die 368, containing funnel half 363, is fastened to swage die 369 by suitable fastening means, described in detail below, and travels with it to the open position shown.

While the swage dies are apart, the multi-axis gripper 155 is extended to position the suture receiving end 7 of needle 9 within the opening 392 as shown in FIG. 14(*c*) and FIG. 15(*a*). After positioning the suture receiving opening 7 of needle 9 at the swage die opening 392, the swage die 369, and suture alignment die 368, are moved toward needle 9 with the resilient spring force present in spring 364 (FIG. 15(*a*)) that is sufficient to enable the die 369 to grip and locate the suture receiving end 7 precisely against fixed swage die 361 without deforming the cavity of the suture receiving opening 7 formed therein. Concurrently, needle retaining pin 142 in multi-axis gripper 155 is raised by downward external force on plunger 149, as described above, thereby releasing the needle so that its position is determined by the grip of swaging dies 361 and 369. The motion of dies 368 and 369 cause the face 368*a* of suture alignment die 368 to come in contact with the corresponding face 362*c* of suture alignment die 362. The resilient force causing this motion is forceful enough to compress spring 361*c*, and move funnel die 362 to the left, such that tang 362*a* is no longer in contact with cavity wall 361*b*. Dimensioning of dies 369 and 368 is such that this motion results in the formation of two funnel halves 362*b* and 363 defining a smooth conical shape that is coaxial with the suture receiving end 7 of needle 9. FIG. 14(*d*) shows the suture receiving end 7 being gripped by the swage dies 361,369 prior to suture insertion. Note that the exit diameter of the conically shaped funnel guide formed of funnel halves 362*b* and 363 is preferably equal to or greater than the diameter of the suture tipped end 258 and smaller than the diameter of the suture receiving end 7 of the needle 9, as shown in FIG. 14(*e*), so that the tipped end 258 of the suture strand may be easily inserted therein.

FIG. 14(*e*) shows suture gripper 265*a* moved vertically to the insertion position, which causes stiffened suture end 258 to enter funnel 362*b* and 363, and be guided into the suture receiving cavity 7 of needle 9 axially aligned therewith. Once the strand is inserted into the suture receiving end 7 of the needle (step 28) as discussed above, the automatic swaging of the suture receiving cavity occurs. In the preferred embodiment of the swaging assembly 390 shown in FIG. 15(a), a pneumatic air cylinder 365 provides air pressure to actuate cam 375 that bears on lever 397 to thrust movable swage die 369 toward the fixed swage die to accomplish the swaging of the suture receiving end of the needle placed therebetween. Air pressure is supplied to the swage cylinder 365 via ports 366,367 under the control of the control system computer 99.

Figure 14A:
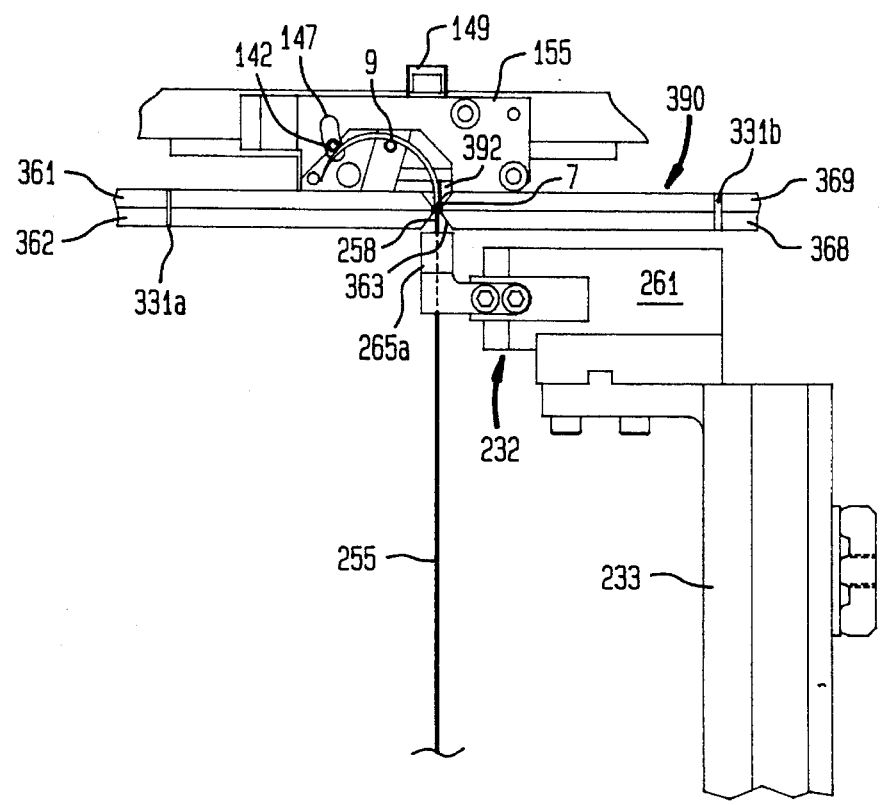
FIG. 14(a) is a detailed view of the gripper 232 shown inserting the suture tip 258 within the confines of the suture receiving end of the surgical needle.
Figure 14B:
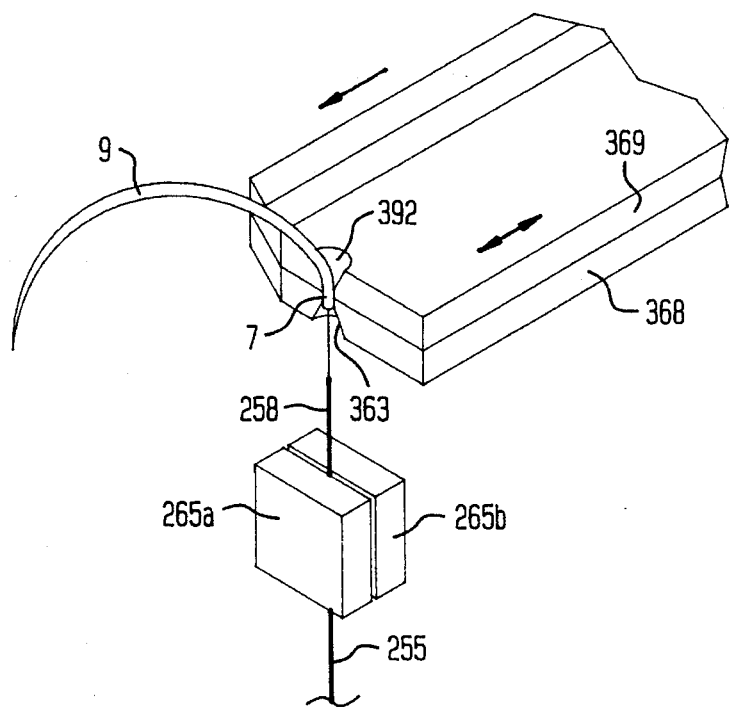
FIGS. 14(b)–14(f) illustrate the multi-axis needle gripper 155 and swaging and suture alignment dies shown in various stages of the suture insertion and needle swaging sequence.
Figure 14C:
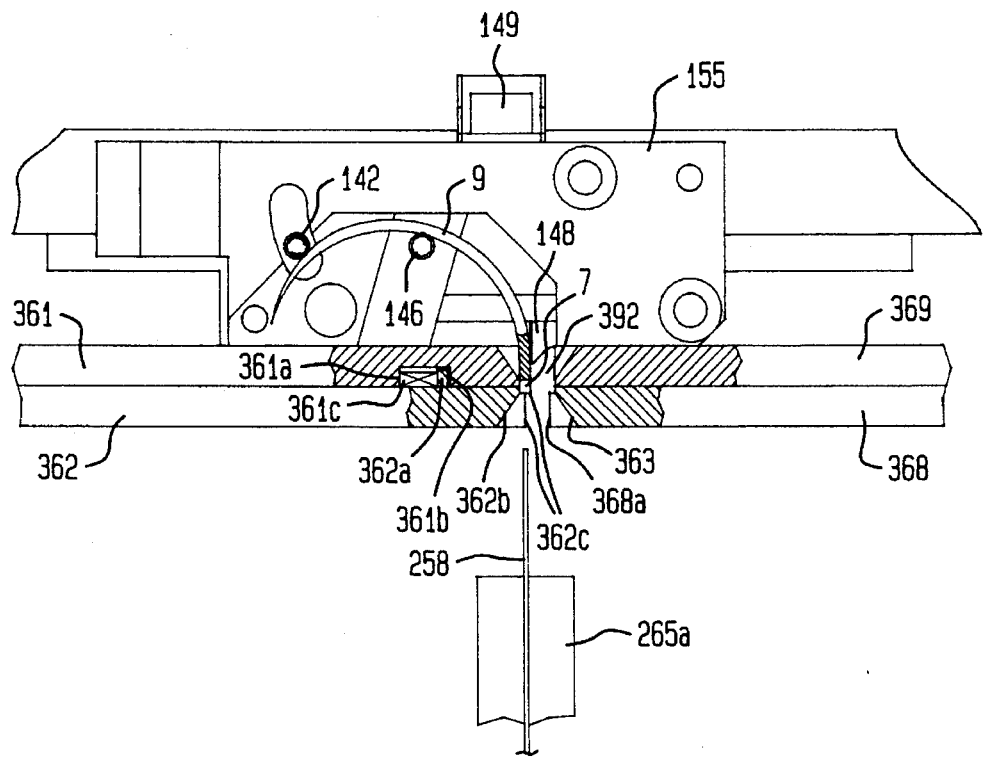
Figure 14D:
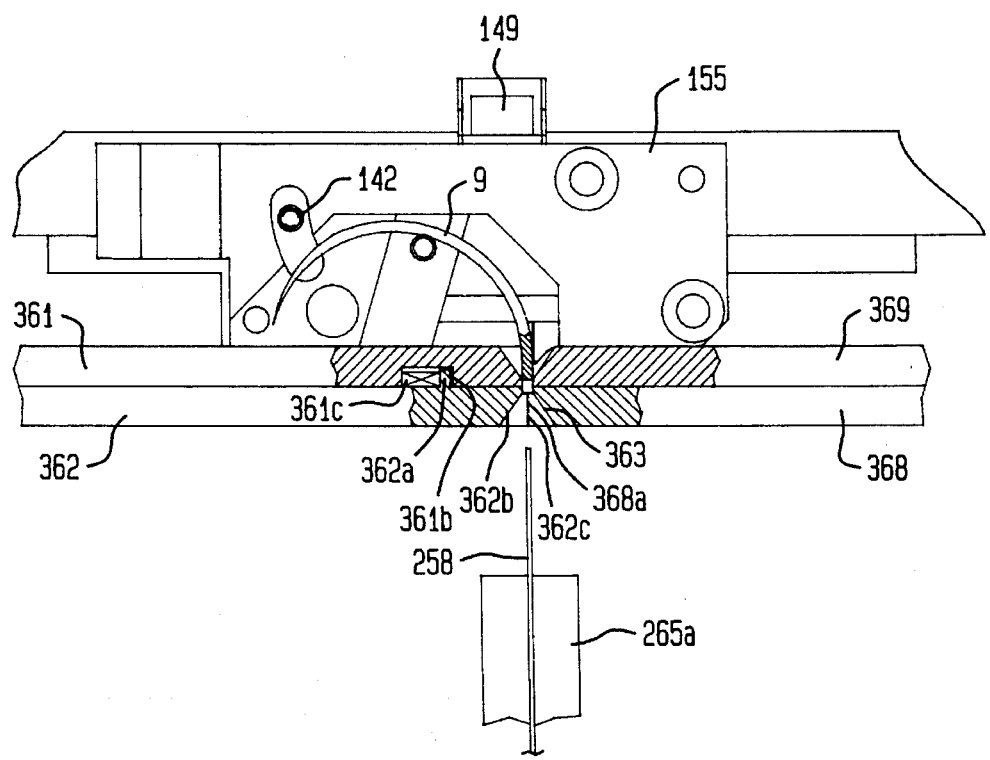
Figure 14E:
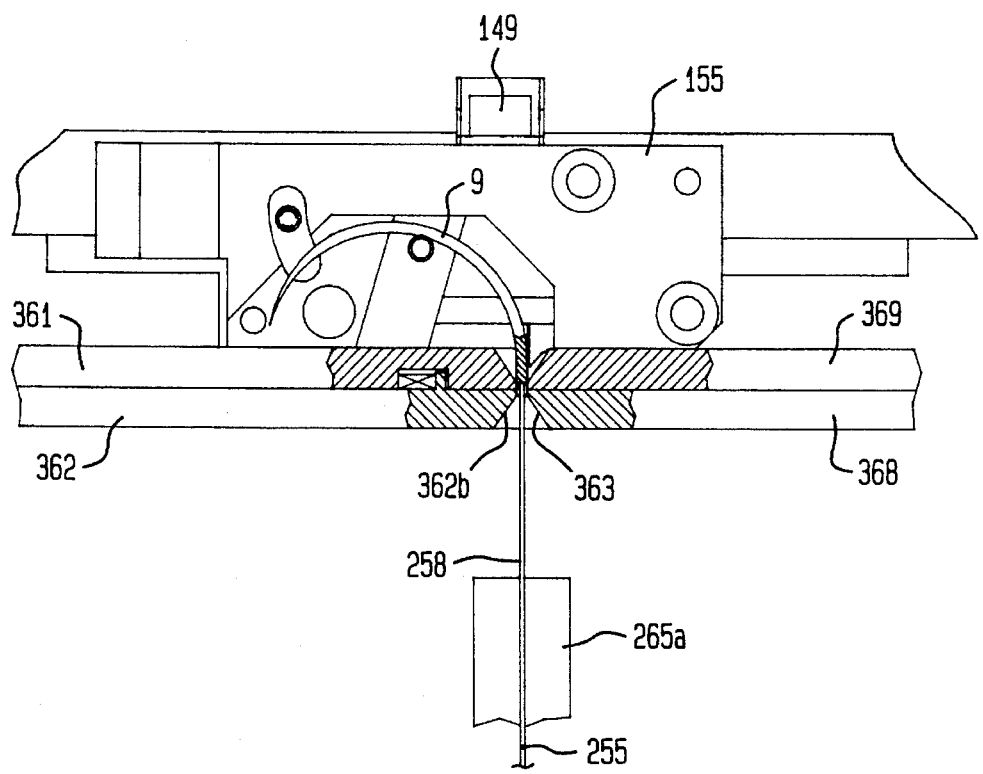
Figure 14F:
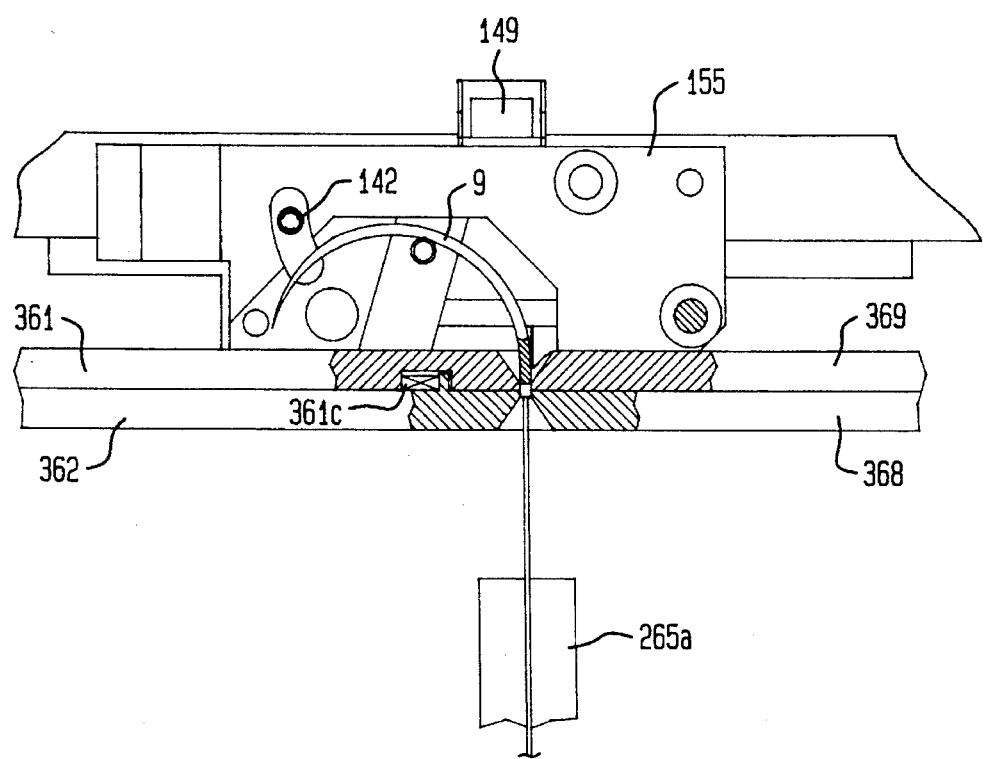

FIG. 14(f) shows the completed swage stroke. The swage die 369 has been driven to a fixed stop by the swage cylinder, which exerted sufficient force to deform the suture receiving end 7 of needle 9. As deformation takes place, suture alignment die 368 further displaces funnel die 362, causing additional compression of spring 361c. In the preferred embodiment, the movable swage die 369 comes to an automatic stop by a swage stop mechanism herein described.

Figure 15B:
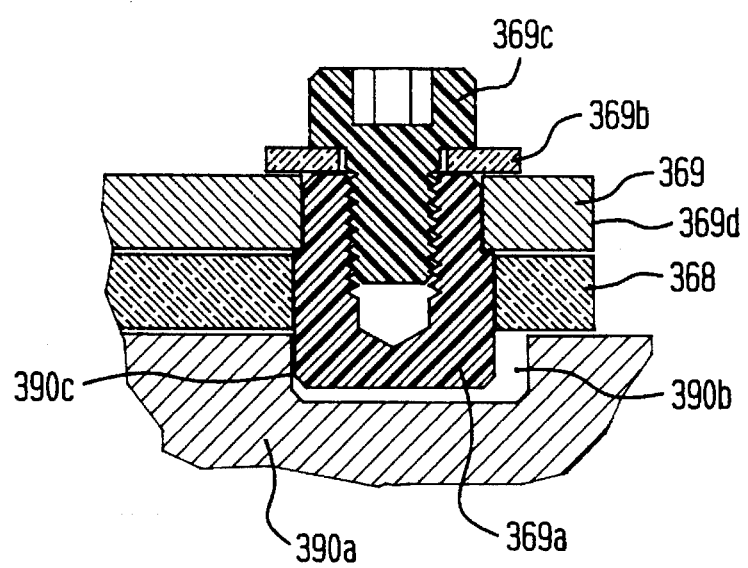
FIG. 15(b) is a detailed view of the swage stop mechanism for swage assembly 390.

As shown in FIG. 15(b), movable swage die 369 and suture alignment die 368 are mechanically held coincident to each other by shouldered post 369a, the smaller diameter of which is a light press fit into the mating hold in die 369. Cap screw 369c, with washer 369b retain the post in die 369. The larger diameter of post 369a, below die 369, extends through a light press fit hole in funnel die 368, so that the right hand swage and funnel dies are linked to move together laterally during the swaging cycle. The lower portion of shouldered post 369a extends through funnel die 368, into groove 390b, which is cross milled into swage assembly frame 390a. When the swage stroke is performed, the swage cylinder drives this die assembly to the left until it is positively stopped by the lower portion of post 369a striking wall 390c of groove 390b. This stalls air cylinder 365, so that the stroke of the movable right hand die assembly shown is always the same for repeating cycles of the machine.

In an alternative embodiment, both swage dies 361,369 may be movable towards each other to accomplish swaging. Furthermore, an adjustable swage stop mechanism for changing the swage stroke distance of one of the movable dies may be provided to further control the swaging pressure applied to the suture receiving opening and obviate the need for a fine-tune positioning adjustment for a fixed swage die.

As shown in the top view of FIG. 15(a), a needle fence assembly 398 is provided to ensure that the needle 39 does not tip or become misaligned when the end 37 of the relaxed needle is positioned between the swage dies. The needle fence assembly 398 comprises a needle fence plate 399 whose distance from the tapered swage die opening 392 is adjustable depending upon the size of the surgical needle to be swaged.

In the preferred embodiment, the degree of swage compression imparted on the needle, and resulting strength of grip by the needle on the suture, is adjusted by precise positioning of the fixed die 361. As shown in FIG. 15(a), servomotor 345 drives pulley 344 via timing belt 461, which rotates the swage adjust screw 347. The pitch of the swage adjust screw 347 is selected to move sliding wedge 348 a small distance. The swage die 361 has a complementary ramp angle 343 at the opposite end which bears on the wedge 348 to retract or advance the position of the swage die 361 a precise distance proportional to the movement of the sliding wedge. Thus, the rotation of the swage adjust screw 347 and motion of the sliding wedge 348, results in transverse movement of the swage die 361 to thereby finely adjust its fixed position. For example, when a larger suture is to be swaged to a needle, the position of the fixed die 361 may be moved further away from the suture drawing axis so as to provide the desired amount of deformation when the swaging pressure is applied to the needle by the movable swage die 369. In the preferred embodiment shown in FIG. 15(a), the control system computer 99 will send the appropriate signals to automatically direct the servomotor 345 to adjust the position of the swage adjust screw 347, and hence, the position of the fixed die 361, in accordance with the pull-out test values of the needle-suture bond as measured by automatic pull-test system as explained in further detail below. Specifically, appropriate control signals may be generated to direct the servomotor 345 to adjust the rotational position of the swage adjust screw 347 in accordance with stored statistical results of the pull-testing occurring at the pull-test station. Automatic pull-testing of the armed needle is desirable to ensure that the upstream swaging dies are optimally positioned to avoid over-swaging the needle-suture bond and hence, preventing the likelihood of clip-off, and, to avoid under-swaging the needle-suture bond to prevent the chance of pull-out.

Immediately after the short stroke of the right or top gripper 232, the left gripper 230 secures the suture strand, and the suture material 255 is cut by the cutter assembly 280 in the manner described above and as indicated in step 30 in FIG. 3(b). As shown in FIG. 12(a), the cutter assembly 280 is positioned slightly above the left gripper 230 so that the indefinite length suture strand 255 will be gripped when the swaged strand is cut. Thus, the left gripper 230 is now gripping the suture material 255 with a tipped end 258 and it now becomes the lead gripper.

In the preferred embodiment shown in FIG. 12(a), a vacuum air flow is energized to pull the strand of material 255 toward the nylon screen 357 to facilitate the cutting of the material thereof. After cutting of the indefinite length suture material 255, the tail end of the length of suture material that had been swaged to the surgical needle is sucked into a large vacuum pipe 358, that is connected to a vacuum assembly (not shown) by vacuum hose 359 as shown in FIG. 12(a). The vacuum created in vacuum pipe 358 exerts a mild tension in the strand of material to keep the tail end from entanglement or coming into contact with the machinery. However, it is mild enough to allow the strand to be pulled out of the pipe 275 as the armed needle is indexed for further downstream processes.

After swaging of the needle, the movable die 369 is again retracted by air cylinder 365 and the pin 142 of the multi-axis gripper 155 is actuated to engage the armed needle in the manner described above. Subsequently, the multi-axis gripper 155 is retracted (step 30) to its position along the swage dial 150 for subsequent indexing to the pull-test station 300 for further processing (step 31).

The cycle continues at the swaging station with the new lead gripper vertically drawing the material 255 along the height of the drawing tower 220 to position the next strand to be cut for insertion within the surgical needle. The process of advancing suture material 255 by alternating grippers at each cycle eliminates the recycle or return time for retaining the gripper to the original position.

Automatic Pull-test Station

Figure 3B:
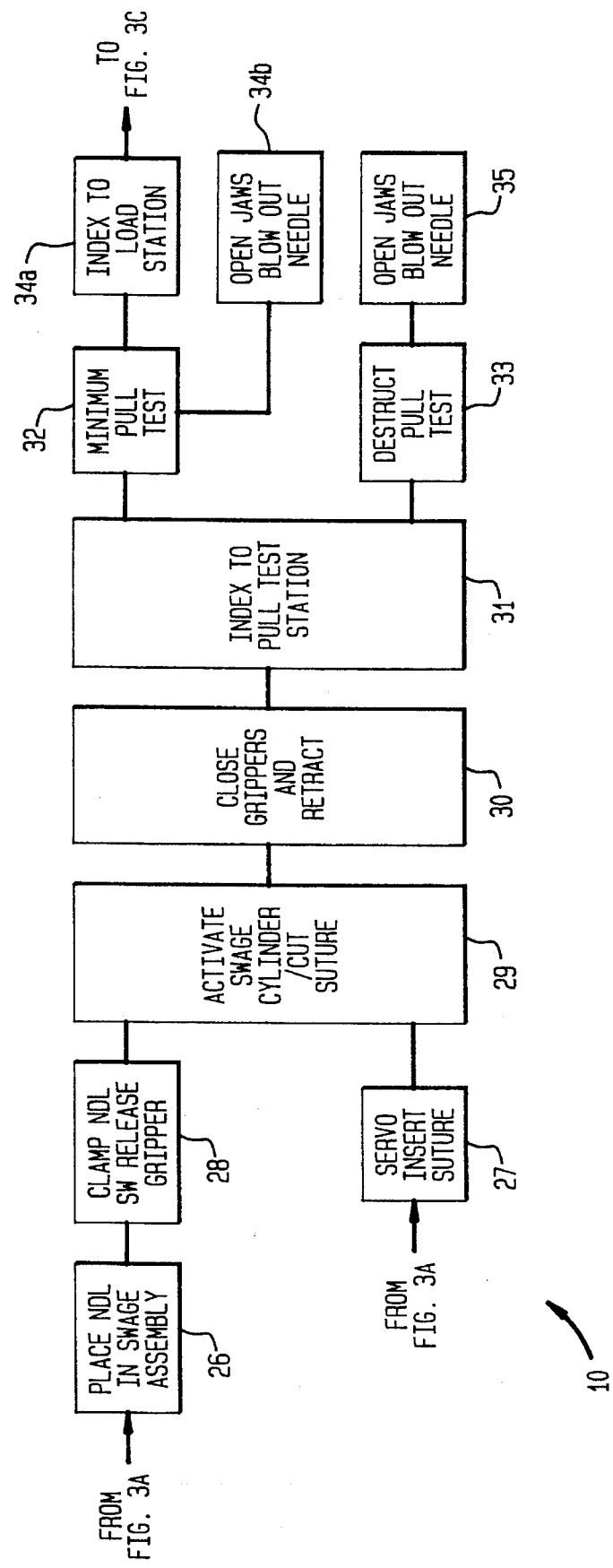

A test of the strength of the swaging bond of the armed needle indexed at the automatic pull-test station 300 may be performed as described in detail below and in further detail in copending patent application U.S. Ser. No. 08/181,607 assigned to the same assignee of the present invention and incorporated by reference herein. Automatic pull-testing of the armed needle is desirable to ensure that suture pull-test requirements are met. Specifically, as described in detail below, either a minimum pull-test, indicated as step 32 in FIG. 3(b), or, a destructive pull-test, indicated as step 33 in FIG. 3(b) is being performed at the pull-test station 300.

Figure 20:
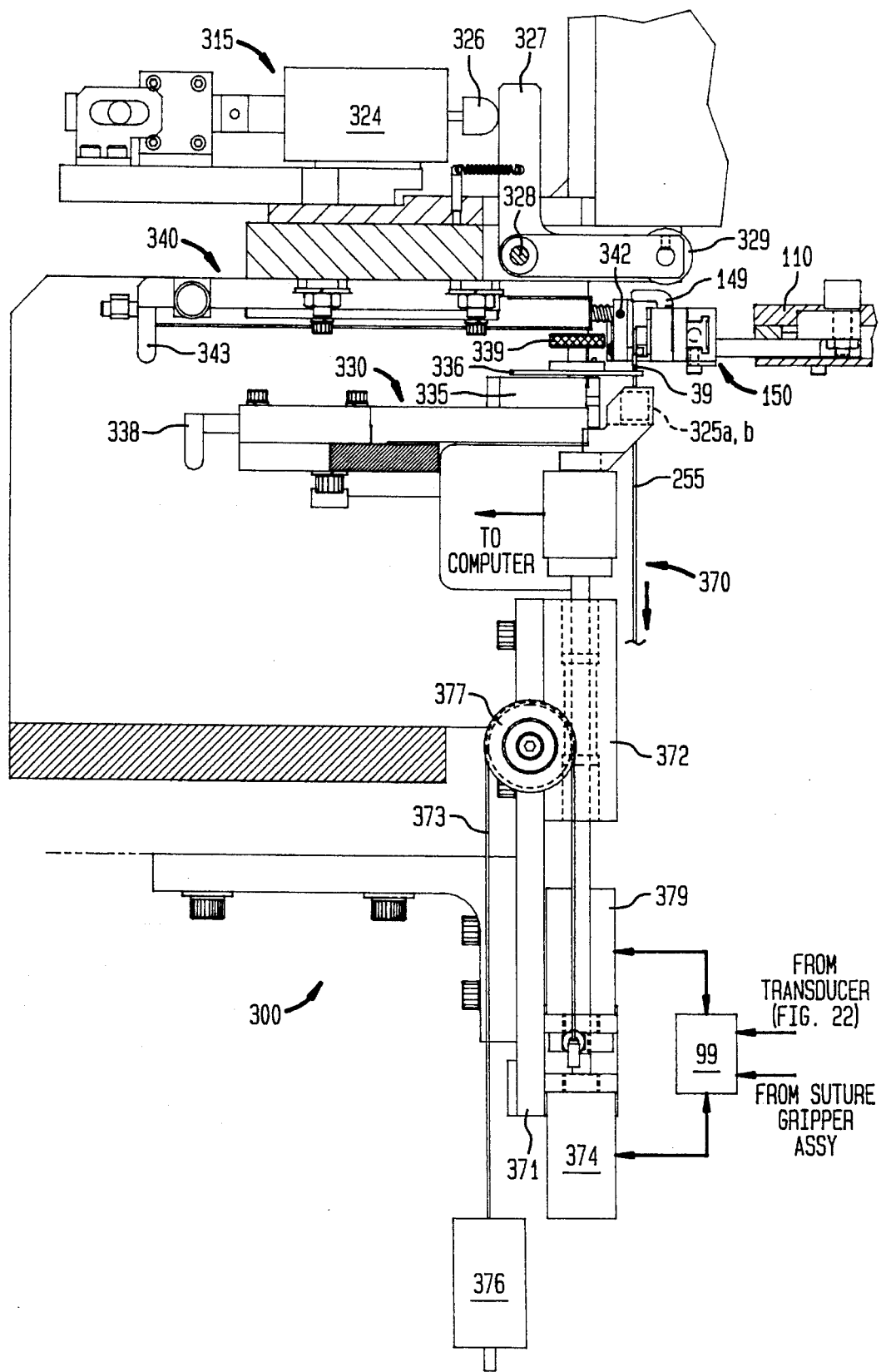
FIG. 20 is an assembly drawing of the automatic pull-test station 300 of the instant invention.
Figure 21A:
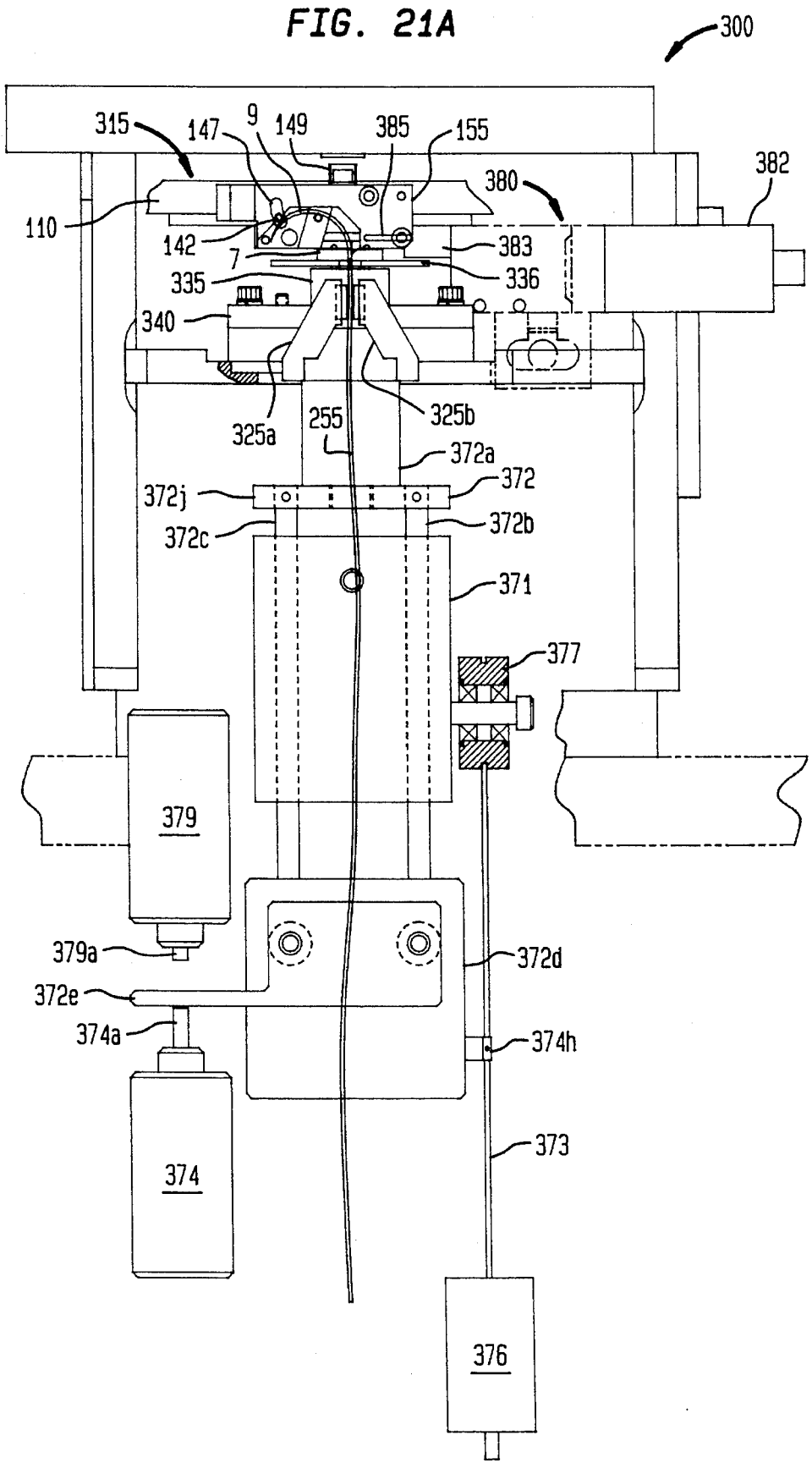
FIG. 21(a) is a front view of the automatic pull-test station 300 of the instant invention with the needle fence assembly 340 partially removed.
Figure 21B:
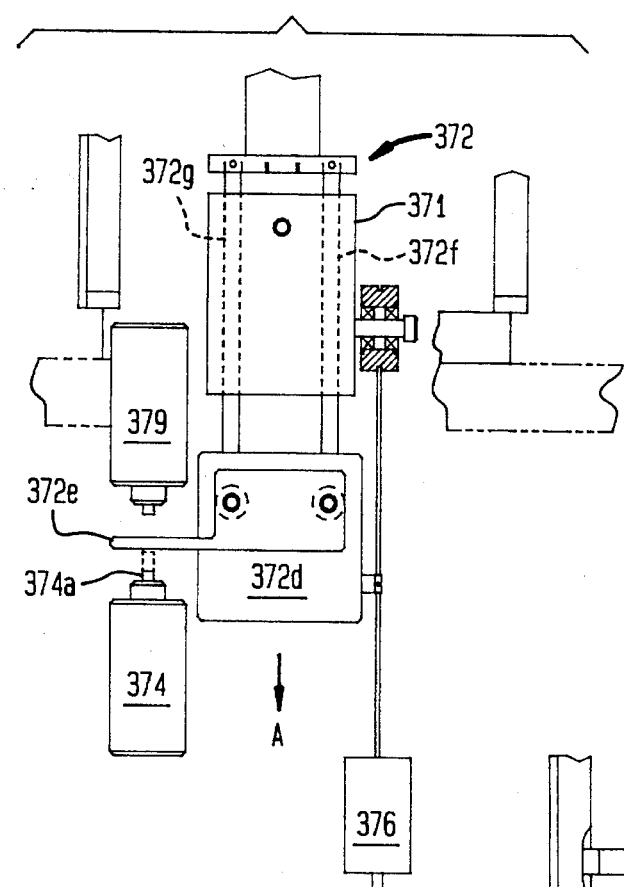
FIG. 21(b) is a detailed front view of the slide assembly means while performing a minimum pull-test.
Figure 21C:
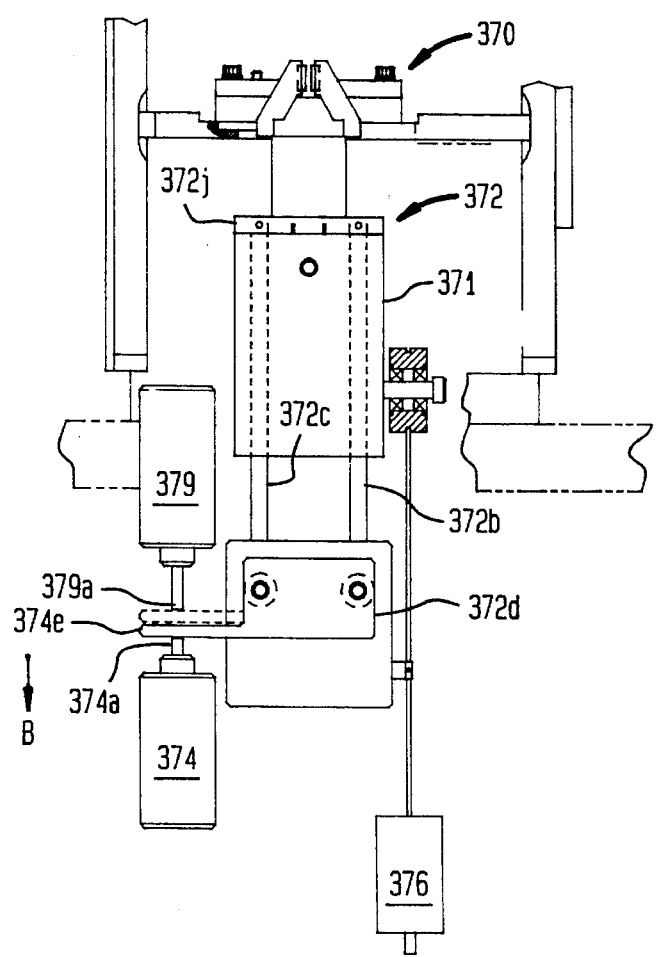
FIG. 21(c) is a detailed front view of the slide assembly means while performing a destructive pull-test.

The automatic pull-test assembly 300 for accomplishing automatic pull-testing of an armed surgical needle is shown generally in FIGS. 20 through 21(c). The automatic pull-test assembly 300 generally comprises a load cell mounting assembly 330 for mounting a load cell 335 which functions to receive the armed needle 9 from the multi-axis gripper 155 which is indexed thereto as shown in FIGS. 20 and 21(a). A needle release assembly 315 is provided for relaxing the armed needle from the grip of the multi-axis gripper 155. Pull-test fence assembly 340 is provided to prevent the armed needle 9 from tipping over or becoming misaligned when the armed needle is relaxed. Suture gripping assembly 370 containing retractable gripper arms 325a,b for gripping the suture 255 during the pull-tests, and which are connected to the weighted slide block assembly 372 for performing the pull-test is provided as shown in FIG. 20. A detailed description of each of these assemblies and their interaction will be explained in detail hereinbelow.

As shown in FIGS. 20 and 21(a), an armed surgical needle 9 is retained by a multi-axis gripper 155 and, in the manner described above, is indexed to the automatic pull test station 300 by the rotary swage dial 150 partially illustrated in the FIG. 20. To position the armed needle 9 in the load cell 335, the multi-axis gripper is extended from the swage dial 150 so that the end portion 7 of needle 9 is positioned above a corresponding receiving blade 336 of the load cell 335 as shown in FIG. 21(a).

Figure 22:
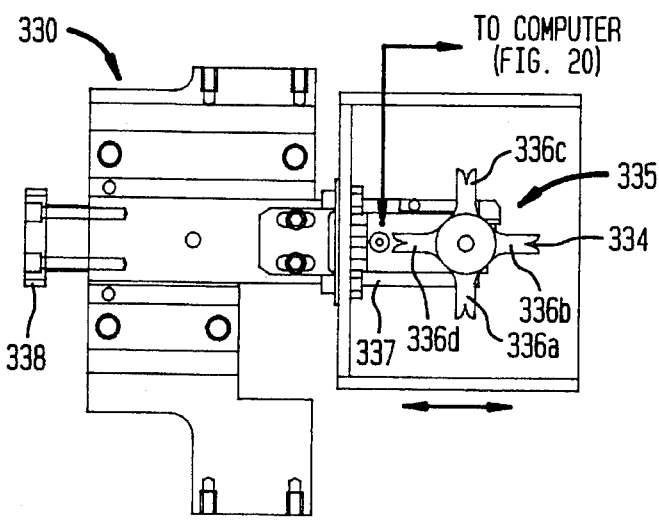
FIG. 22 is a top view of the load cell assembly 330 of the automatic pull-test assembly.

FIG. 22 illustrates a top view of the load cell mounting assembly 330 with load cell 335 mounted thereon. In the preferred embodiment, load cell 335 has mounted thereon four (4) thin needle supporting blades 336a,b,c,d for supporting the suture receiving end portion 7 of various size surgical needles with the suture material 255 depending therefrom. For instance, load cell needle supporting blade 336a labelled "1/0" accommodates a larger sutures having a diameter of approximately 0.017+/–0.001 inches; load cell needle supporting blade 336b labelled "2/0" accommodates sutures having a diameter of approximately 0.014+/–0.001 inches; load cell needle supporting blade 336c labelled "3/0" accommodates sutures having a diameter of approximately 0.011+/–0.001 inches; and load cell needle supporting blade 336d labelled "4/0" accommodates a smaller suture with a diameter of approximately 0.009+/– 0.001 inches in the preferred embodiment. Depending upon the batch of surgical needles currently being pull tested, the appropriate needle supporting blade 336a,b,c,d will be positioned to receive the needle from the multi-axis gripper. Knob 339 located centrally on top of the load cell 335 may be manually operated to rotate the load cell and position the correct sized suture receiving blade prior to carrying out automatic pull-testing. Additionally, the load cell 335 may be laterally positioned by moving slide handle 338 and consequently load cell platter 337 towards or away from the suture needle indicated by the arrow in FIG. 22.

Figure 23:
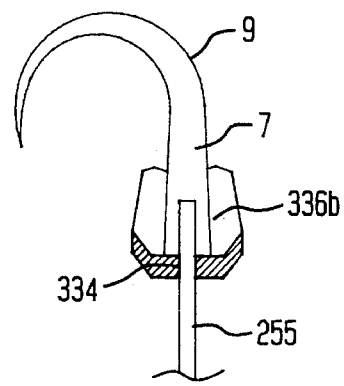
FIG. 23 is an enlarged view of an armed needle 9 supported by the suture receiving blade 336b of the load cell 335 with the suture threaded between the suture receiving opening 334.

The multi-axis gripper 155 is initially positioned so that the end portion of armed needle 9 is supported by the appropriate needle supporting blade 336 (e.g. blade 336b). FIG. 23 is a front cross sectional view illustrating the suture receiving end portion 7 of needle 9 resting upon the needle supporting blade 336b with the suture strand 255 threaded between the suture receiving guide 334.

Figure 30:
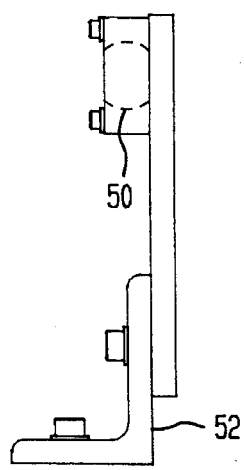
FIG. 30 illustrates an elevational view of the detector assembly as viewed in the direction of line 30—30 in FIG. 29.

Non-destructive pull testing of the armed surgical needle 9 is accomplished as follows:

After positioning the multi-axis gripper as heretofore described, gripper arms 325a,b of suture gripping assembly 370 are extended from a retracted position to grip the suture strand 255 slightly below the needle supporting blade 336 of load cell 335 as shown in FIG. 30. A gripper actuator 372a is provided for opening and closing gripper arms 325a,b, as shown in FIG. 20, and is controlled by a control system program resident in control system computer 99 as explained in further detail in copending patent application U.S. Ser. No. 08/181,607 assigned to the same assignee of the present invention. FIGS. 20 and 21(a) illustrate the slide block assembly 372 that is composed of slide rods 372b,c that are connected to a lower slide block 372d. Slide block 372d includes a slide finger 372e upon which air cylinder piston rods 374a and 379a, of respective air cylinders 374, 379, apply respective upward and downward forces depending upon the type of pull-test that is to be performed. As shown in FIG. 21(a), piston rod 374a is shown in an extended position providing an upward force that supports slide finger 372e and consequently maintains slide block 372d of slide assembly 372 at a fixed vertical position.

Slide block 372d is counterweighted to a net downward weight of 2 to 5 ounces by appropriately sized counterweight 376 that acts through cable 373, around pulley 377, and through attachment point 372h. This counterweight 376 acts to pull upward on slide block 372d at the attachment point 372h.

To accomplish the non-destructive pull test, piston rod 374a of air cylinder 374, mounted on the mechanism frame 371 and controlled by system computer 99, is retracted from its extended position (FIG. 21(a)) supporting the slide finger 372e as shown in dashed line in FIG. 21(b), by reversing its air supply (not shown), to the position shown in the figure. The piston rod 374a is retracted to remove the upward force on slide finger 372e, as shown in the FIG. 21(b), to thereby impose the counterbalanced net weight of 2 to 5 ounces of slide block 372d on the swage attachment means of suture 255 in needle 9, in the direction of arrow "A". Accuracy of this system is enhanced because slide block 372d, suspended on slide rods 372b,c, are mounted in low friction ball bushings, 372f and 372g, that are pressed into slide mount 371, thereby imposing minimal mechanical drag on the system.

Note in FIG. 20, that the slide block mount 371 is positioned parallel to the axis of the suture 255 depending from the needle 9, and is located a distance away from the suture 255 corresponding to the length of the gripper arms 325a,b.

Simultaneous with or momentarily before the slide assembly 372 is released, the needle release assembly 315 is actuated to enable multi-axis gripper 155 to disengage its grip on the armed needle 9. Releasing the armed needle from the grip of the gripper 155 is necessary to ensure that it is firmly positioned on the load cell needle supporting blade 336. Moreover, to provide an accurate pull-test, the needle must be released so that there is no existing upward force that would cause false results.

As shown in FIG. 20, needle release assembly 315 comprises needle release solenoid 324 that is actuated to extend pusher 326 into pivotal lever arm 327. Pivotal lever arm 327 pivots about pin 328 to depress plunger 149 of the multi-axis gripper 155 at one end 329 thereof. As shown in FIG. 21(a), depressing plunger 149 enables pin 142 to retract within pin guide 147 to release the armed needle 9 engaged thereby. Further details of the operation of the multi-axis gripper 155 can be found in the above-mentioned copending patent application U.S. Ser. No. 08/181,599.

To prevent the armed needle 9 from becoming misaligned or from tipping over after the multi-axis gripper 155 releases its grip on the needle, a needle fence assembly 340 is provided. As shown in FIG. 20, the needle fence assembly 340 includes vertical fence plate 342 which can be adjusted to lie flush against the gripper 155 to retain the armed needle in an upright position. Adjusting the lateral positioning of the vertical fence plate 342 is accomplished by moving slide handle 343 for an appropriate distance as shown in FIG. 20. In the preferred embodiment, the configuration of the face of the vertical needle fence plate 342 (not shown) may be changed to accommodate the configurations of different size needles.

The controlled release of the minimum pull-test is of short duration, preferably ranging in milliseconds. If the test is successful, i.e., the suture meets the minimum pull-test requirements, the needle is re-gripped by the multi-axis gripper 155 by deactuating the needle release solenoid 324 (FIG. 20) which releases the force on plunger 149. The suture grippers 325a,b are then retracted to their open position to release their grip on the suture 255 as controlled by the control system. Subsequently, the multi-axis gripper 155 is retracted and the rotary swage dial is rotated to convey the armed needle downstream for further processing.

If the suture fails the minimum pull-test, i.e., if the suture 255 is dislodged from the surgical needle 9 as a result of the controlled release, the control system computer 99 is flagged so that the disarmed needle 39 will be ejected at the pull-test station. The dislodged suture strand 255 will be drawn into a vacuum assembly (not shown) and the needle 9 will be ejected by a needle stripper assembly 380 shown generally in FIG. 21(a) and in detail in FIG. 24. As shown in FIG. 24, needle stripper solenoid 382 will be actuated by a control signal output from the control system computer 99 to extend needle stripper blade 385 mounted on a slide block 383. The needle stripper blade 385 is shown in FIG. 20 located next to the needle 9. Thus, when the needle is in its relaxed state on the multi-axis gripper 155 and the minimum pull-test fails, the needle stripper blade 385 is extended to remove the needle from the gripper. The needle will fall and be collected by appropriate collection means (not shown) located at the pull-test station.

To prepare for the next armed needle to be pull-tested, the slide assembly 372 and retracted gripper arms 325a,b are pushed back up the slide mount 371 to their unloaded position by an appropriate upward force supplied by the air cylinder 374 and piston rod 374a as controlled by the control system computer 99. At this time, another flag may be sent for storage to the control system computer that indicates that the pull-test performed on the particular needle 9 was successful and that the armed needle may be conveyed downstream for packaging thereof.

In the preferred embodiment of the minimum and destructive pull-test systems shown in FIGS. 20–23, the load cell 335 and the needle support blades 336a,b,c,d thereof comprise a piezoelectric transducer that measures the force applied by the suture gripping assembly to the needle-suture assembly 9. The transducer load cell 335 may be interfaced with the control system computer 99 by conventional means as shown in FIGS. 20 and 22, and, in the preferred embodiment, is a 1000 gram transducer manufactured by Techniques Co. (Model No. GS-1K). The forces applied to the suture 9 and measured by the load cell transducer 335 during the destructive pull-testing may be stored for statistical purposes or for real-time monitoring during a swage die setup routine that may take place when a new batch of surgical needles are to be swaged. For instance, if the destructive pull-tests fail and the forces measured by the transducer are determined to be at the low end of a predetermined range, then the control system computer 99 will acknowledge this and send appropriate signals to the upstream swaging assembly (not shown) causing a fixed swaging die to be advanced an incremental amount toward the movable swage die, resulting in subsequent swages being stronger. Likewise, if the destructive pull-test passes, i.e., the forces measured by the transducer are determined to be above the minimum and below an upper limit, then no die adjustment need be made.

As previously mentioned, the automatic pull-test assembly 300 is used to perform a minimum pull-test upon every armed surgical needle indexed thereto prior to automatic packaging thereof. A destructive pull-testing of the armed surgical needle is performed at every nth needle indexed thereto. The purpose of performing a destructive pull-test is to set the swage dies located at the upstream swaging station for correct maximum swage pull-out value. This is by necessity a destructive test, and the test frequency, which is programmable, is set high enough to maintain control of the operation, but low enough to avoid excessive product waste. In the preferred embodiment, this frequency is set at every 50th needle, but could be every 75th or 100th needle.

Another purpose of the destructive pull test is to aid in installing a new swage die set during a changeover procedure, which is a procedure that is used to prepare the needle sorting and swaging apparatuses (swage dies) for processing a new batch of needles when they are of a different size from a previously processed batch. Contrary to the non-destructive pull-test described above, the pull-test apparatus is programmed for 100% destructive test of a swaged needle, while the swaging assembly is operating and feeding the armed needles to the pull-test station. The die adjustment system at the upstream swaging assembly will receive a signal from the transducer load cell 335, at each machine cycle, and quickly perform a correct adjustment of the swage dies.

Destructive test pull-out values are recorded in the system computer 99 and are used to compute statistical process control information which is fed back to the machine operator through display screens.

Destructive pull testing of the armed surgical needle 9 is accomplished similarly as described herein above with respect to the minimum pull test. However, the fundamental difference is that a fixed mechanical stroke that is great enough to pull the suture out of the needle replaces the minimum 2 to 5 ounce force of the minimum pull test.

As shown in FIG. 21(c), piston rod 379a of second air cylinder 379 located opposite air cylinder 374, is programmed to provide a fixed stroke against slide finger 372e from a non-actuating position shown in FIG. 21(a) to the position shown in FIG. 21(c). This results in the vertical displacement of slide finger 372e from a position shown by the dashed line to a position shown by the solid line. This further results in a downward force upon slide block 372d, which, through slide rods 372b and c, moves slide assembly 372, including grippers 325a,b and suture 255, in the direction of the arrow "B" as shown in FIG. 21(c). Air pressure to cylinder 379 is set high enough to always pull suture 255 out of needle 9. This stroke is limited by the top portion 372j of slide assembly 372 striking the top of stationary block 371.

The force necessary to accomplish the destructive pull-test is measured by the piezoelectric load cell transducer 335 as discussed above. If it is determined by the process control algorithm (not shown) that the destructive pull-test forces as measured by the transducer load cell are lower than a predetermined range of pull-test values, the control system computer 90 will send out appropriate control signals to increase the swaging die stroke applied when swaging the suture to the needle at the upstream swaging station. If it is determined that the destructive pull-test forces as measured by the transducer load cell are higher than the predetermined range, the control system computer 99 will send out appropriate control signals to the upstream swaging assembly to move a fixed swage die a small incremental distance away from the suture, thereby decreasing the swaging pressures applied when swaging the suture to the needle.

Since the destructive pull-test necessarily results in the suture 255 becoming dislodged from the needle 9, the needle 9 is again removed from the grip of the multi-axis gripper 155 by the needle stripper blade 385 as described above. Subsequently, the gripper arms 325a,b are retracted to their open positions and air cylinder 374 provides the upward force to restore the gripping assembly 370 and slide block assembly 372 back to their normal position in preparation for the next pull-test.

Automated Packaging Machine

During the process of arming surgical needles at the needle threading and swaging dial 150, as described above, simultaneous packaging processes occur at the rotary suture wind and packaging turret 500. In essence, the suture wind and packaging turret 500 is adapted to be indexed forwardly in the direction of arrow "B" shown in FIG. 1, such that each tool nest located on turret 500 is adapted to be advanced in succession to a number of workstations located about its periphery. Further details of the automatic packaging system can be found in copending patent application U.S. Ser. No. 08/181,626 assigned to the same assignee of the present invention and incorporated by reference herein.

The foregoing indexing motions of the rotary packaging turret 500 are implemented in order to produce a completed suture package and are correlated with each other through the program-controlled operation of the machine such that the dwelling-time periods at each of the respective workstation is computed to allow sufficient time for the preceding step to be completed at the preceding workstation or workstations. This enables a smooth and continuous flow of product from the automated packaging machine and provide for high-speed and efficient manufacturing cycles.

Suture Wind and Package Deal

Figure 25:
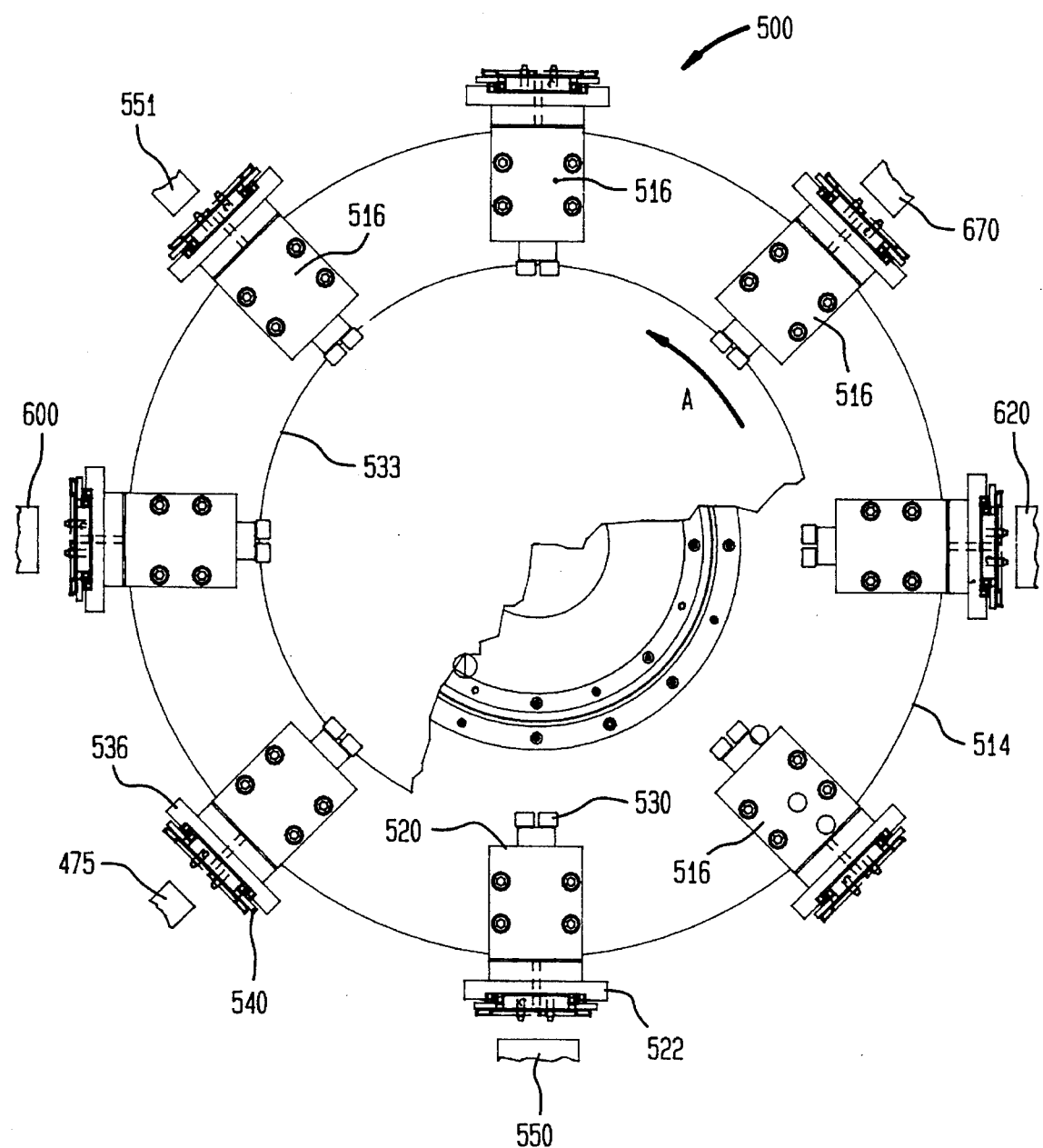
FIG. 25 illustrates a top plan view of the suture wind and packaging turret of the automatic packaging machine for needle-suture assemblies.
Figure 26:
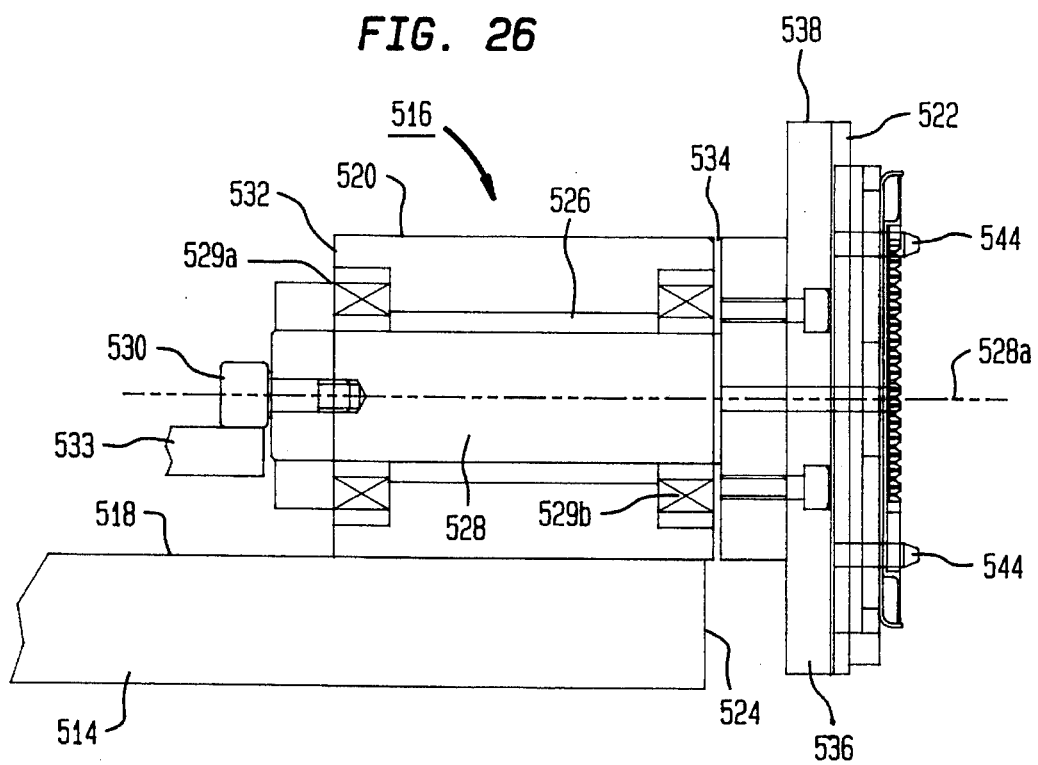
FIG. 26 illustrates, on an enlarged scale, a detailed side view of the rotary disk showing one of the tool nests for mounting a needle and suture-receiving tray.

As shown in FIGS. 25 and 26 the rotary suture wind and package turret 500 is essentially constituted of a circular disc-shaped dial 514 having a plurality of tool nests 516 located thereon in uniformly spaced circumferential array on the upper surface 518 of the rotary package turret 500, and with each tool nest extending radially outwardly of the periphery thereof.

Figure 27:
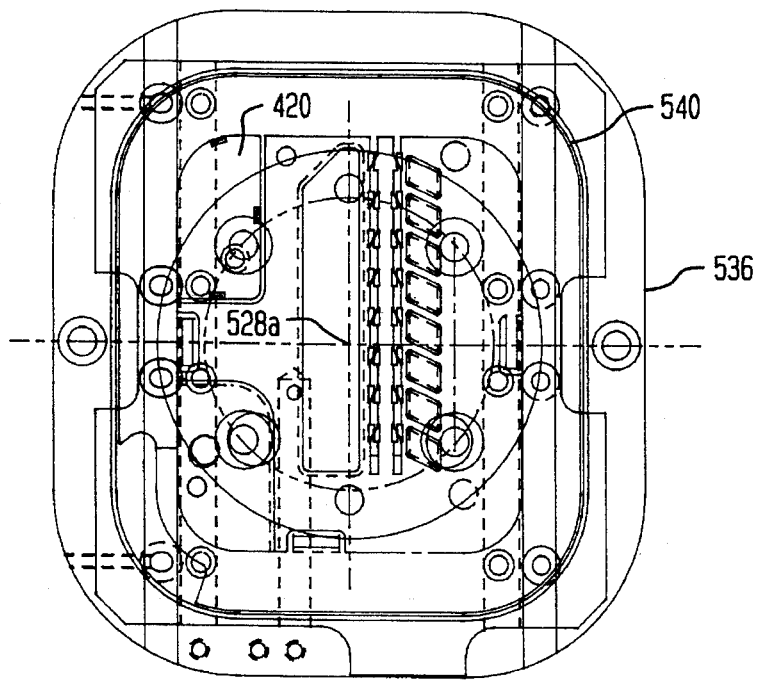
FIG. 27 illustrates a front view of the tool nest of FIG. 26.
Figure 28A:
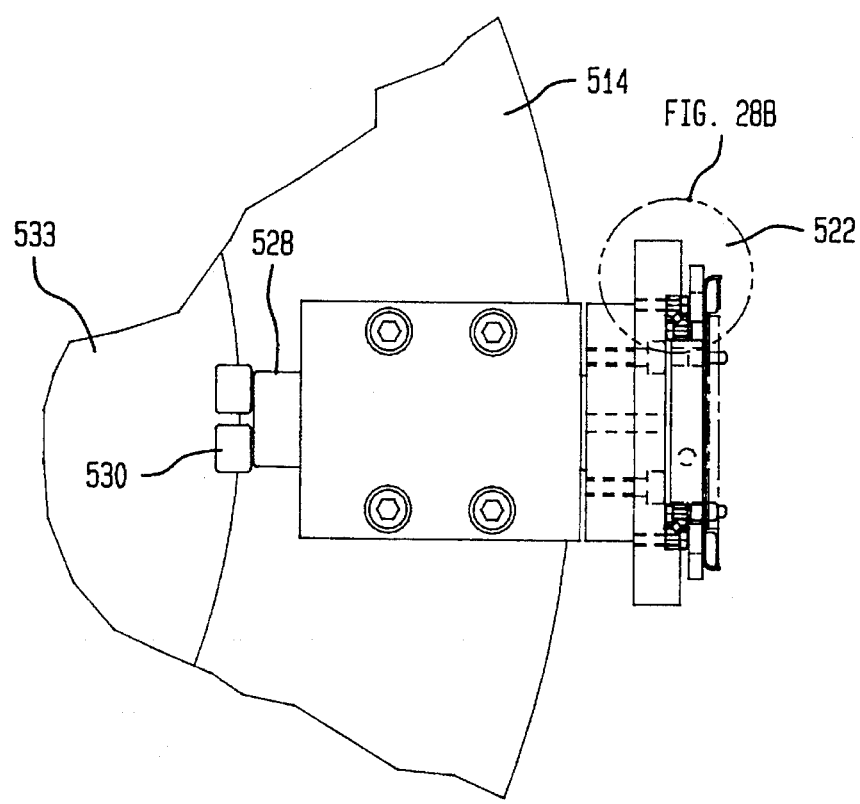
FIG. 28(a) illustrates a fragmentary top view of the rotary turret, showing an enlarged portion thereof incorporating one of the tray-mounting tool nests.
Figure 28B:
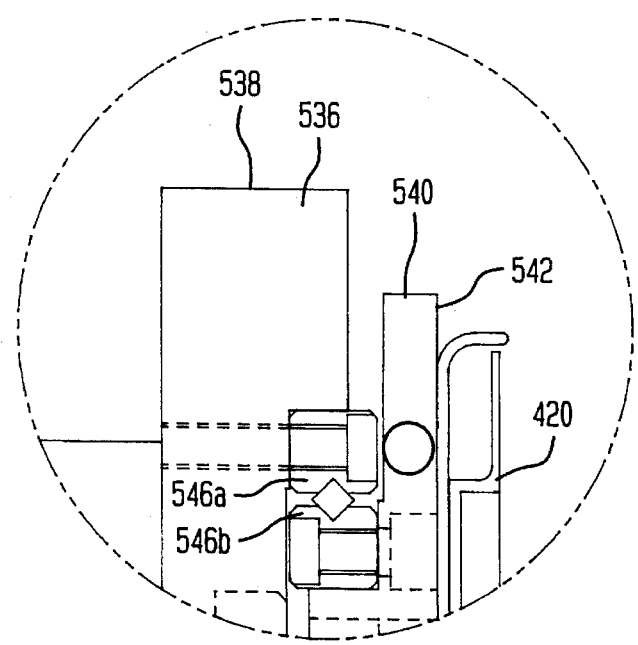
FIG. 28(b) illustrates an enlarged fragmentary detail of the encircled portion in FIG. 28(a)

Generally, as shown in FIG. 25, there are provided eight tool nests 516 arranged at 45° angular spacings from each other about the circumference of the dial 514. As shown in detail in FIGS. 26 through 28 of the drawings, each tool nest 516 consists of a housing 520 which is fixedly mounted on the upper surface 518 of the disc-shaped dial 514 of rotary dial 500, and includes a portion 522 radially outwardly projecting from the circumferential edge 524 of the disc member 514 which is operative to receive and support flat-bottomed injection-molded plastic trays utilized in the forming of suture packages containing surgical needles and attached sutures, as described hereinbelow.

Figure 46:
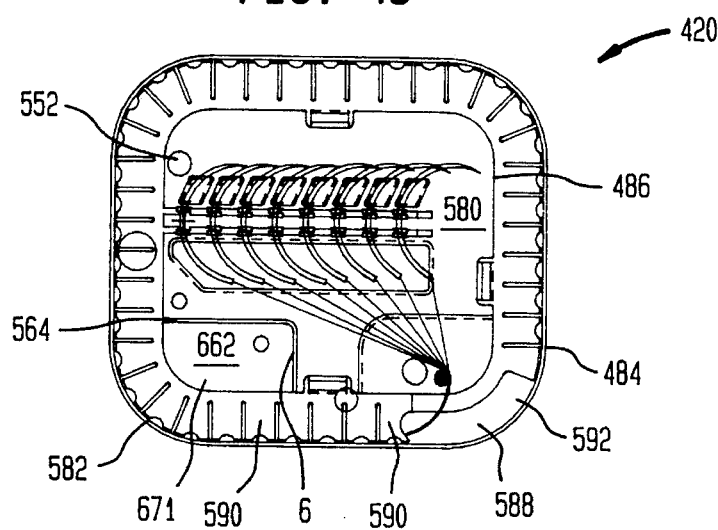
FIG. 46 illustrates a front view of a tray having needles and sutures arranged therein.
Figure 47:
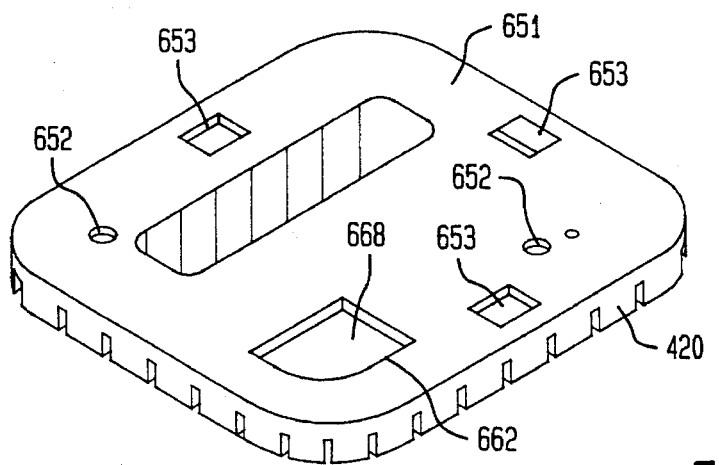
FIG. 47 illustrates a perspective view of a completed suture package.

As illustrated in FIGS. 26 through 28(a), each of the tool nests 516 comprises a housing or block 520 fixedly mounted through suitable fasteners to the upper turret surface 518 proximate the peripheral outer rim or edge 524 of the dial 514 of turret 500. Each housing 520 includes a horizontal radially extending central bore 526 having a shaft 528 supported on bearings 529a and 529b rotatably journaled therein, with the shaft being connected to a suitable drive source (as subsequently described). Cam rollers 530 mounted at the radially inner end 532 of the housing 520 are adapted to contact a cam plate dial 533 extending over the dial surface 518 during the rotation of the turret 500 for purposes as described in more specific detail hereinbelow. At the radially outer end 534 of the housing 520, there is provided structure for supporting the components for forming a suture package, the latter initially comprising a generally flat injection-molded tray 420 for receiving and retaining therein a plurality of surgical needles and attached sutures; for example, as illustrated in FIG. 46 of the drawings, and with an applied tray 420 cover as shown in FIG. 47, as disclosed in a copending patent application entitled "Multi-Strand Suture Package and Cover-Latching", commonly assigned to the assignee of the present application; (identified under Attorney Docket ETH-849), the disclosure of which is incorporated herein by reference.

The radially outer structure of the housing 520 for initially mounting the plastic suture tray 420 includes a generally rectangular, round-cornered and vertically extending plate member 536 of which the outer peripheral surface 538 forms a cam surface, employed for a suture-winding purpose as described hereinbelow, and with the plate member 536 being secured to the radially outer end of the shaft 528 for rotation therewith. Mounted on the front surface of cam plate member 536 is a plate 540 having a radially outwardly facing, vertically-oriented support surface or platform 542 possessing projecting guide pins 544 for the positioning and mounting thereon of an injection-molded plastic tray 420 adapted to be supplied with surgical needles and attached sutures. The cam plate member 536 and the plate 540 for supporting the suture tray 420 are connected with each other so as to be secured against relative rotation, both being jointly rotatable about the longitudinal horizontal axis 528a of the shaft 528 extending through the block or housing 520. However, the plate 540 for mounting the tray 420 is linearly displaceable relative to the cam plate member 536 through the provision of cooperating slide guides 546 located between these elements. These slide guides 546 are disclosed in more extensive detail in the enlarged fragmentary illustration of FIG. 28(b), where they are illustrated as mating guide rails 546a and 546b, and are provided to facilitate the successive insertion of an array of surgical needles into the tray 420 which is mounted on the guide pins 544 extending from the support surface 542 of the plate 540 of the tool nest 516.

The external configuration of both the cam plate member 536, i.e. its camming surface 538, and the support plate 540 is substantially in conformance with the outer shape of the suture tray, although larger in external dimensions than the latter.

(1) Generally, the first of the successive workstations located about the rotary suture wind and package turret 500, as is the package load station 400. As indicated at step 40 of FIG. 3(c), empty suture trays 420 are positioned on the radially outwardly facing platform or support surface 542 of the plate 540 on tool nest 516, and retained thereon by means of the guide pins 544 extending through positioning apertures in the tray 420 so as to be in a generally vertical orientation relative to the horizontal plane of rotation of the rotary dial 514. Suitable grippers of a tray 420 feeding apparatus or mechanism (not shown) may be provided to supply empty trays to successive plates 540 and position the tray 420 thereon. The grippers may obtain individual tray 420 from a suitable supply source, such as a stack of trays, and position the tray 420 one each on successive forwardly indexed platforms 540 of the tool nests 516. Alternatively, in the absence of gripper mechanisms the tray 420 may optionally be manually positioned on the guide pins 544 of platform 540 such that the rear surface of each tray 420 contacts the support surface or platform in a flat, surface-contacting relationship so as to be firmly mounted thereon.

In summation, at the package load workstation 400, the support surface or platform 542 on the plate 540 for receiving an empty injection-molded plastic tray 420 is indexed by rotary dial 514 into alignment with a tray dispensing mechanism from which a tray is gripped and removed from a stack of trays and pivoted into alignment with platform 542 and advanced thereon so as to cause the apertures in the tray to be positioned in registration on the guide pins 544 projecting from the platform 542. Thereupon, the tray dispensing mechanism is withdrawn, and placed into position to receive a successive tray which, when the first-mentioned tray is indexed forwardly by the rotary dial 514 to the next workstation, will enable a further tray to be mounted on a successive platform on a tool nest 516 located on the rotary dial 514. At that time, the vertically extending plate 540 with platform 542 and the cam plate 536 on which it is arranged are oriented in a manner with the side edges thereof vertically extending, as shown in FIGS. 26 through 28(b) of the drawings. Alternatively, if desired, this procedure of positioning a tray on the platform 542 may be manually implemented, thereby eliminating the foregoing operative structure.

Upon the withdrawal of the dispensing mechanism which positioned the empty tray 420 on the support platform 542, the rotary dial 514 is now in a condition to be indexed or rotationally advanced forwardly to the next workstation, in the direction of arrow "A" of FIG. 25.

Figure 29:
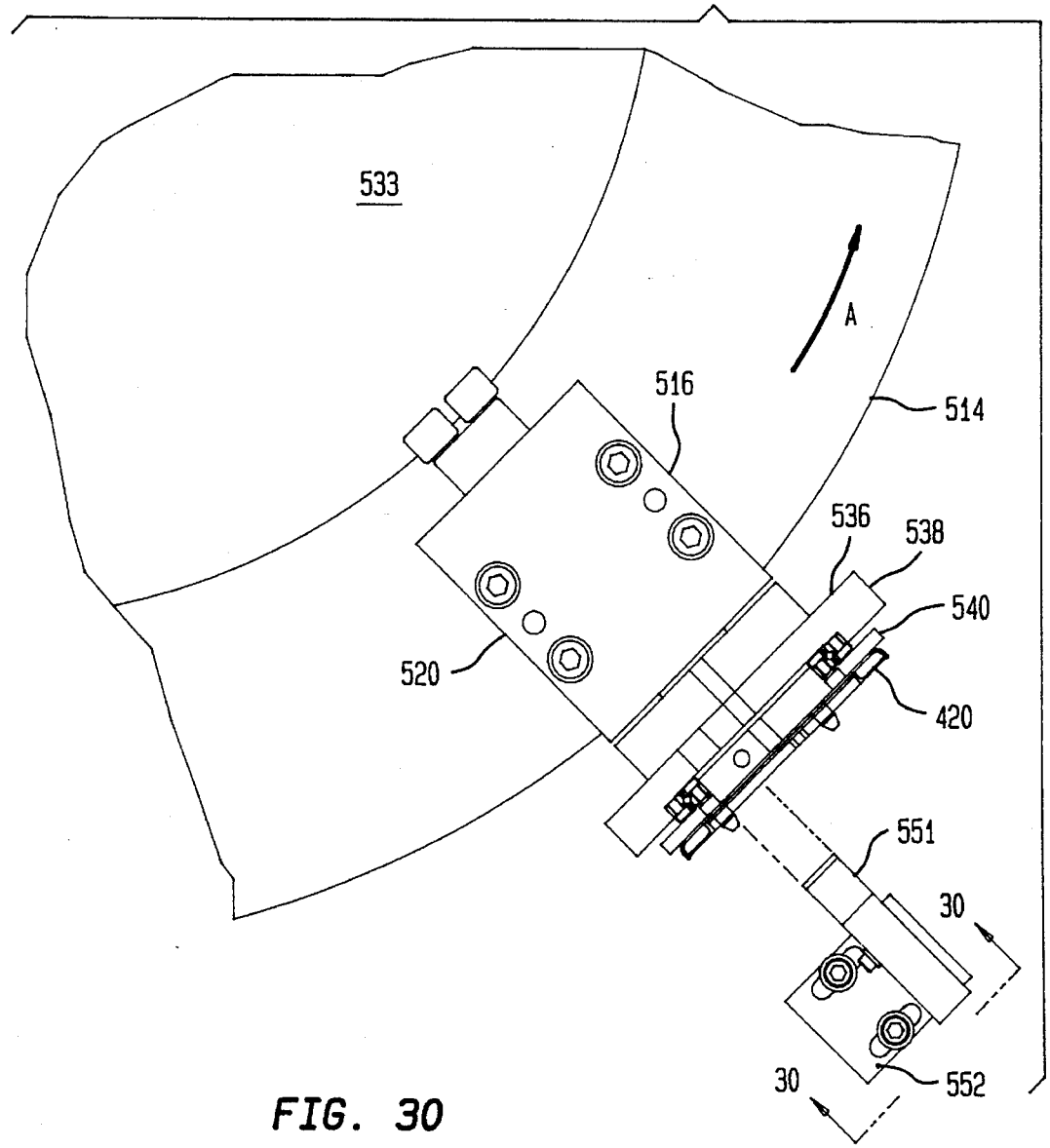
FIG. 29 illustrates, generally diagrammatically a package detector assembly operatively utilized in conjunction with the rotary disk as shown in FIG. 25.

(2) The second of the successive workstations located about the rotary suture wind and package turret 500, and, which may be optional on the machine, is the package detection station 450. The package or tray 420-detecting workstation 450, as shown in FIGS. 29 and 30, includes a suitable sensor 551 which is mounted on the arm of a stationary bracket arrangement 552 to provide assurance that a tray 420 has actually been physically positioned on the support surface or platform 542, and retained thereon by means of the guide pins 544 projecting radially outwardly through the apertures in the tray 420. This is indicated as step 43 in FIG. 3(c). Specifically, sensor 551 is interfaced with and adapted to provide this information to the control system 99 for the packaging machine as to the required presence of a tray 420 in order to enable subsequent packaging steps to be implemented by the packaging machine responsive thereto.

In summation, this particular workstation, which is essentially optional, has the sensor 551 positioned in front of the rotary dial 514, such that upon the platform 542 on the rotary turret mounting a tray being positioned in indexed alignment with the sensor, the latter may ascertain the presence of a tray 420 and its appropriate support on the guide pins 544 of the support platform 542. Upon a determination having been transmitted by the sensor to that effect to the operating and drive components (not shown) of the machine, the indexing rotary dial 514 is now in a condition to advance the tray on its support platform 542 to the next workstation, as indicated as step 45 in FIG. 3(c).

Needle-Suture Load to Package Station (3) The third workstation 600 (as indicated in FIG. 25) indexed in the direction of arrow "A" shown in FIG. 25 utilizes the multi-axis gripper 155 of the rotary swage dial 150 for inserting a specified number of surgical needles and attached sutures into the suture tray 420 indexed by the packaging dial 500 in a confrontingly opposed relation with the multi-axis gripper. The needles are fed by the multi-axis gripper 155 so as to be positioned on a suitable clamping structure constituting an integral portion of the suture package tray 420, such as raised components molded on the central bottom surface portion thereof, as shown in FIG. 46 of the drawings. A more detailed description may be found in copending patent application U.S. Ser. No. 08/181,598 assigned to the same assignee of the present invention and incorporated by reference herein.

Generally, the plate 540 and its support platform 542 mounting the tray on the guide pins 544 is indexed incrementally vertically, such as in upwardly spaced steps, along a relative displacement between elements 546a and 546b of the slide guides 546, and resultingly between the cam plate member 536 and plate 540, to ensure that the appropriate number of needles are positioned therein by multi-axis gripper 155 at their intended arrayed locations in the tray. This needle feeding action is facilitated through the program-controlled vertical incremental displacement between the plate 540 having the tray-supporting platform 542 thereon and the cam plate member 536 by the relative sliding movement taking place therebetween.

At the needle-suture load to package station 600, the each multi-axis gripper 155 of the rotary swage dial 150 successively positions and parks needles in the needle clamping structure formed in the center portion of the tray 420, as illustrated in FIG. 46 of the drawings.

Figure 31:
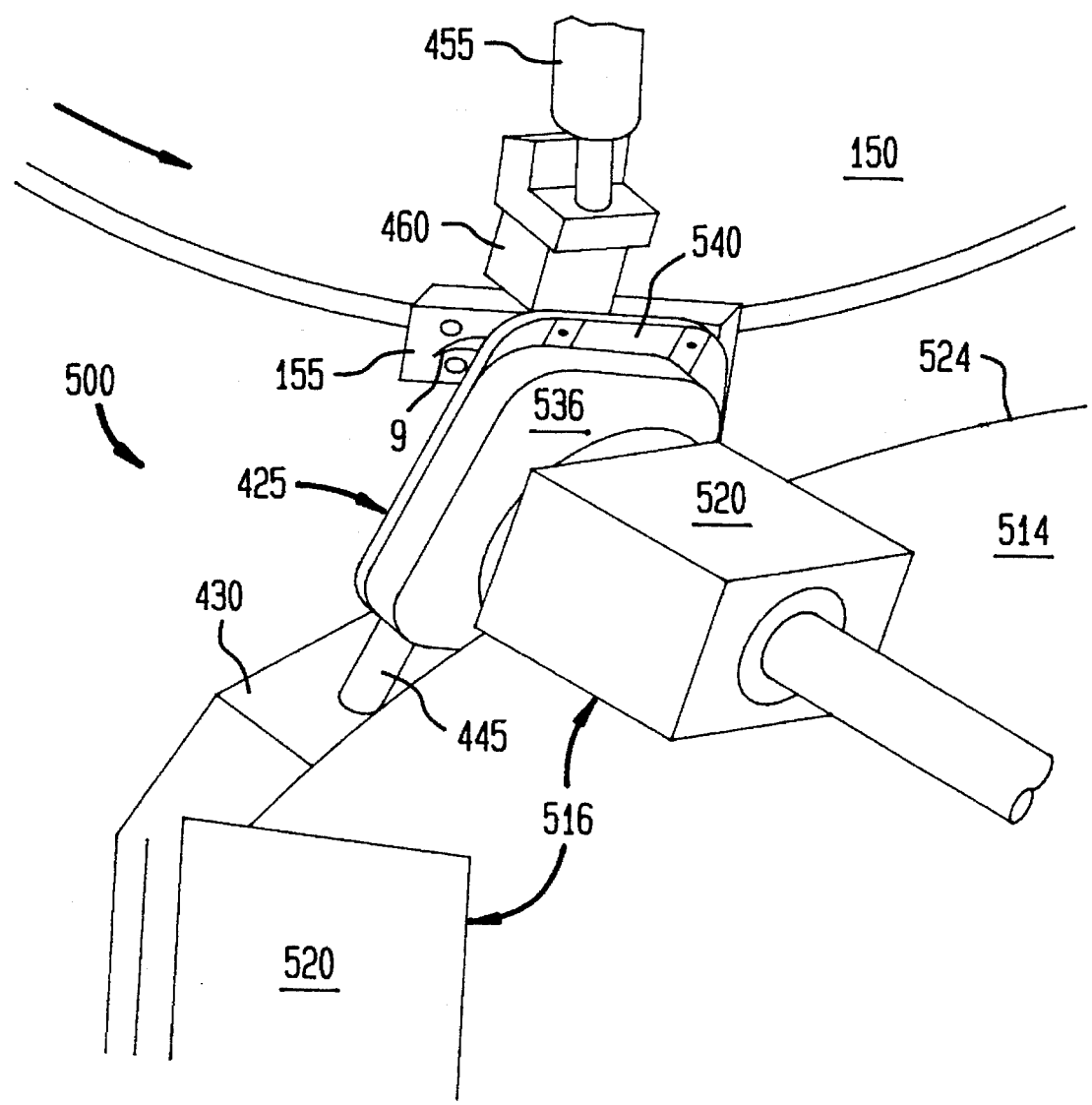
FIG. 31 is a perspective view of the discharge station 600 where rotary suture winding and packaging turret 514 indexes empty package 420 for receiving an armed needle from the multi-axis gripper 155.

As is illustrated FIG. 31, an empty tray 420 has been previously mounted on a tool nest 516 of the main rotary turret 500. The tool nest 516 includes the plate 540 having the tray-supporting platform 542 which may be registered in increments so that the empty tray 420 may receive eight (8) armed needles. While the preferred embodiment described herein describes the invention with respect to a reduced size organizer package (RSO) which is adapted to be supplied with eight (8) needles, it should be understood that the invention could be used with equal efficiency with a single-needle package or other amounts of needles.

Figure 32A:
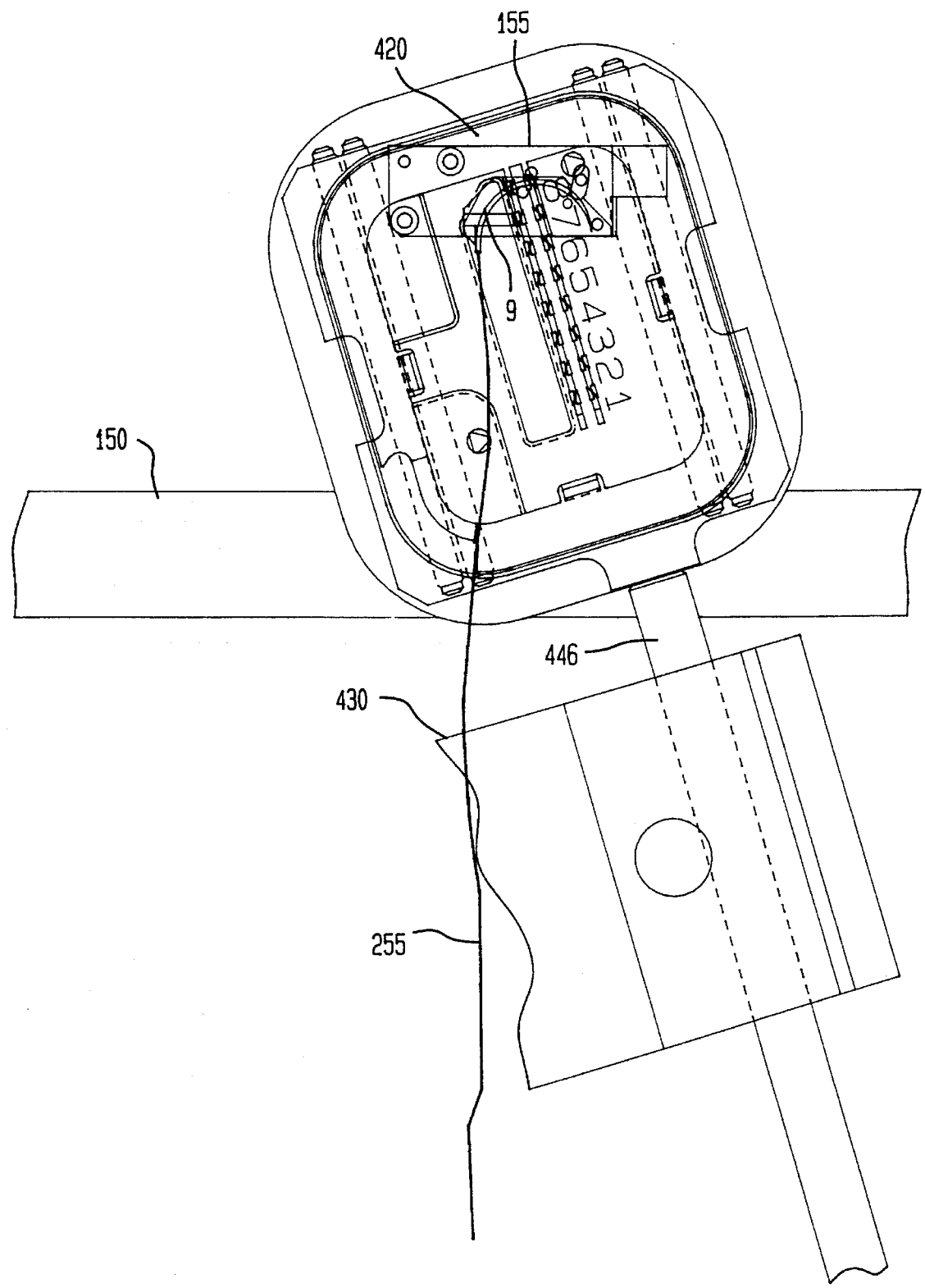
FIG. 32(a) illustrates, on an enlarged scale, the suture tray of FIG. 46 with the device for elevating the tray to enable a plurality of needles to be parked therein.
Figure 32B:
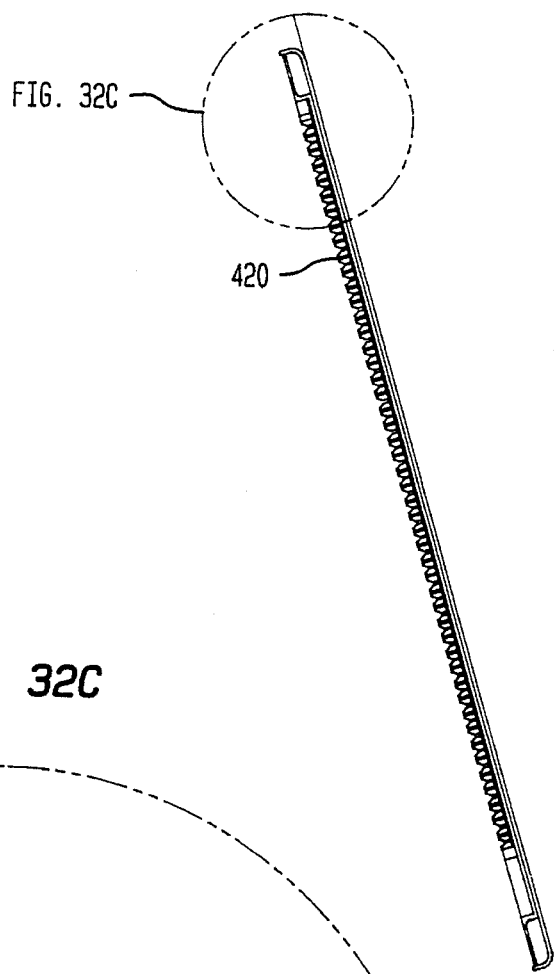
FIG. 32(b) illustrates a side view of the suture tray.
Figure 32C:
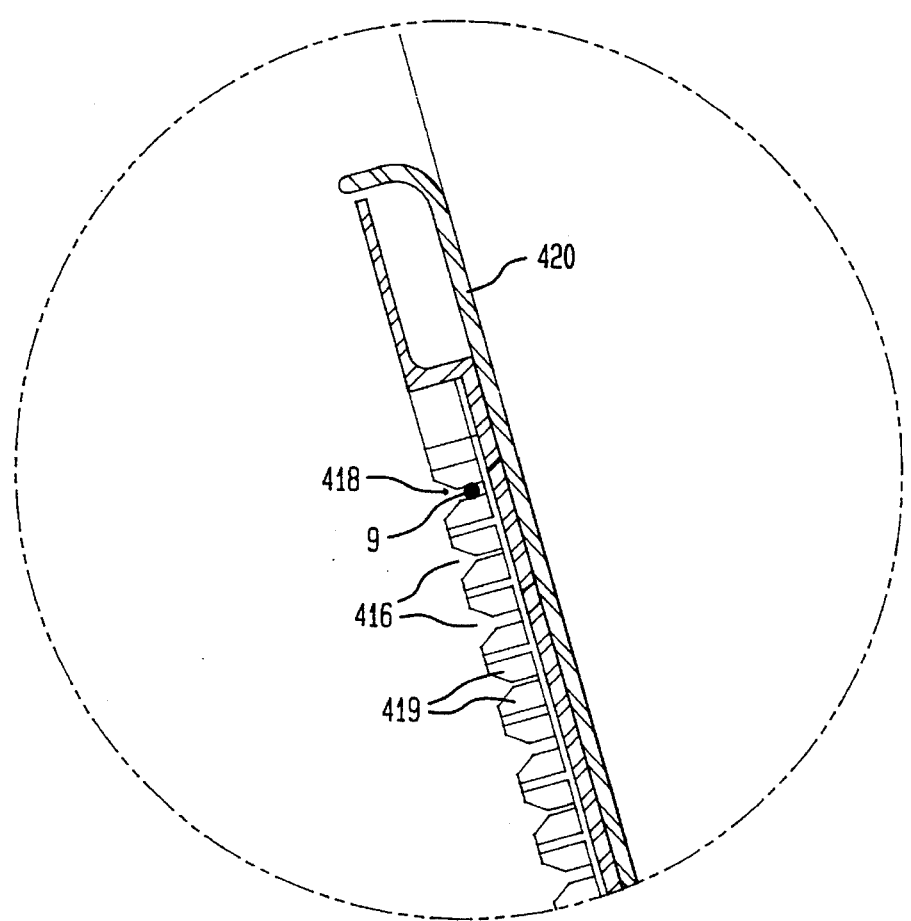
FIG. 32(c) illustrates an enlarged fragmentary view of the encircled portion of FIG. 32b.

The face of the empty tray 420 illustrated in FIGS. 32(a) through 32(c) shows a plurality of grooves between raised tray portions forming clamping structures for accommodating the sequential placement of eight armed surgical needles. In order to load the first armed needle into the empty tray 420, the tool nest 516 is indexed to workstation 600 as shown in FIG. 31. Simultaneous therewith, the rotary swage dial 150 as described in detail below, indexes the multi-axis gripper 155 to workstation 600. Then, the multi-axis gripper 155 is extended towards the empty tray 420 to deposit an armed needle 9 within a first pair 418 of the eight paired sets of needle receiving notches 416 that are formed between protruding portions 419 in the bottom surface of the tray. In the preferred embodiment, each paired set of notches 418 is consecutively numbered and spaced approximately 0.25 inches apart, as shown in FIG. 32(c). In the disclosed embodiment, the first needle 9 loaded is in the eighth position as shown in FIG. 32(a). As illustrated in FIGS. 31 and 32(a) through 32(c), the tool nest 516 assembly and, consequently, the empty tray 420 is slightly tilted counter-clockwise from the vertical with respect to the orientation of the multi-axis gripper 155 so that the curved needle will be accurately deposited within the notches formed in the package. This tilt, which may be about 10°–20°, and preferably 16° from the vertical, may be effected due to the contact between the cams 530 and an angled or sloped camming surface on cam dial plate 533 at workstation 600. As a result of this tilting offset, the needles are slightly shifted relative to each other, and the sutures depending downwardly therefrom will not tend to tangle with each other. Under control of the control system computer, a solenoid 455 then actuates a push rod 460 to depress the plunger on the multi-axis gripper 155 so that it may release its grip of the armed needle 9 in the manner described above.

As shown in FIGS. 31, 32(a) through 32(c), and 33(a) and 33(b), there is located at the workstation 600 a package elevator assembly 430 that registers the empty tray 420 to receive eight individual armed needles, one at a time.

As illustrated in drawings, the tool nest 516 includes the fixed body structure 520 containing the rotatable shaft 528 at which there is mounted the package tray holding platform or support surface 542 and the previously-described structure. Most of the turret stations, which as shown in FIG. 25 of the drawings are in this case eight (8) in number, require that the tool nest 516 is precisely maintained in a non-rotated vertical position, as illustrated specifically in FIGS. 26 and 28(a). This particular vertical orientation is maintained in that the circular stationary cam dial plate 533 extending between the collective workstations is contacted by the two cam followers 530, which are in the form of cam rollers 530a and 530b mounted on shaft 528 so as to straddle the longitudinal centerline of the latter, for each of the tool nests mounted on dial 514.

Figure 33A:
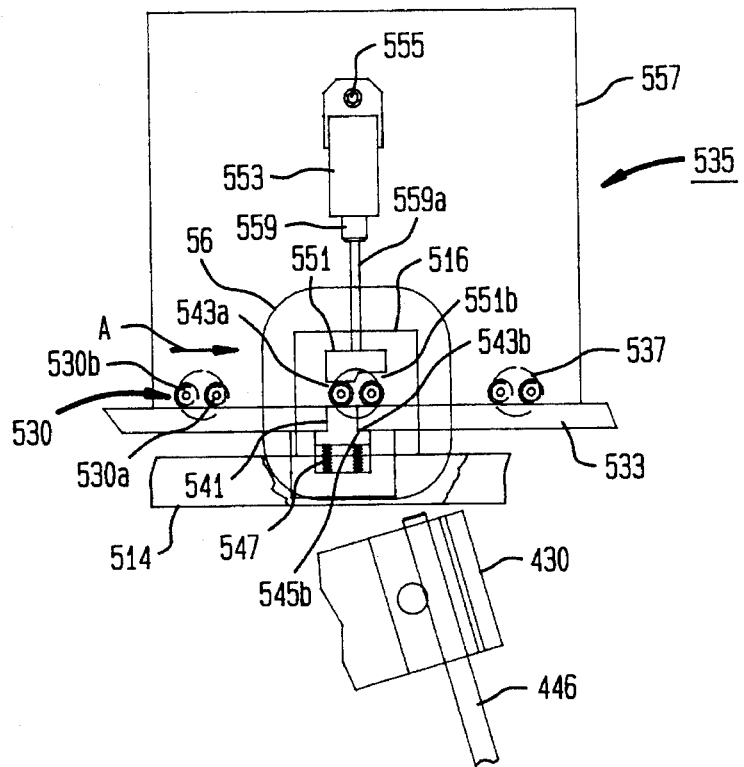
FIGS. 33(a) through 33(c) illustrate tilting mechanisms which are operatively associated with the tray elevating device of FIG. 32.

Prior to needle insertion at the needle inserting workstation, the tray 420 is adapted to be rotated into a tilted orientation through preferably an angle of 16° counter-clockwise so that needles are to be positioned in a correct array and orientation in the needle park structure of the tray. This is attained by a tool nest rotating structure, as illustrated in drawing FIGS. 33(a) and 33(b), operating in functional sequence essentially as follows:

FIG. 33(a) is an elevational view of the needle-suture load to package station 600 showing the indexing turret 514 upon which the tool nest 516 has been mounted, consisting of the tray holding plate 540, including the tray supporting surface or platform 542. The shaft 528 is mounted in suitable bearings, (i.e. 529a and 529b) so as to be freely rotatable within the housing 520 of the tool nest 516, if required to do so.

As a specific tool nest 516 which has the tray mounted thereon at the first workstation, and which is adapted to be supplied with the needles, enters the needle and suture load to package workstation, in the direction of arrow A, the tool nest 516 enters the tilt mechanism 535. The two cam followers 530, hereinafter designated as cam rollers 530a and 530b, roll along the upper surface of the stationary cam dial plate 533, as illustrated by phantom lines at the left-hand side, and then pass into the index mechanism 535 stopping in the position shown in solid lines in FIG. 33(b).

A track section 541 which consists of an insert having upper surface 543 normally in coplanar relationship with the upper surface of the cam dial plate 533, and which extends through a cutout 545 formed in the cam dial plate 533, has its uppermost position determined by shoulders 543a and 543b bearingly contacting against mating lower surfaces 545a and 545b on the lower side of the stationary cam dial plate 533. Normally, the track section 541 is biased upwardly into the cutout 545 under the urging of compression springs 547 which are supported against a suitable spring support member 549. At this position, the upper surface 543 of the insert 541 is in the same plane as the upper surface of the cam dial plate 533.

A displacement cam element 551 is in a normally raised position above the cam rollers 530a, 530b to enable the latter to roll into the index mechanism 535 workstation and enabling the tilting mechanism to operate without any interference of components in the rest or dwelling position, as illustrated.

In order to rotate or tilt the tool nest 516 for appropriate needle insertion, an air cylinder 553 of the mechanism 551, which is attached by means of suitable screws 555 to a plate structure 557 mounted above the camming dial plate 533; through a cylinder rod 559a of a piston device 559 causes the downward displacement of the cam element 551. This downward motion is guided by a suitable sliding device (not shown). The lower cam surface 551a of the displacement cam element 551 exerts a downward force against cam roller 530b which, in turn, forces the insert 541 to move downwardly within the cutout 545 provided in the cam dial plate 533, compressing the springs 547, and thereby rotating the shaft 528 in the housing 520 of the tool nest 516 counter-clockwise about axis 528a. The downward movement continues until the upper surface portion 551b of the displacement cam element 551 contacts the other cam roller 530a which has been displaced upwardly an amount equal to the downward displacement of cam roller 530b, and the system reaches the end of travel, causing the air cylinder to maintain the position, as shown in FIG. 33(a). The foregoing results in a rotational movement of shaft 528 to which the cam rollers 530a and 530b are fastened, and resultingly of the support surface 542 and tray mounted at the opposite other end of the shaft 528 in a counterclockwise direction, preferably to a tilting angle of 16°.

Figure 33B:
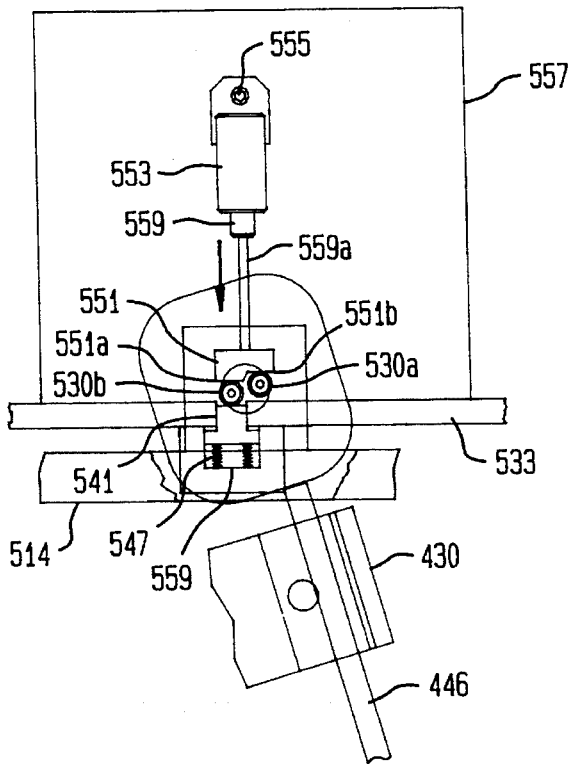

After completion of the needle insertion operation, this sequence is reversed in that the air cylinder receives compressed air so as to raise the displacement cam element 551. As a consequence, the springs 547 cause the insert 541 to be biased upwardly, causing the upper surface 543 thereof to press against the cam roller 530b and causing shaft 528 to rotate clockwise. This continues until the shoulders 543a, 543b contact the stationary surfaces 545a, 545b at the lower side of the cam dial plate 533, thereby stopping this rotational motion. This clockwise rotation of the shaft 528 causes the cam roller 530a to move a lower position until it contacts the upper surface 543 of the insert 541 which is now located in the same plane as the upper surface of the stationary cam dial plate 533. A suitable switch, for example, a proximity switch (not shown) now indicates that all of the mechanical components of this arrangement have been returned to the original position of FIG. 33(a), and the dial 514 indexes the tool nest forward for the next operating cycle. FIG. 33(b) shows a dashed line representation of the cam rollers 530a and 530b rolling on the surface of the tool cam dial plate 533 towards the right, and the shaft 528 being displaced from this workstation.

This aspect provides a structure of providing a rotary tilted positioning of a product on an indexing turret, in this application rotation of the shaft 528 and tilting the package or tray mounted thereon by means of the support plate 536 and platform 542, such as through an angle within the range of 10° to 30°, and preferably about 16°, due to the parallel offset distance between the camming surfaces 551*a*, 551*b* on the displacement cam element 551 which contact the cam rollers 530*a* and 530*b*.

Figure 33C:
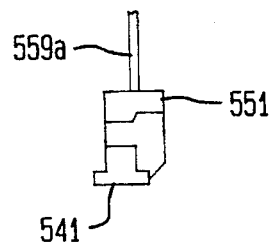

In FIG. 33(*c*) there is disclosed schematically an alternative design, similar to the foregoing, however, in which the individual structural components of the tilting arrangement are combined into an integral modular unit.

A shaft 446 of elevator assembly 430, as shown in FIG. 32(*a*), raises the plate 540 essentially vertically but slightly skewed (at about 11°) in 0.25 inch increments to sequentially receive eight needles from the multi-axis gripper 155 as described above. In this embodiment, the rotation of the swage dial 150 supplying armed needles from the pull-test station 300 at a rate of approximately 60/min. is synchronized with the vertical incrementing of the plate 540 mounting the tray 420 to maximize production rates. For example, after inserting the first armed needle 9 into the empty tray 420 into the paired notches numbered "8" as described above, the elevator shaft 446 raises the plate 540 vertically for 0.25 inches so that the next armed needle 9 may be deposited in the pair of notches 418 numbered "7." Simultaneous with the registering of the tool nest plate 540, the rotary swage dial 150 indexes the next multi-axis gripper 155 carrying the second armed needle, so that it may insert the next needle in the second position (notch "7") of the tray 420. This process takes place eight (8) times to fill a reduced size organizer package containing eight (8) armed surgical needles. After the eighth needle has been inserted in the package, the elevator assembly 430 retracts the elevator shaft 446 by conventional means such as a pneumatic air cylinder (not shown). Thus, the tray 420 which is now equipped with eight armed needles is in its initial position on the tool nest 516 and the tray is ready for further treatment at successive workstations.

Upon the requisite number of needles having been parked in the tray; for example, eight needles, the grippers 155 for transporting needles to the tray cease operation, and the rotary dial 514 indexes to the next workstation, while a subsequent tray may be positioned indexed in front of the needle dispensing unit so as to, in turn, be capable of being equipped with needles and attached sutures, as was the preceding tray 420.

Figure 34:
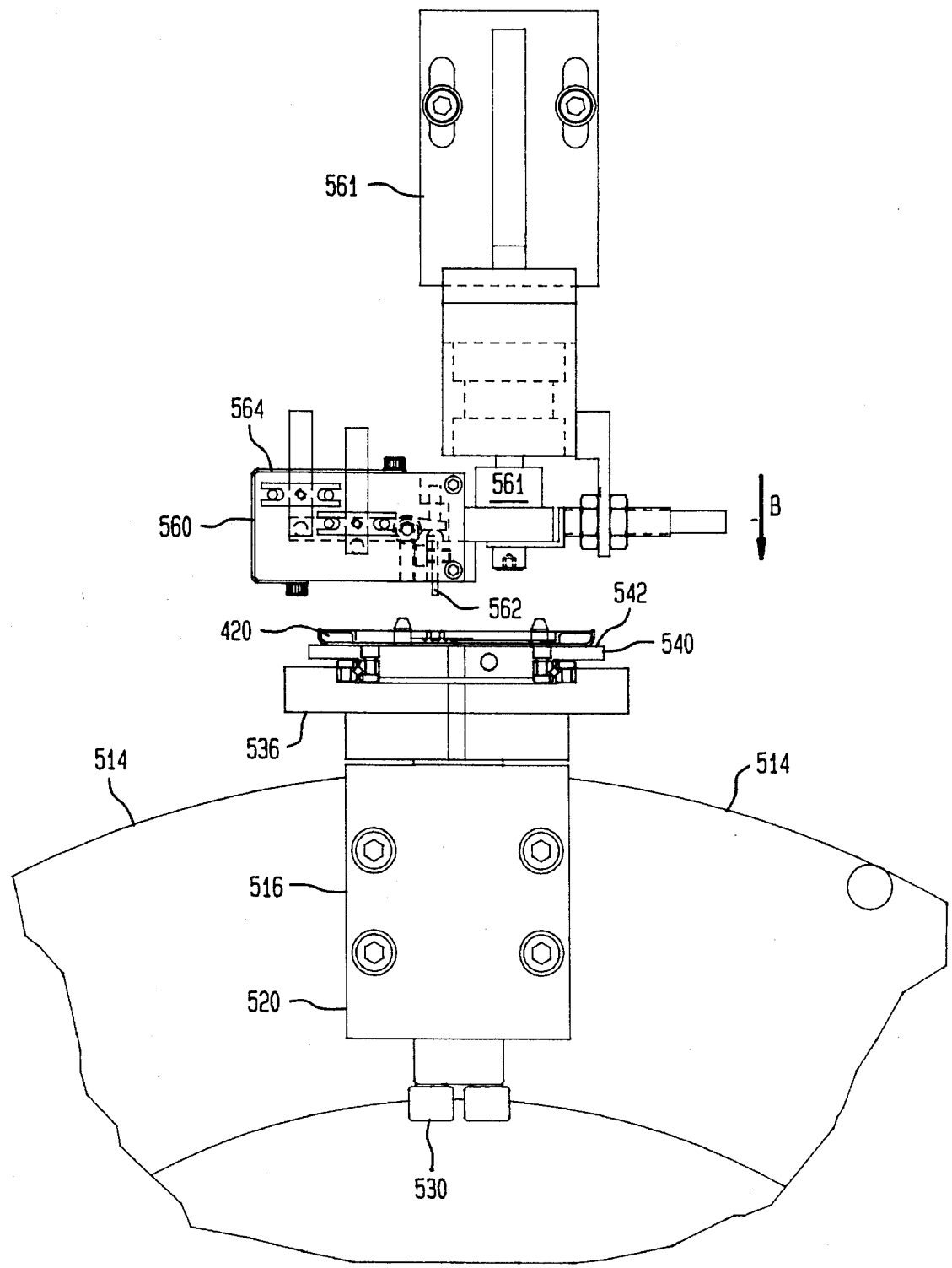
FIG. 34 illustrates a side view of the needle detector arrangement.

Needle Detecting Station (4) The optional fourth of the successive workstations located about the rotary suture wind and package dial is the needle detector workstation 475 which may be provided for verification of the presence and proper positioning of the needles and sutures having been introduced into the tray 420 by the multi-axis gripper 155, as described above. As shown in FIG. 34, needle detector unit 560 consisting of a stationary bracket unit 561 is adapted to be positioned opposite the platform 542 indexed in front thereof and mounting the needle-filled tray 420, and then advanced axially towards the latter to enable a plurality of sensors 562 mounted on a housing 564 movable thereon and interfaced with control system 99 to ascertain that the appropriate number of surgical needles have been properly introduced into and parked in proper array in the tray 420 by the multi-axis gripper 155 at the preceding workstation 600. Upon the needle sensors 562 verifying to the control system 99 the presence of the required quantity and parking of the surgical needles in the tray 420, the sensors 562 and housing 564 are retracted away from the tray 420 on platform 542 to enable the suture wind and packaging turret 500 to index the tool nest 516 forwardly to a further workstation.

Figure 35A:
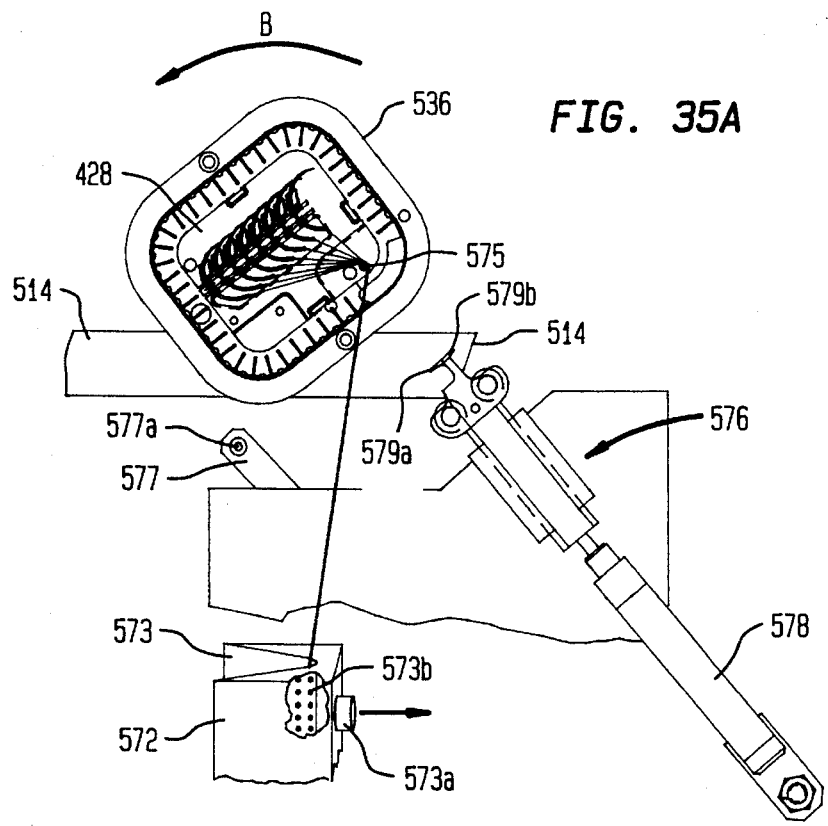
FIGS. 35(a) through 35(c) schematically illustrate, respectively, various stages in the operation of the suture winding arrangement.

Suture Winding Station (5) A suture winding workstation 550, to which the tray 420 is adapted be indexed, comprises a suture winding apparatus 570, by means of which sutures depending from the needles outwardly of and hanging downwardly from the tray 420 are wound into the confines of the tray 420, and particularly the peripheral channel as illustrated in FIG. 46, and as shown in FIGS. 35(*a*), 35(*b*), 35(*c*) and 36 of the drawings. The downwardly loosely hanging sutures extending from each of the needles, as described hereinbelow, are positionable so as to be tensioned in a stationary vacuum device or unit 572 located below the tool nest 516 supporting the suture tray 420 at this workstation, and to thereby cause the sutures to be tensioned and bundled into a compact strand, the operational sequence of which is illustrated in and described in more extensive detail hereinbelow with regard to FIGS. 35(*a*) through 35(*c*) of the drawings directed to the operational aspects of winding apparatus 570.

The cam plate member 536 of the tool nest mounting the needle and suture-filled tray 420 on platform 542 at this workstation is adapted to be contacted along the cam surface 538 thereof by cam follower components 574 located on a stylus arrangement 576 of apparatus 570, which is employed for guiding and winding the sutures into the peripheral channel of the tray 420. The stylus arrangement 576 includes a stationary cylinder 578 having a pneumatically-actuatable central piston 580 longitudinally reciprocable therein for movement towards and away from the tray 420. The cam follower components 574 comprise articulatingly connected rollers 574*a* and 574*b* contacting the peripheral cam surface 538 of the cam plate member 536, the latter of which, in conjunction with the support plate 540 mounting the tray 420, is rotated by the computer-controlled rotation of shaft 528 about a horizontal central axis 528*a* extending normal to the plane of the plates 536, 540 and the tray 420 so as to facilitate winding of the sutures into the peripheral channel of the tray 420, as shown and elucidated with regard to the description of operation of FIGS. 35(*a*) through 35(*c*) and 36.

Referring more specifically to the construction of the tray 420 shown in FIG. 46 of the drawings, which as indicated hereinabove is essentially the needle and suture-containing tray 420 constituting, in combination with an attached cover, the components of the multi-strand suture package of the above-mentioned copending patent application (Attorneys Docket ETH-849). Referring to the basic constructional features thereof, the tray 420 has a planar base 580 of generally rectangular configuration extending into rounded corners 582. Extending about the periphery of the base 580 is an upstanding wall 584, and spaced inwardly thereof in parallel relationship is a further upstanding wall 586 so as to form a peripheral channel structure 588 therebetween. Extending over the channel 588 outwardly from the inner wall 586 are a plurality of contiguously arranged essentially resilient retaining fingers 590, which are cantilevered so as to extend most of the way over the channel 588 from the upper edge of the inner wall thereof for preventing sutures from lifting up out of the channel. A gap 592 formed in the array of the retaining fingers 590 along the length of the channel, preferably proximate the juncture or corner between two of the rectangular sides of the tray 420 permits the end of each of the sutures to emerge from the channel 588, as shown in FIG. 46 of the drawings.

The central region of the base 580 of the tray 420 within the inner wall 586 includes integral structure which provides a plurality of spaced-apart gaps enabling the clamping therein of the suture needles so as to "park" the latter in the tray 420, as is clearly shown in the drawing and described in detail above, and with each of the needles having one end of a respectively associated suture attached or swaged thereto.

The functioning of the components of the stylus arrangement 576 for winding the suture into the tray 420 is described in more extensive detail in connection with FIGS. 35(*a*) through 35(*c*) of the drawings, illustrating more specifically the vacuum unit 572, a pivotable lever which is operable in conjunction therewith for tightening and tensioning the suture bundle, and the stylus arrangement 576 cooperating with the resilient fingers 590 of the tray 420 in order to feed the sutures into the channel in a winding motion as the tray 420 is being rotated by its supporting platform 542 due to rotation of shaft 528 about axis 528*a*.

Figure 37:
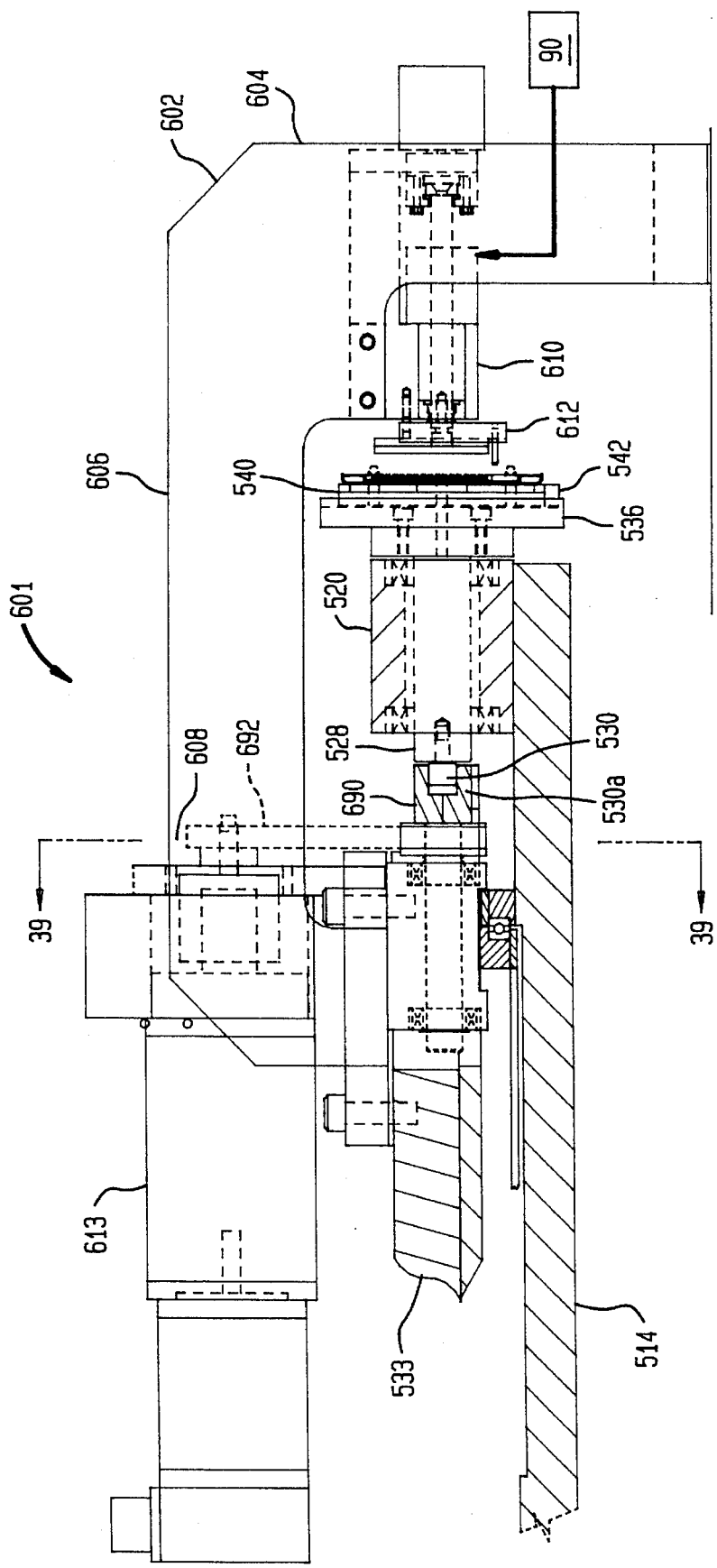
FIG. 37 illustrates a side view of a suture retaining unit in operative cooperation with the winding arrangement of FIGS. 35(a) through 35(c)
Figure 38:
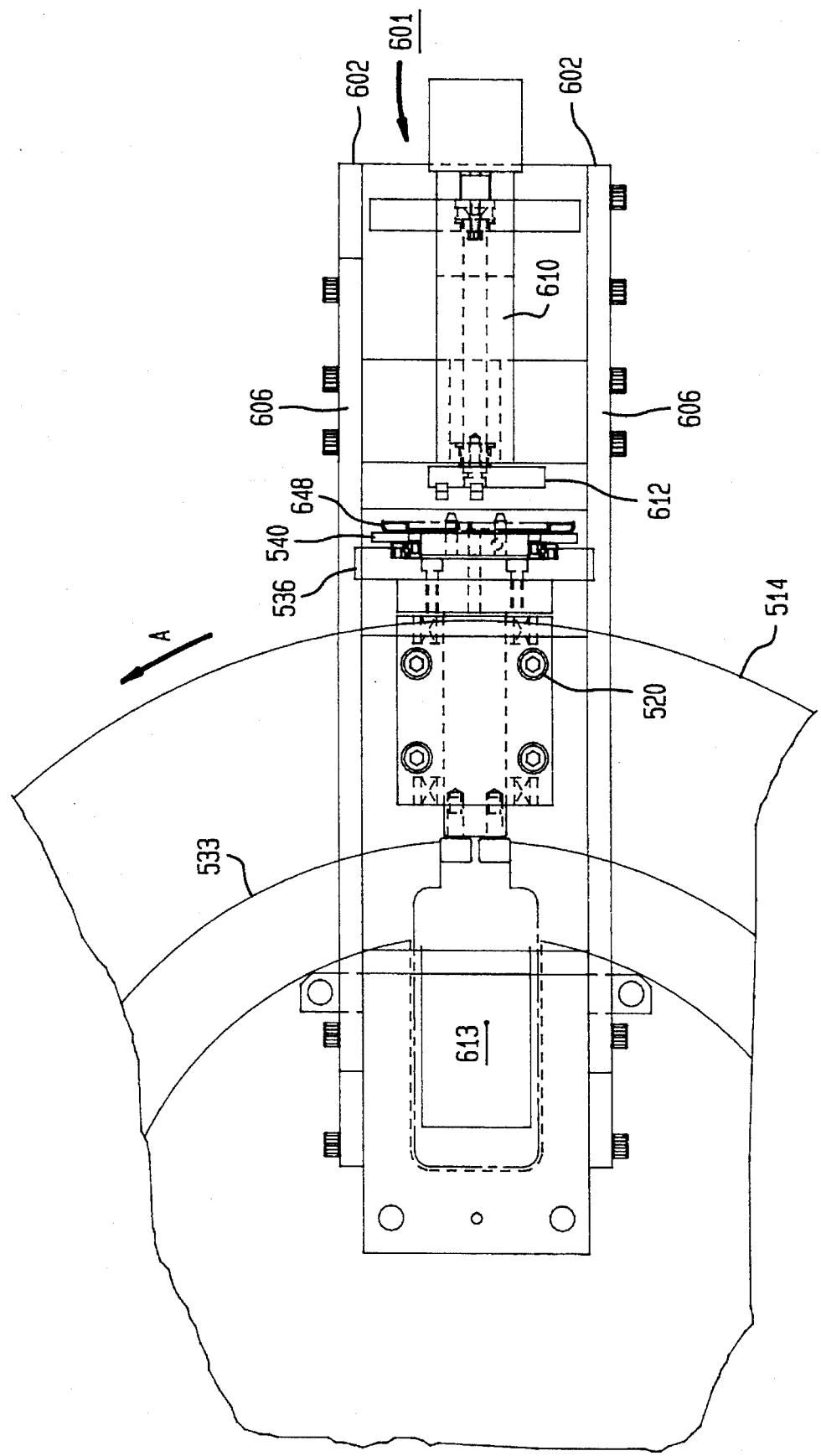
FIG. 38 illustrates a top view of the suture retaining unit of FIG. 37.

Adjacent the winding station and extending over the stylus arrangement 576 as shown in FIGS. 37 and 38 of the drawings, there is arranged a tray restraint device 601 which comprises L-shaped brackets 602 having upright legs 604 thereof fastened to a stationary surface, and top portions 606 extending horizontally over the rotary dial 514 and the dial cam plate 533 thereon, and being operatively connected through a suitable drive arrangement 608 with an inner end of the shaft 528 extending through the housing 520 and which is connected with the cam plate 536 and plate 540 mounting the suture tray. A shaft 610 extends through legs 604 of the stationary bracket 602 and upon initiation of the suture winding operation, is displaced axially towards the tray 420, either pneumatically or electrically by control means 99 such that a restraint plate 612 contacting the outwardly facing tray 420 surface comes into operative engagement with at least a center portion thereof so as to inhibit the tray 420 from being expelled outwardly from its mounted position on the platform 542 during the suture winding sequence, and, to prevent the sutures from being pulled out from their associated needles by the tension imparted to the bundled suture strands. The interengagement of the restraint plate 612 and the tray 420, and the rotation imparted to the shaft 528, will cause the shaft 610 in the leg member 604 of the bracket 602 of the restraint arrangement to rotate in conjunction with the rotation of shaft 528. Upon completion of the winding procedures, the control system 99 will cause the restraint plate 612 to be shifted away from the tray 420 into an inoperative position, so as to enable the tray 420 on its tool nest 516 to be indexed to a further workstation by the advance of the rotary dial 514 in the direction of arrow A of FIG. 38.

As shown in FIG. 35(*a*), the rotary dial 514 has just indexed to the suture winding workstation with a tray 420 attached to its platform 542. In this position, the bundle of sutures, in this instance, eight sutures each respectively attached to one of the surgical needles parked in the tray, hang downwardly from the tray and enter the vacuum gathering device 572 which has an internal V-section 573 wherein a generated vacuum applies tension to the sutures and collects and stretches them into a bundled strand. The vacuum is created by a vacuum being pulled from an exhaust port 573*a* which creates an airflow into the "V" shape through suitable vent holes 573*b*. The gathering of the suture bundle is indicated as step 61 in FIG. 3(*d*). Concurrently, as shown in FIGS. 35(*a*) through 35(*c*), the entire tray supporting platform 542 and cam plate member 536 are subjected to rotation about axis 528*a* in the direction of arrow B responsive to the operation of shaft 528 by means of a programmable servomotor 613, as illustrated schematically in FIGS. 37 and 38.

As shown in FIG. 35(*a*), the turret index which has moved the tray to the suture winding station is complete, and this motion has dwelled in preparation for the winding function for the sutures.

Figure 39A:
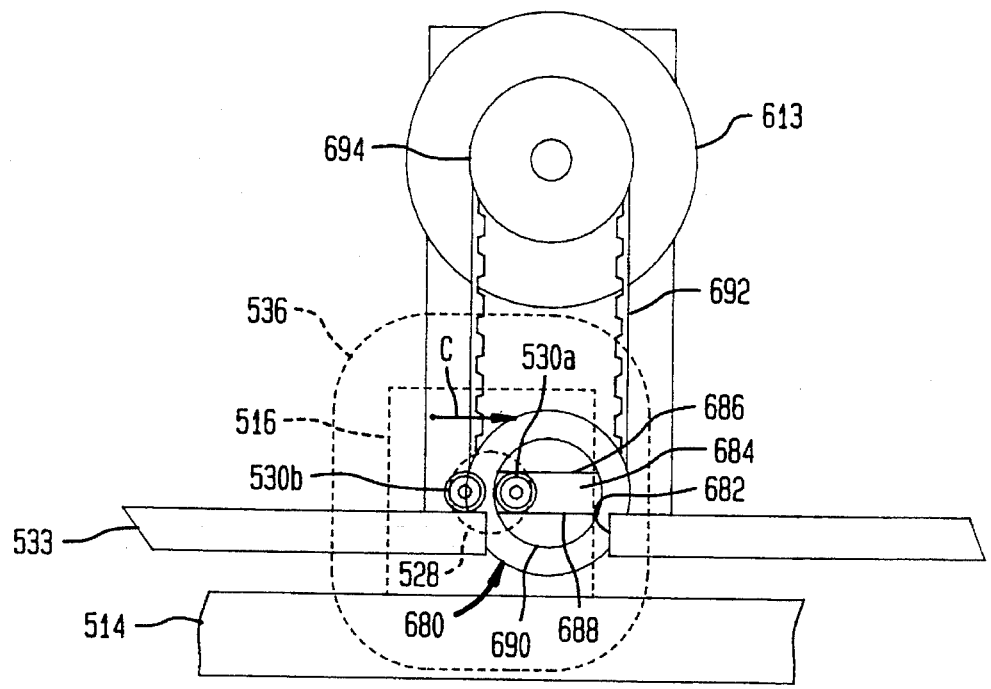
FIGS. 39(a) through 39(c) illustrate, respectively, operative drive structure for the suture winding arrangement, shown on an enlarged scale, taken along line 39—39 in FIG. 37.
Figure 39B:
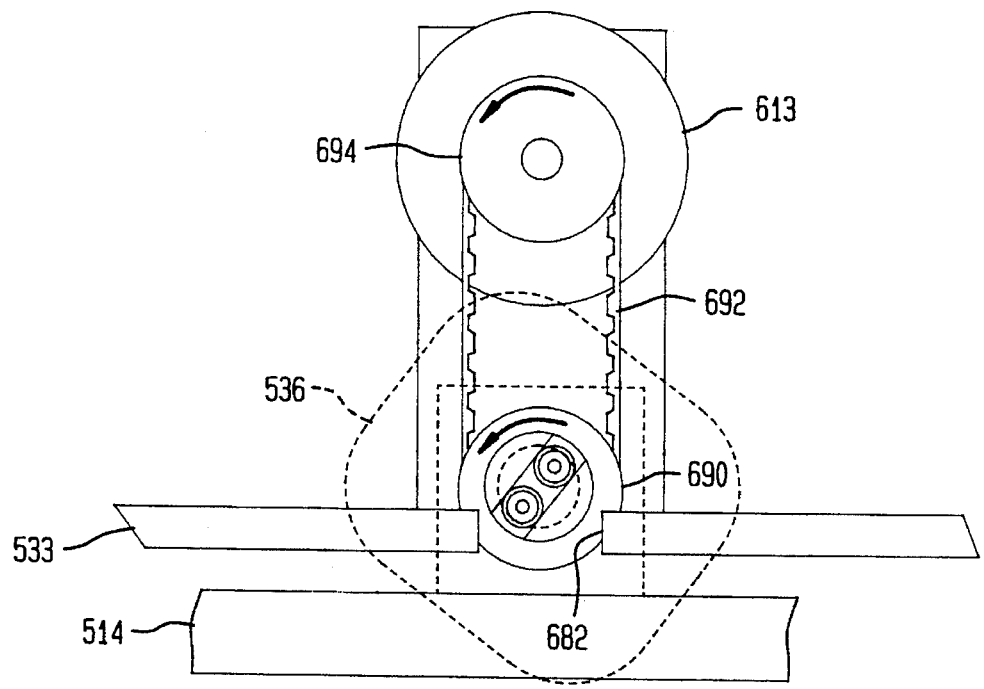
Figure 39C:
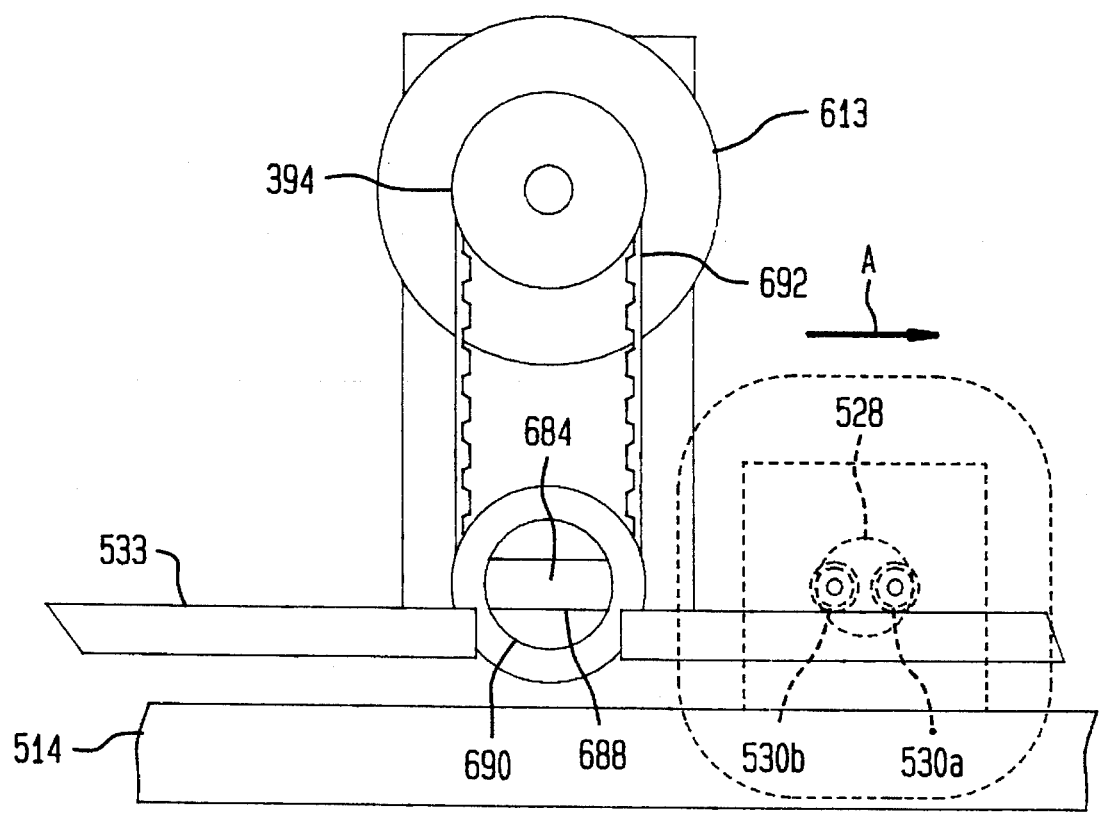

The suture winding workstation as illustrated in FIG. 25 of the turret 500 includes structure for rotating the package and to accomplish the suture winding operation. This is accomplished by a motorized driving mechanism as shown in FIGS. 39(*a*) through 39(*c*) and 37. The primary rotary dial 514 as shown in FIG. 37 which has the tool nest 516 thereon containing shaft 528 mounted in suitable bearings 529*a*, 529*b* in housing 520.

As the winding machine is indexed for a next suture winding cycle, the tool nest 516 is moved into the rotational station 680 as shown in FIG. 39(*a*), indicated by arrow C. The cam rollers 530*a* and 530*b* cross a gap 682 provided in the stationary cam dial plate 533 and enter a slot 684 formed by opposite parallel surfaces 686,688 formed in a driven roller 690, the latter of which extends partly into the gap 682 produced by a cutout provided in the cam dial plate 533. The lower surface 688 of slot 684 is normally substantially in coplanar and axial alignment with the upper surface of the cam dial plate 533 enabling the rollers 530*a* and 530*b* to be centered therein. This centering action takes place in a dwell position of the dial 514 in the suture winding workstation, whereby the longitudinal centerline 528*a* of shaft 528 is coincident with the centerline of the driven roller 690. The drive roller 690 is mounted in suitable bearings such as to be able to be rotated by the servomotor 613 driving a timing belt 692 extending from a driving roller 694 to the driven roller 690 so as to operatively interconnect the rollers 690, 694.

When the winding cycle is started at the suture winding station, as shown in FIG. 35(*a*), the servomotor 613 drives the driving roller 694 which, in turn, drives the driven roller 690 through the timing belt 692. At the end of the winding operation, the driven roller 690 is stopped to cause a horizontal orientation to be assumed by the slot 684 and the opposite surfaces of the slot are coplanar or coextensive with the upper surface of the cam dial plate 533. The dial 514 then indexes in the direction of arrow D, advancing the cam rollers 530*a* and 530*b* out of the slot 684 of the driven roller 690 and onto the upper surface of the tool camming plate 533, thereby locking the support plate and tray into a vertical tray orientation which is secured against rotation. A suitable switch, such as a proximity switch (not shown) assures that the driven roller 690 is in the horizontal slot orientation before indexing the dial 514 forwardly, thereby preventing any mechanical interference between components which could damage the latter. The rollers 690 and 694 may be suitable sprocket wheels, and the timing belt 692 a sprocket belt or chain.

The programmable servomotor 613 which rotates shaft 528 having the tool nest 516 fastened thereto and, effectively, the support platform 542 and cam plate 536 for the tray 420 about its center rotational axis 528*a* has completed an initial counter-clockwise rotation in the direction of arrow B, causing the suture bundle to wrap around a pin 575 which protrudes from the suture tray towards the viewer, when looking into the plane of the drawing. This rotation pulls the suture bundle partially out of the vacuum gathering device 572, which imparts a predetermined tension to the suture bundle causing it to become straight and the individual strands or sutures to be collected into a parallel and tightly confined group. The winding stylus assembly 576 which is mounted on a stationary plate is shown in its retracted position in cylinder 578, as it is during turret index.

Figure 35B:
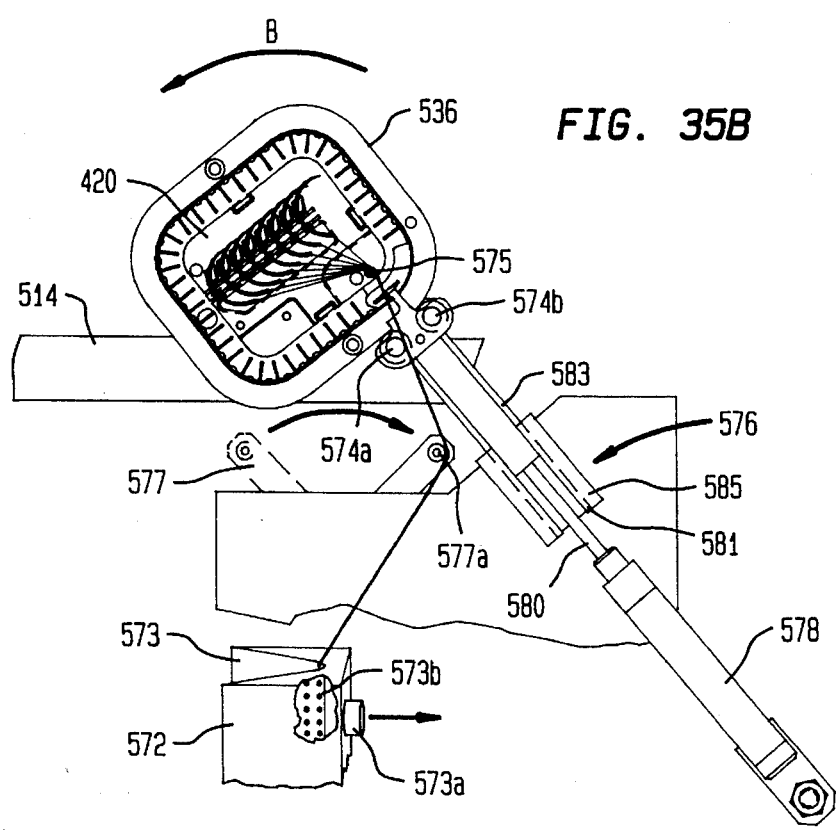

In FIG. 35(b), the subsequent phase of the winding operation is illustrated wherein a suture positioning arm 577 has been actuated to rotate clockwise, bringing a roller 577a to bear against the suture bundle, thereby implementing two functions:

(a) The suture bundle length is increased between the pin 575 and the vacuum device 572 causing additional suture length to be drawn out of the vacuum device and resulting in a tighter more confined suture bundle.

(b) Moreover, the foregoing displaces the suture bundle towards the right, so that a winding stylus 579 having fingers or legs 579a and 579b can straddle the bundle in the now extended position of the stylus arrangement, and be dropped on the floor of the tray channel 588 (in a motion perpendicular to the plane of view into the drawing) with a reasonable assurance that the bundle strands will not become pinched or fall outside of the stylus legs 579a, 579b.

FIG. 35(b) also illustrates the winding stylus assembly 576 extended towards the tray 420 by the extension of the air cylinder 581 until the stylus guide rollers 574a, 574b contact the peripheral cam surface 538 of the tool nest. This step is indicated as step 67 in FIG. 3(d). The air cylinder 581 maintains a force against the rollers 574a, 574b during rotation of the tray 420 for winding, acting in a manner of a spring as the rollers force the stylus head 579 and the slide 583 to oscillate. The slide oscillates within the stationary slide holder 585.

Figure 35C:
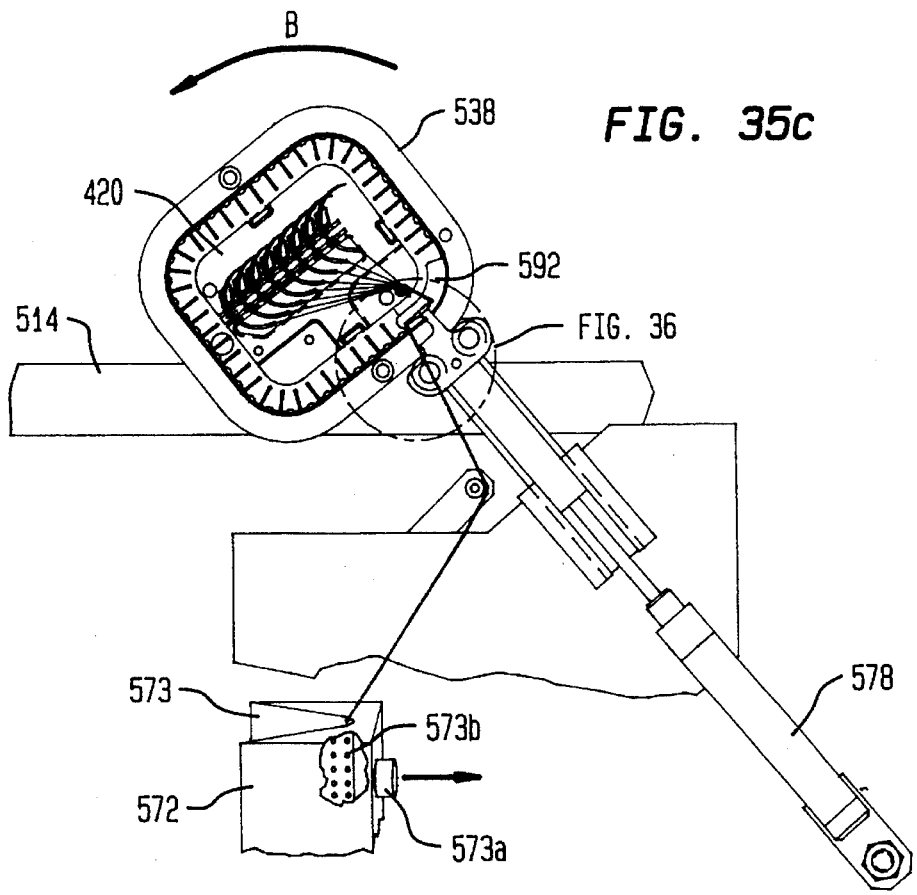
Figure 36:
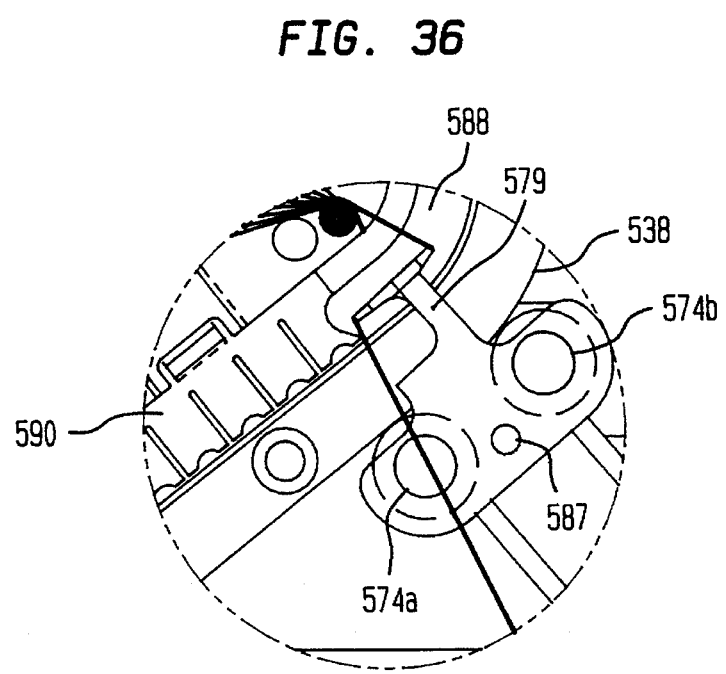
FIG. 36 is an enlarged fragmentary view of the encircled portion of FIG. 35c.

FIG. 35(c) illustrates the commencement of the tray rotation on the support surface 542 for effectuating winding of the sutures. The air cylinder exerts a constant force on the slide 583, and through a pivot pin 587 to the roller assembly 574a, 574b. The stylus 579, which is mounted in the roller assembly is maintained at 90° relative to the suture track by this action. The enlarged encircled detail view of FIG. 36 discloses the suture bundle after it is positioned below the resilient suture-retaining tray fingers 590. This also illustrates the manner in which the stylus 579 plows under the tray fingers, raising and lowering them progressively as it leads the suture bundle therebeneath and guides the bundle into the peripheral channel 588 of the tray 420. As this winding takes place, as indicated at step 70 in FIG. 3(d), the vacuum device 572 maintains a constant essentially gentle tension on the suture bundle as it is withdrawn therefrom, and this action continues until the suture bundle ends withdrawn from the vacuum device are fully inserted by the stylus 579 under the resilient tray fingers 590 into the peripheral suture tray channel 588. At this final point of the winding cycle, the tool nest 516 mounting the tray is rotated to position the stylus in the suture channel window or gap 592, as shown in FIG. 46, whereupon the stylus 579 is raised upwardly out of the tray and the air cylinder retracts the stylus assembly, i.e. the piston rod mounting the latter, to the position shown in FIG. 35(a). Rotation of the tool nest mounting the tray with the needles parked therein and the sutures wound into the channel 588 continues in a counter-clockwise direction until the needle park is vertical with the needle points extending downwardly. The rotary disc 514 is then indexed for the next cycle, in effect, for receiving and winding a subsequent tray.

During the foregoing suture winding sequence of operation, as previously mentioned, the restraint device 601 continually maintains its contact with the tray so as to prevent the tray and the contents therein from being expelled from the support platform 542 on which the tray 420 is mounted, and also to prevent the sutures from being pulled out from the needles. The restraint device 601 is withdrawn from the tray 420 upon completion of the suture-winding procedure to enable the continued forward indexing rotation of rotary turret 510. Additionally, drive member 530a and cam followers 530 located therein are returned to a horizontal position so the cam followers can leave the slot 684 and re-enter on top of cam plate 533 without mechanical interference as dial 510 indexes for the next cycle.

(6) At the above-mentioned optional workstation 625 of FIG. 1, the package tray 420 and its contents are exposed to external visual inspection to facilitate a viewer or video camera to ascertain whether any of the sutures extend outwardly of the channel or tray, and whether the needles are properly parked in the tray and attached to their associated sutures. This optional step is indicated as step 73 in FIG. 3(d).

Figure 40:
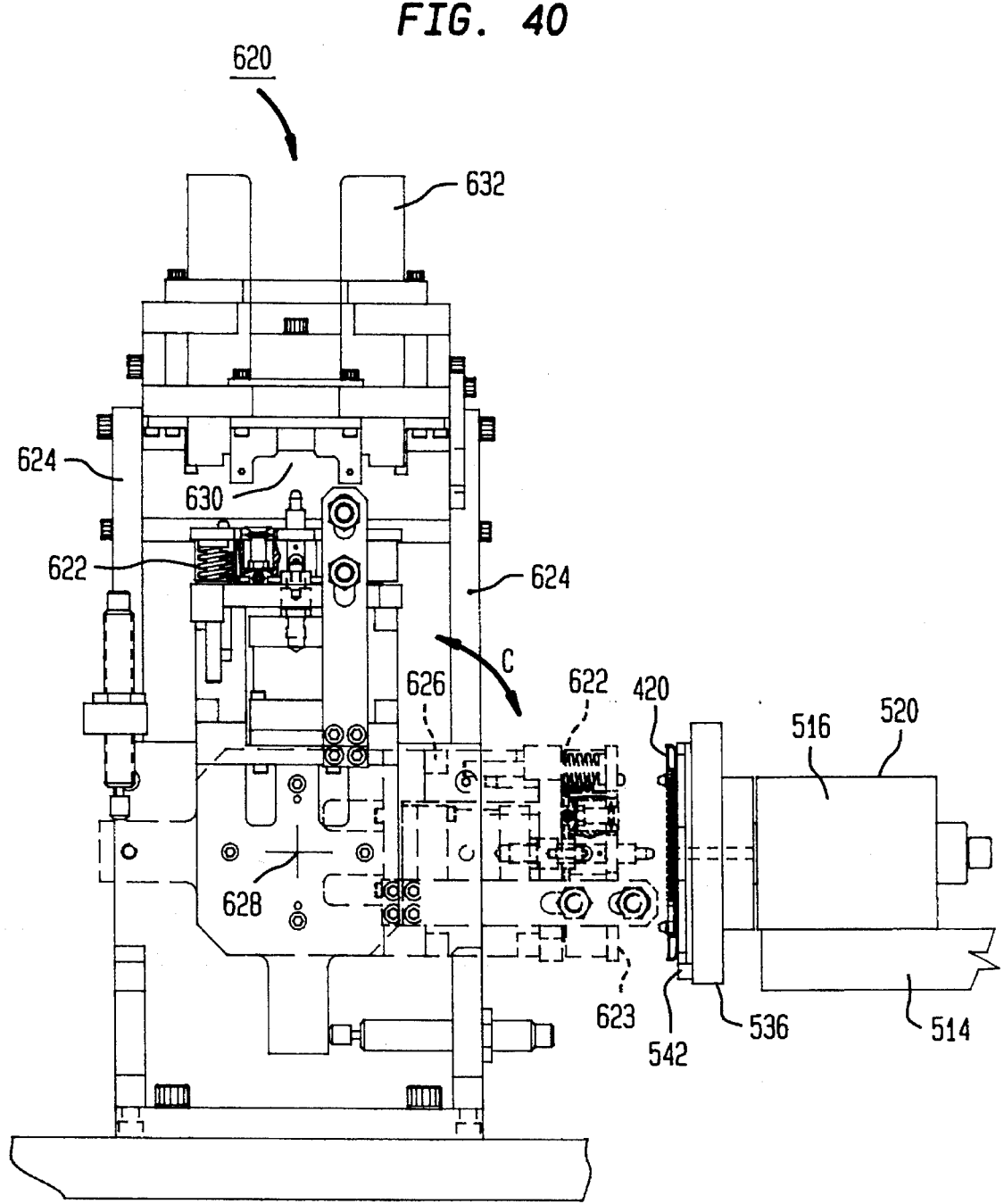
FIG. 40 illustrates a front elevational view of the cover applying device in two operative conditions thereof.
Figure 41:
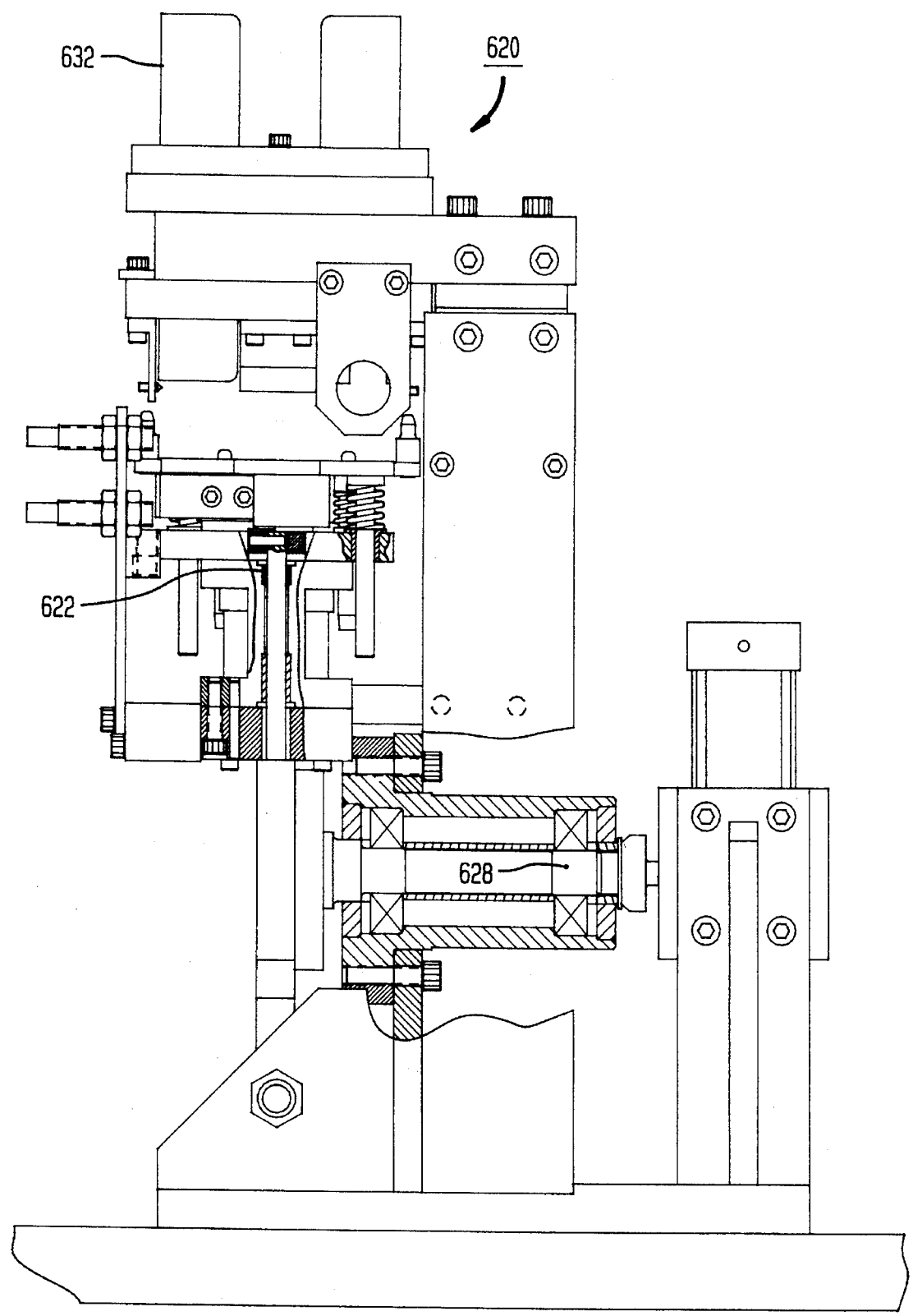
FIG. 41 illustrates a side elevational view of the cover-applying device of FIG. 40.
Figure 42:
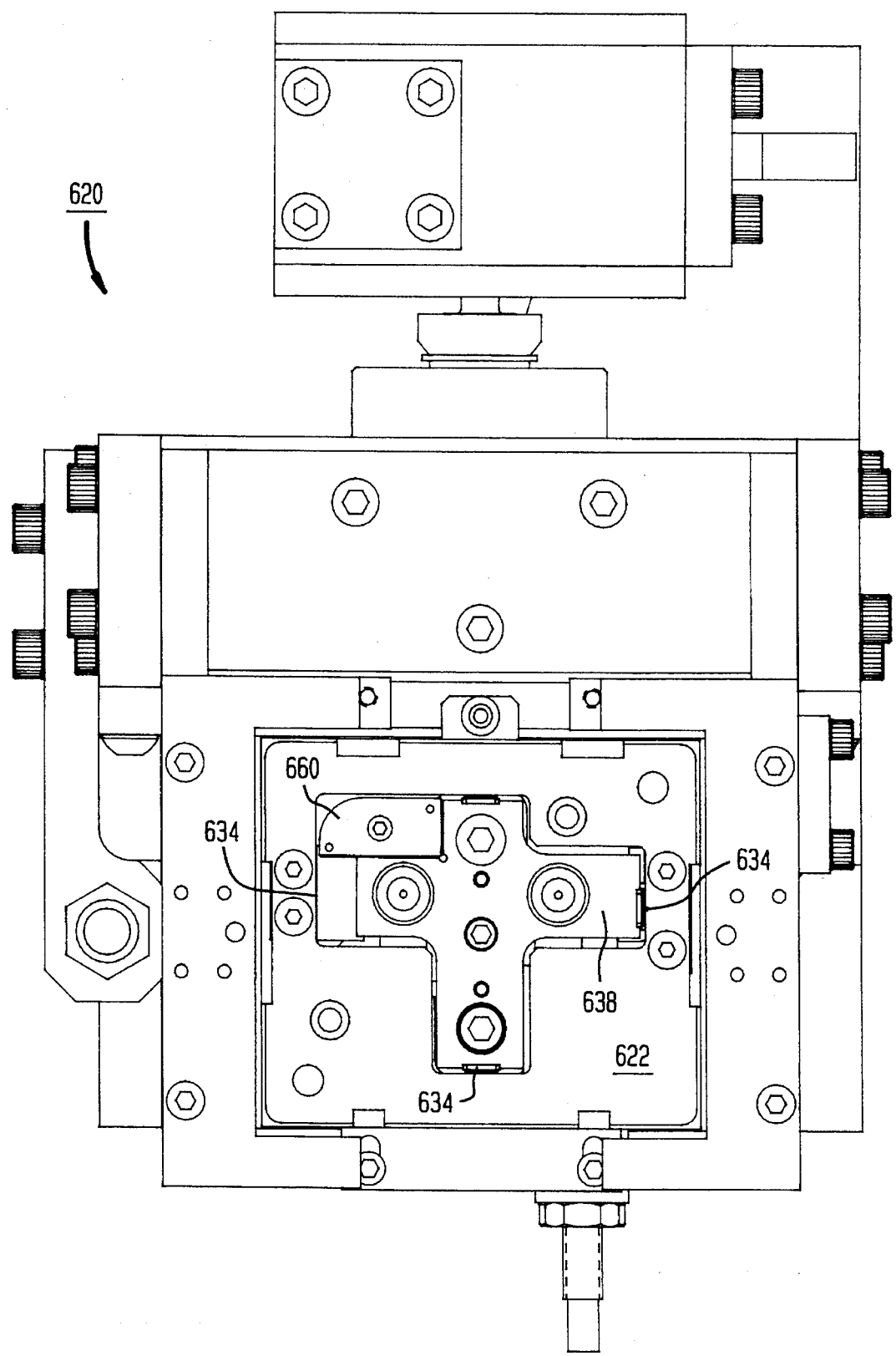
FIG. 42 illustrates a top plan view showing the cover-applying device and the cover-pressing die of FIG. 40.

(7) At a cover-applying and attaching workstation 650, as shown in FIG. 1, to which the tray 420 is to be indexed from the preceding optional inspection workstation, there is located a cover-applying apparatus 620 incorporating a pressing die structure 622 for attaching a cover to the tray 420, as illustrated in FIGS. 40 through 42 of the drawings, and for producing the suture package as shown in FIG. 47.

Figure 3D:
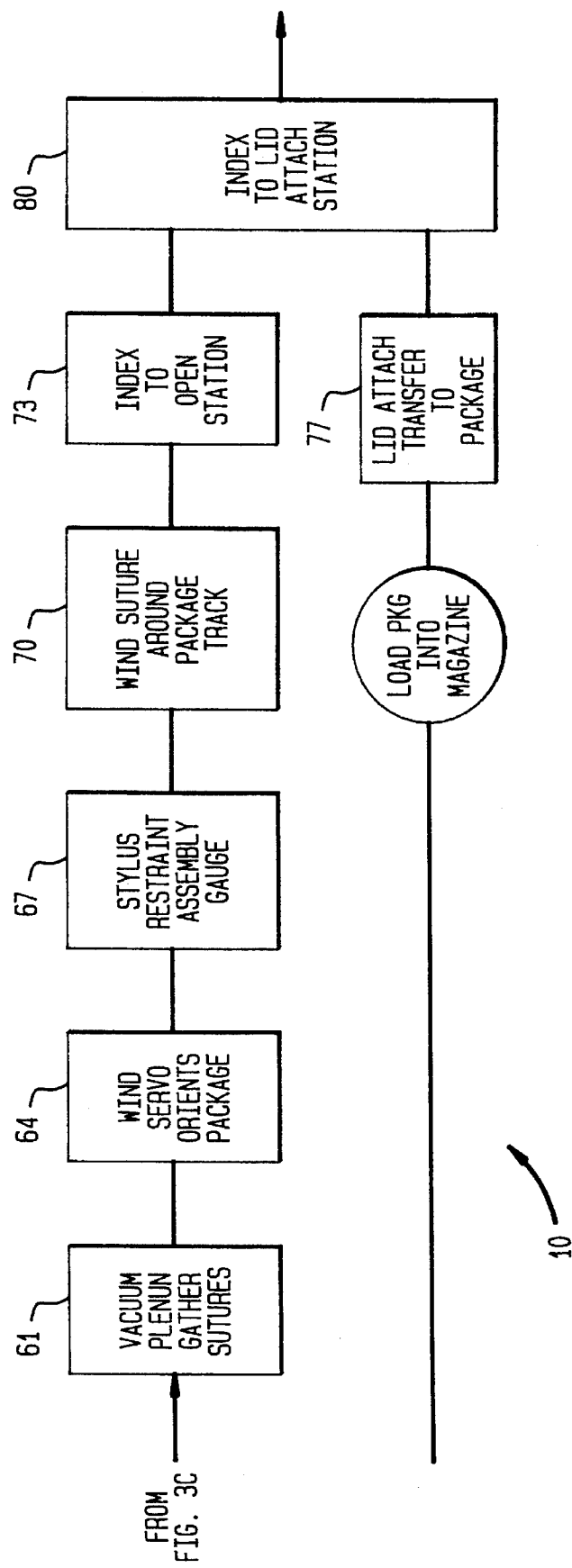

The process of attaching a cover to the package tray is indicated at steps 77 and 80 in FIG. 3(d).

The apparatus 620 which is essentially mounted on a suitable fixed support proximate to the perimeter of the rotary turret, includes an upstanding framework 624 which includes a pivot arm structure 626 pivotally mounted therein and being articulatable about a horizontal pivot axis 628 for movement between a vertical position facing the bottom end 630 of a cover supply hopper or chute 632 and a horizontal position facing a tray mounted on platform 542 which has been indexed to this workstation. For purposes of illustration only, in FIG. 40 both the horizontal and vertical positions of the pivot arm 622 are illustrated, as pivotable along the direction of double-headed arrow C. A cover pressing die 623 is mounted at the outer or free end of the pivot arm 626, with a plurality of resistant vacuum cups for engaging and holding the cover as it is withdrawn from hopper 632.

The pivot arm structure 626 with the pressing die 623 therein, when upright, is adapted to engage and withdraw a tray cover which is dimensioned in conformance with the configuration of the tray, and in the presence of a tray having the needles and wound sutures contained therein at the workstation, the pivot arm 622 with the pressing die 623 at its outer free end and the cover positioned thereon is swung into horizontal axial alignment with the tray on the support platform 542, as shown in FIG. 40, and through suitable actuating means, such as by means of a pneumatic device 628, the arm 622 with pressing die 623 thereon is extended towards and into contact with the tray on platform 542 so as to position the cover on the tray. The pressing die 623 contains suitable surface structure, as shown in FIG. 42, for fastening the cover to the tray, as explained hereinbelow.

The tray cover 651 is basically a flat cover which may be of a suitably imprinted paperboard or the like material, and is applied to be fastened to the tray 420 by means of pressing die 623, as shown in FIG. 47, with the outer dimensions of the cover as previously mentioned being substantially coextensive with the peripheral dimensions of the tray, and with the cover also having apertures 652 in registration with the upstanding guide pins 544 on the platform 542.

Figure 48:
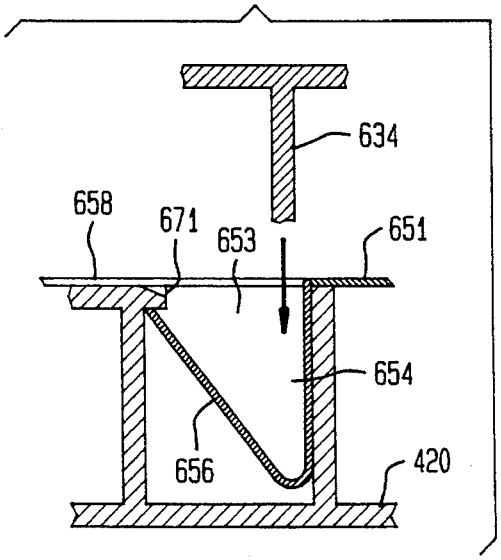
FIG. 48 illustrates, on an enlarged scale, a sectional view of one of the latching elements between the tray and an associated tray cover.

Hereby, the surface of the pressure die 623 facing the cover includes a first surface portion 638 substantially in conformance with the flat surface of the cover 651 which has been superimposed on the tray 420, and includes three projecting posts 634, preferably at three sides about the surface 638, and as shown in enlarged scale in FIG. 48 of the drawings, which will engage tabs 653 which overlie recessed portions 654 of the tray, and cause the pre-cut tabs 653 to be displaced along three edges thereof, and thereby forming latching tabs 656 which are pressed in V-shapes downwardly into the respective recesses 654 so as to have the separated edge of the folded tab 656 at that particular location engage beneath a horizontal wall structure 658 of the tray 420 extending partially over the recess 654, thereby latching the cover 651 into cooperative engagement with the upper surface of the tray at three locations.

Concurrently, a second raised die surface portion 660 on the surface 638 of the pressing die 623 engages into a surface region 662 defined by suitable raised wall structure 664 on the tray 420 shown in FIG. 46. Die portion 660 and wall 664 form therealong a peripheral mutually cooperating shear edge to separate a portion 668 from the cover 651 in conformance with the area 662. Second die portion 660 pushes the separated cover portion 668 downwardly into that area 662 of the tray so as to be secured therein separate from the remaining structure of cover 651. The separated portion 668 is permanently retained recessed within tray 420 by one or more ribs 671, as illustrated in FIGS. 46 and 48 which are formed in wall 664, so as to form a product-identifying label remaining in the tray upon subsequent detachment of the cover 651 from the tray 420.

Figure 45:
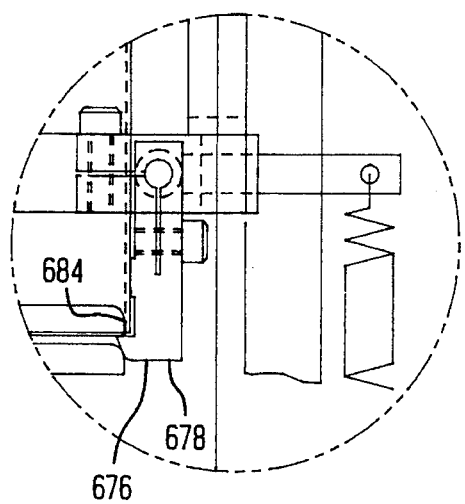
FIG. 45 illustrates, on an enlarged scale a fragmentary view of the encircled portion in FIG. 43.
Figure 43:
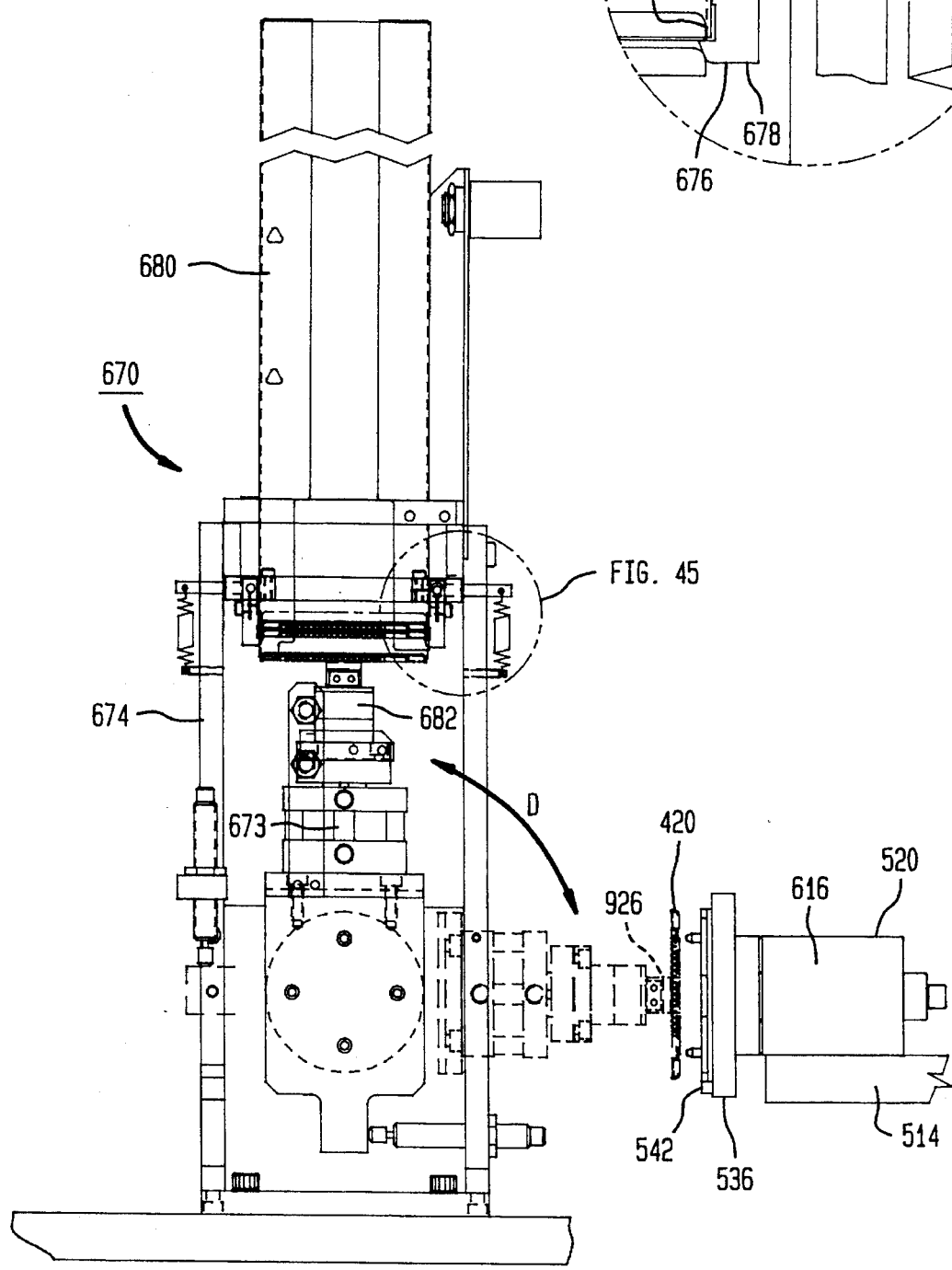
FIG. 43 illustrates an elevational side view of a suture package unloading arrangement in two operative conditions thereof.
Figure 44:
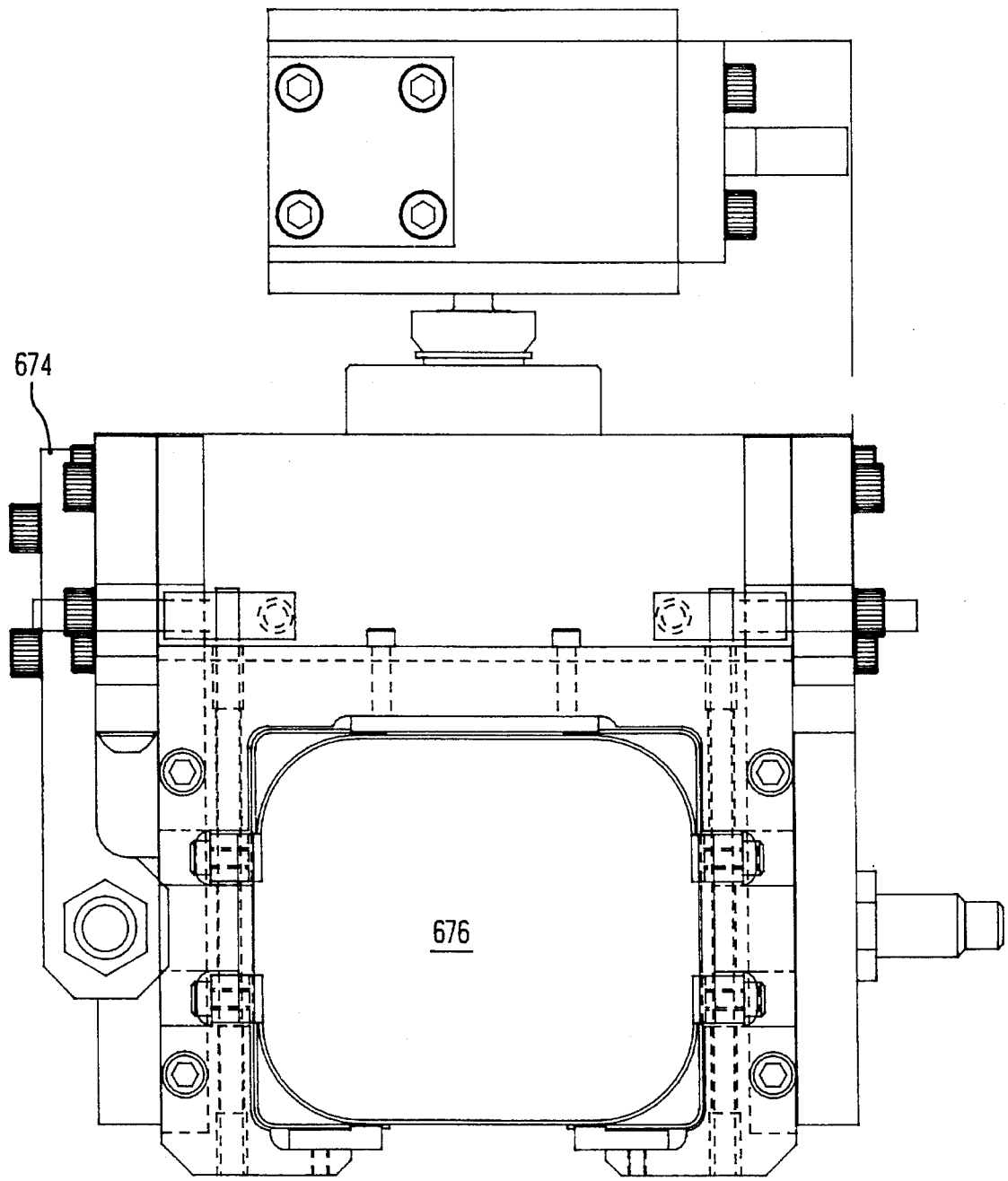
FIG. 44 illustrates a view in the direction of the arrow 44—44 in FIG. 43.

(8) Responsive to indexed forward rotation of the rotary dial 514 of suture wind and package machine 500 to a successive workstation, the suture package consisting of the needle and suture-containing tray 420 and attached cover 651, as shown in FIG. 47, is positioned in alignment on the platform 542 with a package removal unit 670, as illustrated in FIGS. 43 to 45 and indicated at step 83 in FIG. 3(e). In FIG. 43 of the drawings, a pivoting arm structure 673 is illustrated in both its horizontal and vertical operative positions, being pivotable along the direction of double-headed arrow D. Suitable grippers 926 are mounted on the pivoting arm structure 673 which is journaled on a stationary frame 674 the latter of which is somewhat similar in structure to the framework 624 of the cover-applying apparatus 620. These grippers 926 are pivotable into a horizontal orientation and extend outward from arm 673 as a result of pneumatically operated ram 682, as shown in FIG. 43, for gripping engagement with the suture package. The ram 682 and gripper 926 is then operated to retract and withdraw the suture package from its support surface or platform 542 and the pins mounted thereon.

Prior to unloading the completed package, a check is made as to the status of an error bit flag that may have been set during the non-destructive suture pull-test depending upon if the suture pull-test has failed. Similarly, at the needle detect station 475, a reject bit may or may not have been set indicating that the package does not contain the proper amount of needle-suture assemblies. Therefore, if it is determined that the reject bit had been set indicating a rejected package, the control system 99 will command the unload package gripper fingers 926 to release its grip on the package, and, essentially, drop the package into a reject bin as indicated at step 89 in FIG. 3(e).

The gripper 926 with the therewith clamped suture package is then adapted to be pivoted upward into a vertical orientation in alignment with the opening 676 in the bottom 678 of a hopper or chute 680 for receiving a stack of completed suture packages through the upward pushing action of a pneumatic cylinder 682 biasing the suture packages into the chute 680, as shown in FIGS. 43 and 45 and indicated as step 87 in FIG. 3(e). The bottom 678 of the chute includes a retaining lip 684 to prevent the suture packages from falling downwardly out of the chute. Subsequently, the biasing ram 682 and gripper 926 is pneumatically retracted within the arm structure 673 which is pivoted to its horizontal position to receive the next completed suture package. Alternatively, this particular, basically optional structure for removing the completed suture package from the support surface may be eliminated, if desired, and replaced by a manual suture package-removing operation.

From the chute 680, the suture packages may then be removed either through the intermediary of a further mechanism (not shown) or manually transported for additional processing; for example, such as sterilizing, and/or additional overwrapping, or the like.

While the invention has been particularly shown and described with respect to the preferred embodiments thereof, it will be understood by those skilled in the art that the foregoing and other changes in form and details may be made therein without departing from the spirit and scope of the invention, which should be limited only by the scope of the appended claims.

What is claimed:

1. An automated machine for attaching definite length sutures to surgical needles, each needle having a suture receiving opening formed therein for receiving a free end of a definite length suture to form a needle-suture assembly, and for packaging a plurality of successively formed needle-suture assemblies in a package tray, said machine comprising:

(a) a first workstation including means for sorting a plurality of needles and orienting each needle for automatic and sequential feeding thereof to a subsequent workstation;

(b) a second workstation for successively forming said needle-suture assemblies including means for automatically cutting an indefinite length of suture material to form individual definite length sutures, each individual definite length suture corresponding to an individual needle fed from said first workstation, and means for automatically and successively swaging each individual needle to close said suture receiving opening thereof about said free end of a corresponding definite length suture to secure said definite length suture thereto;

(c) a needle packaging station including means for sequentially receiving said formed needle-suture assemblies in a package tray, each individual needle-suture assembly being received while a needle-suture assembly is formed at said second workstation, said needle packaging station having a means for automatically winding definite length suture portions depending from said needle-suture assemblies into said package tray, (d) a first indexing means for sequentially receiving individual oriented needles fed from said first workstation and sequentially transferring each of said individual needles from said first workstation to said second workstation to form needle-suture assemblies thereat, said first indexing means sequentially indexing said needle-suture assemblies from said second workstation to said needle packaging station, whereby unsorted needles and an indefinite length of suture material are automatically formed into a plurality of oriented needle-suture assemblies and positioned within said package tray to facilitate their orderly removal therefrom.

2. The automated machine as claimed in claim 1, wherein said means for sorting comprises:

(a) infeed means for randomly depositing a predetermined amount of needles upon a first conveyor means;

(b) first means for obtaining an image of said needles deposited upon said first conveyor means, said means including digitizing means for converting said image into digital signals;

(c) computer control means for processing said digital signals to obtain positional and orientation data for selected randomly positioned needles upon said first conveyor means; and (d) transfer means for removing one or more said selected randomly positioned needles from said first conveyor means and positioning said needles upon a second conveyor means for conveyance thereof, wherein said transfer means grasps each of said one or more said selected randomly positioned needles in accordance with its respective positional and orientation data.

3. The automated machine as claimed in claim 1, wherein said second workstation further comprises:

(a) a drawing frame, said frame having first and second longitudinal guide members and defining a drawing axis parallel thereto;

(b) means for feeding a flexible indefinite length suture strand to said drawing axis for drawing and cutting;

(c) first and second gripping means for gripping said indefinite length suture strand and drawing it along said drawing axis, said first gripping means mounted for reciprocal movement on said first longitudinal guide member and said second gripping means mounted for reciprocal movement on said second longitudinal guide member; and (d) said second gripping means reciprocal to a start position along said drawing axis and below said cutting means, while said first gripping means is drawing said indefinite length suture strand to an insertion zone located a predetermined distance beyond said means for cutting, whereby said indefinite length suture strand is inserted within the suture receiving opening of an individual needle and cut to a predetermined length by said cutting means after said second gripping means has gripped said indefinite length suture strand at said start position.

4. The automated machine as claimed in claims 1 or 2, wherein said means for swaging comprises:

(a) first and second swage die means, said first swage die means fixed in position and having an end thereof defining a portion of a swage die opening, and said second swage die means having an end thereof defining another portion of said swage die opening, said second swage die means reciprocally movable toward and away from said first fixed swage die means, said end of said second swage die means positioned next to said end of said first swage die means to form said swage die opening for receiving said suture receiving opening of each individually fed needle; and (b) means for moving said second swage die means laterally away from said first fixed swage die means prior to receiving each said individually fed needle within said swage die opening, and further moving said second swage die means toward said first fixed swage die means to grip the suture receiving opening of an individual needle placed therebetween, said means for moving further including means for supplying adequate force to drive said second swage die means toward said first swage die means for each needle fed to accomplish swaging of said suture receiving opening of said individual needle about said free end of said definite length suture.

5. The automated machine as claimed in claim 4 wherein said first indexing means includes multi-axis gripper means for sequentially receiving and engaging each individually fed needle in an oriented position and for positioning said suture receiving opening of each said individually fed needle within said swage die opening prior to swaging thereof.

6. The automated machine as claimed in claim 4 wherein said swaging means further includes means for adjusting the position of said first fixed swage die means to change the amount of swage deformation occurring to a suture receiving opening during swaging thereof.

7. The automated machine as claimed in claims 1 or 2 wherein said means for sequentially receiving said needle-suture assemblies further includes:

(a) package tray support means for supporting said package tray; and (b) means for successively registering said package tray support means and said package tray supported thereon in incremental movements correlating with the sequential indexing of said needle-suture assemblies to said package tray, wherein said first indexing means successively transfers said needle-suture assemblies to said package tray with a single needle-suture assembly transferred at each registered position.

8. The automated machine as claimed in claim 1 wherein said first indexing means includes a first rotary turret, said first and second workstations stationarily spaced about the periphery of said first rotary turret, said machine further including a second indexing means comprising a second rotary turret for sequentially indexing said package tray having said needle-suture assemblies from said needle packaging station to a third workstation that includes said means for automatically winding definite length suture portions depending from said needle-suture assemblies into said package tray.

9. The automated machine as claimed in claim 8, wherein said second workstation further comprises:

(a) a drawing frame, said frame having first and second longitudinal guide members and defining a drawing axis parallel thereto;

(b) means for feeding a flexible indefinite length suture strand to said drawing axis for drawing and cutting;

(c) first and second gripping means for gripping said indefinite length suture strand and drawing it along said drawing axis, said first gripping means mounted for reciprocal movement on said first longitudinal guide member and said second gripping means mounted for reciprocal movement on said second longitudinal guide member; and (d) said second gripping means reciprocal to a start position along said drawing axis and below said cutting means, while said first gripping means is drawing said indefinite length suture strand for a long stroke to an insertion zone located a predetermined distance beyond said means for cutting, whereby said indefinite length suture strand is inserted within the suture receiving opening of an individual needle and cut to a predetermined length by said cutting means after said second gripping means has gripped said indefinite length suture strand at said start position.

10. The automated machine as claimed in claim 8, wherein said means for swaging comprises:

(a) first and second swage die means, said first swage die means fixed in position and having an end thereof defining a portion of a swage die opening, and said second swage die means having an end thereof defining another portion of said swage die opening, said second swage die means reciprocally movable toward and away from said first fixed swage die means, said end of said second swage die means positioned next to said end of said first swage die means to form said swage die opening for receiving the suture receiving opening of a needle; and (b) means for biasing said second swage die means away from said first swage die means for receiving said needle within said swage die opening and for resiliently biasing said first and second swage die means into engagement to grip the suture receiving end of a needle prior to swaging thereof, said means for moving further including means for supplying adequate force to swage said suture receiving opening of said needle about said free end of said definite length suture.

11. The automated machine as claimed in claim 10, wherein said means for sorting comprises:

(a) infeed means for randomly depositing a predetermined amount of needles upon a first conveyor means;

(b) first means for obtaining an image of said needles deposited upon said first conveyor means, said means including digitizing means for converting said image into digital signals;

(c) computer control means for processing said digital signals to obtain positional and orientation data for selected randomly positioned needles upon said first conveyor means; and (d) transfer means for removing one or more said randomly positioned needles from said first conveyor means and positioning said needles upon a second conveyor means for conveyance thereof, wherein said transfer means grasps each of said one or more said selected randomly positioned needles in accordance with its respective positional and orientation data.

12. The automated machine as claimed in claim 10 wherein said means for sequentially receiving said needle-suture assemblies further includes:

(a) package tray support means for supporting said package tray; and (b) means for successively registering said package tray support means and said package tray in incremental movements correlating with the sequential indexing of said needle-suture assemblies to said package tray, wherein said first indexing means successively transfers said needle-suture assemblies to said package tray with a single needle-suture assembly transferred at each registered position.

13. The automated machine as claimed in claim 8 wherein said means for sequentially receiving said needle-suture assemblies further includes:

(a) package tray support means for supporting said package tray; and (b) means for successively registering said package tray support means and said package tray supported thereon in incremental movements correlating with the sequential indexing of said needle-suture assemblies to said package tray, wherein said first indexing means successively transfers said needle-suture assemblies to said package tray with a single needle-suture assembly transferred at each registered position.

14. An automated machine performing multiple simultaneous operations during each machine cycle, said machine automatically attaching a definite length suture to an individual surgical needle having a suture receiving opening formed therein during each machine cycle and automatically packaging a plurality of successively formed needle-suture assemblies in a package tray during successive machine cycles, said machine comprising:

(a) a first workstation including means for sorting a plurality of needles and orienting an individual needle during each machine cycle for automatic and sequential feeding thereof to a subsequent workstation;

(b) a second workstation for forming a needle-suture assembly during each machine cycle including means for automatically cutting an indefinite length of suture material to an individual, definite length suture and means for automatically swaging one of said individual needles during each machine cycle to close said suture receiving opening about a free end of said definite length suture to secure said suture thereto, (c) a needle packaging station including means for sequentially receiving a plurality of said needle-suture assemblies in a package tray with a single needle-suture assembly received during each machine cycle while a subsequent needle-suture assembly is formed at said second workstation, said needle packaging station having a means for automatically winding a plurality of definite length suture portions depending from said needle-suture assemblies into said package tray, (d) a first indexing means for sequentially receiving individual oriented needles fed from said first workstation and sequentially transferring each of said needles from said first workstation to said second workstation to form a needle-suture assembly thereat, said first indexing means sequentially indexing a formed needle-suture assembly from said second workstation to said needle packaging station during each machine cycle, whereby unsorted needles and an indefinite length of suture material are automatically formed into a plurality of oriented needle-suture assemblies and positioned within said package to facilitate their orderly removal therefrom.

15. The automated machine as claimed in claim 14, wherein said means for sorting comprises:

(a) infeed means for randomly depositing a predetermined amount of needles upon a first conveyor means;

(b) first means for obtaining an image of said needles deposited upon said first conveyor means, said means including digitizing means for converting said image into digital signals;

(c) computer control means for processing said digital signals to obtain positional and orientation data for selected randomly positioned needles upon said first conveyor means; and (d) transfer means for removing one or more of said selected randomly positioned needles from said first conveyor means and positioning said needles upon a second conveyor means during each said machine cycle for conveyance thereof, wherein said transfer means grasps each of said one or more said selected randomly positioned needles in accordance with its respective positional and orientation data.

16. The automated machine as claimed in claim 14, wherein said second workstation further comprises:

(a) a drawing frame, said frame having first and second longitudinal guide members and defining a drawing axis parallel thereto;

(b) means for feeding a flexible indefinite length suture strand to said drawing axis for drawing and cutting;

(c) first and second gripping means for gripping said indefinite length suture strand and drawing it along said drawing axis, said first gripping means mounted for reciprocal movement on said first longitudinal guide member and said second gripping means mounted for reciprocal movement on said second longitudinal guide member; and (d) said second gripping means reciprocal to a start position along said drawing axis and below said cutting means, while said first gripping means is drawing said indefinite length suture strand to an insertion zone located a predetermined distance beyond said means for cutting, wherein during said each machine cycle said indefinite length suture strand is inserted within the suture receiving opening of a needle and cut to a predetermined length by said cutting means after said second gripping means has gripped said indefinite length suture strand at said start position.

17. The automated machine as claimed in claims 9 or 16 wherein said feeding means further comprises first and second drive motors for enabling reciprocal movement of respective said first and second gripping means.

18. The automated machine as claimed in claim 17 further comprising a computer control means for enabling said first and second drive motors to alternately draw said indefinite length suture material to said insertion zone.

19. The automated machine as claimed in claim 18 wherein each of said first and second gripping means further include pneumatically operated retractable gripping elements having a first engaged position and a second retracted position, wherein one of said first and second gripping means traverses the drawing axis for a long stroke with gripping elements engaging said indefinite length suture strand, and the other of said first and second gripping means reciprocating along the same axis with the gripping elements retracted to avoid mechanical interference with the gripping means that is engaging said indefinite length suture strand.

20. The automated machine as claimed in claims 14 or 15, wherein said means for swaging comprises:

(a) first and second swage die means, said first swage die means fixed in position and having an end thereof defining a portion of a swage die opening, and said second swage die means having an end thereof defining another portion of said swage die opening, said second swage die means reciprocally movable toward and away from said first fixed swage die means, said end of said second swage die means positioned next to said end of said first swage die means to form said swage die opening for receiving said suture receiving opening of each individually fed needle; and (b) means for biasing said second swage die means away from said first fixed swage die means for receiving each said individually fed needle within said swage die opening and for resiliently biasing said first and second swage dies into engagement to grip the suture receiving end of a needle prior to swaging thereof, said biasing means further including means for supplying adequate force to drive said second swage die means toward said first fixed swage die means to accomplish swaging of said suture receiving opening of said needle about said free end of said definite length suture.

21. The automated machine as claimed in claim 20 wherein said first indexing means includes multi-axis gripper means for sequentially receiving and engaging each individually fed needle in an oriented position once every said machine cycle, and for positioning said suture receiving opening of each said individually fed needle within said swage die opening prior to swaging thereof.

22. The automated machine as claimed in claim 20 wherein said swaging means further includes means for adjusting the position of said first fixed swage die means to change the amount of swage deformation occurring to a suture receiving opening during swaging thereof.

23. The automated machine as claimed in claim 14 or 15 wherein said means for sequentially receiving said needle-suture assemblies further includes:

(a) package tray support means for supporting said package tray; and (b) means for successively registering said package tray support means and said package tray supported thereon in incremental movements correlating with the sequential indexing of said needle-suture assemblies to said package tray, wherein said first indexing means sequentially transfers said needle-suture assemblies to said package tray during said each machine cycle with a single needle-suture assembly transferred at each registered position.

24. The automated machine as claimed in claim 14 wherein said first indexing means includes a first rotary turret, said first and second workstations stationarily spaced about the periphery of said first rotary turret, said machine further including a second indexing means comprising a second rotary turret for sequentially indexing said package tray having said needle-suture assemblies from said needle packaging station to a third workstation that includes said means for automatically winding definite length suture portions depending from said needle-suture assemblies into said package tray, wherein said first rotary turret is indexed once every said machine cycle.

25. The automated machine as claimed in claim 24, wherein said second workstation further comprises:

(a) a drawing frame, said frame having first and second longitudinal guide members and defining a drawing axis parallel thereto;

(b) means for feeding a flexible indefinite length suture strand to said drawing axis for drawing and cutting;

(c) first and second gripping means for gripping said indefinite length suture strand and drawing it along said drawing axis, said first gripping means mounted for reciprocal movement on said first longitudinal guide member and said second gripping means mounted for reciprocal movement on said second longitudinal guide member; and (d) said second gripping means reciprocal to a start position along said drawing axis and below said cutting means, while said first gripping means is drawing said indefinite length suture strand to an insertion zone located a predetermined distance beyond said means for cutting, wherein during said each machine cycle said indefinite length suture strand is inserted within the suture receiving opening of a needle and cut to a predetermined length by said cutting means after said second gripping means has gripped said indefinite length suture strand at said start position.

26. The automated machine as claimed in claim 24, wherein said means for swaging comprises:

(a) first and second swage die means, said first swage die means fixed in position and having an end thereof defining a portion of a swage die opening, and said second swage die means having an end thereof defining another portion of said swage die opening, said second swage die means laterally movable toward and away from said first fixed swage die means, said end of said second swage die means positioned next to said end of said first swage die means to form said swage die opening for receiving the suture receiving opening of a needle; and (b) means for biasing said second swage die means away from said first swage die means for receiving said needle within said swage die opening and for resiliently biasing said first and second swage die means into engagement to grip the suture receiving end of a needle prior to swaging thereof, said means for moving further including means for supplying adequate force to swage said suture receiving opening of said needle about said free end of said definite length suture.

27. The automated machine as claimed in claim 26, wherein said means for sorting comprises:

(a) infeed means for randomly depositing a predetermined amount of needles upon a first conveyor means;

(b) first means for obtaining an image of said needles deposited upon said first conveyor means, said means including digitizing means for converting said image into digital signals;

(c) computer control means for processing said digital signals to obtain positional and orientation data for selected randomly positioned needles upon said first conveyor means; and (d) transfer means for removing one or more of said selected randomly positioned needles from said first conveyor means and positioning said needles upon a second conveyor means for conveyance thereof, wherein said transfer means grasps each of said one or more said selected randomly positioned needles in accordance with its respective positional and orientation data.

28. The automated machine as claimed in claim 26 wherein said means for sequentially receiving said needle-suture assemblies further includes:

(a) package tray support means for supporting said package tray; and (b) means for successively registering said package tray support means and said package tray supported thereon in incremental movements correlating with the sequential indexing of said needle-suture assemblies to said package tray, wherein said first indexing means successively deposits said needle-suture assemblies to said package tray with a single needle-suture assembly transferred at each registered position during said each machine cycle.

29. The automated machine as claimed in claim 24 wherein said means for sequentially receiving said needle-suture assemblies further includes:

(a) package tray support means for supporting said package tray; and (b) means for successively registering said package tray support means and said package tray supported thereon in incremental movements correlating with the sequential indexing of said needle-suture assemblies to said package tray, wherein said first indexing means successively transfers said needle-suture assemblies to said package tray during said each machine cycle with a single needle-suture assembly transferred at each registered position.

30. The automated machine as claimed in claims 13 and 29 wherein said means for automatically winding said definite length suture portions into said package tray further includes:

(a) means for gathering said depending definite length suture portions into a bundled strand and imparting axial tension thereto;

(b) means for imparting rotational movement to said package tray support means and said package tray carried thereby to wind said definite length suture portions into said package, (c) stylus means operatively associated with said suture portion gathering means for winding said bundled strand of depending definite length suture portions into a peripheral channel of said package tray.

31. The automated machine as claimed in claims 1 or 14 wherein said first indexing means sequentially indexes said formed needle-suture assemblies to a pull-test station located between said second workstation and said needle packaging station, said pull-test workstation comprising means for automatically testing swage bond strength of each said needle-suture assembly indexed thereto.

* * * * *

UNITED STATES PATENT AND TRADEMARK OFFICE
CERTIFICATE OF CORRECTION

PATENT NO. : 5,473,810
DATED : December 12, 1995
INVENTOR(S) : David Demarest, et al.

It is certified that error appears in the above-indentified patent and that said Letters Patent is hereby corrected as shown below:

Column 13, line 9: "231 0 is" should read --231 is--

Column 20, line 65: "08/181,607" should read --08/181,601--

Column 25, line 52: "Deal" should read --Dial--

Column 46, line 33, Claim 30: "and" should read --or--

Signed and Sealed this

Eleventh Day of June, 1996

Attest:

BRUCE LEHMAN

Attesting Officer          Commissioner of Patents and Trademarks